(12) United States Patent
Fields et al.

(10) Patent No.: US 11,318,077 B2
(45) Date of Patent: May 3, 2022

(54) RETINALDEHYDE CONTAINING COMPOSITIONS AND METHODS OF USE

(71) Applicant: RODAN & FIELDS, LLC, San Francisco, CA (US)

(72) Inventors: Kathy Ann Fields, San Francisco, CA (US); Kathryn Pregerson Rodan, Oakland, CA (US); George Paul Majewski, Emeryville, CA (US); Timothy John Falla, Woodinville, WA (US); Robert Bianchini, Dana Point, CA (US)

(73) Assignee: RODAN & FIELDS, LLC, San Francisco, CA (US)

( * ) Notice: Subject to any disclaimer, the term of this patent is extended or adjusted under 35 U.S.C. 154(b) by 242 days.

(21) Appl. No.: 16/148,768

(22) Filed: Oct. 1, 2018

(65) Prior Publication Data

US 2019/0099340 A1  Apr. 4, 2019

Related U.S. Application Data

(60) Provisional application No. 62/565,314, filed on Sep. 29, 2017.

(51) Int. Cl.
| | | |
|---|---|---|
| A61K 8/34 | (2006.01) | |
| A61K 8/64 | (2006.01) | |
| A61K 8/891 | (2006.01) | |
| A61K 8/37 | (2006.01) | |
| A61Q 19/08 | (2006.01) | |
| A61K 8/24 | (2006.01) | |
| A61K 8/58 | (2006.01) | |
| A61K 31/08 | (2006.01) | |
| A61K 31/07 | (2006.01) | |
| A61K 8/67 | (2006.01) | |
| A61K 31/203 | (2006.01) | |
| A61K 31/192 | (2006.01) | |

(52) U.S. Cl.
CPC ............... *A61K 8/34* (2013.01); *A61K 8/24* (2013.01); *A61K 8/37* (2013.01); *A61K 8/585* (2013.01); *A61K 8/64* (2013.01); *A61K 8/671* (2013.01); *A61K 8/891* (2013.01); *A61K 31/07* (2013.01); *A61K 31/08* (2013.01); *A61K 31/192* (2013.01); *A61K 31/203* (2013.01); *A61Q 19/08* (2013.01); *A61K 2800/874* (2013.01)

(58) Field of Classification Search
None
See application file for complete search history.

(56) References Cited

U.S. PATENT DOCUMENTS

| | | |
|---|---|---|
| 9,144,434 B1 | 9/2015 | Rodan et al. |
| 9,289,363 B2 | 3/2016 | Shin et al. |
| 9,931,328 B2 | 4/2018 | Kandavilli et al. |
| 2016/0206542 A1 | 7/2016 | Bacqueville et al. |
| 2017/0189297 A1 | 7/2017 | De Lemos et al. |
| 2018/0071190 A1* | 3/2018 | Albrecht ................. A61P 17/00 |

FOREIGN PATENT DOCUMENTS

| | | |
|---|---|---|
| CA | 2707506 C | 3/2016 |
| WO | 2016105332 A1 | 6/2016 |
| WO | 2018022561 A1 | 2/2018 |
| WO | 2019068096 A1 | 4/2019 |

OTHER PUBLICATIONS

International Search Report and Written Opinion for PCT/US2018/053783 dated Jan. 29, 2019.

Rodan & Fields LLC, Ingredient List, Apr. 18, 2017, "http://www.randfconnect.com/wp-content/themes/randfconnect/pdf/ingredient_list_020813.pdf", 9 pages.

* cited by examiner

*Primary Examiner* — Nannette Holloman
(74) *Attorney, Agent, or Firm* — Troutman Pepper Hamilton Sanders LLP

(57) ABSTRACT

This disclosure is directed to compositions comprised of retinaldehyde, one or more skin conditioning agents, and, optionally, one or more additional retinoids. This disclosure is directed. Embodiments are also directed to compositions comprised of retinaldehyde, one or more peptides, one or more skin conditioning agents, one or more calcium containing agents, and, optionally, one or more additional retinoids. Embodiments are also directed to compositions comprised of retinaldehyde, one or more peptides, one or more skin conditioning agents, one or more calcium containing agents, and, optionally, one or more additional retinoids. Additional embodiments disclose methods for treating the skin wherein a characteristic of the skin is improved, the characteristics include firmness, elasticity, fine lines and wrinkles, skin texture, dullness, dyschromia, skin tone, reduction or elimination of acne, and any combination thereof. This disclosure is also directed to kits used for treating the skin with the compositions described herein.

14 Claims, 21 Drawing Sheets

RETINALDEHYDE CONTAINING COMPOSITIONS AND METHODS OF USE

SUMMARY

Embodiments herein are directed to a skin composition comprising retinaldehyde, one or more skin conditioning agents, and, optionally, one or more additional retinoids. Embodiments herein are directed to a skin composition comprising retinaldehyde, one or more skin conditioning agents, one or more calcium containing agents, and, optionally, one or more additional retinoids. Embodiments herein are directed to a skin composition comprising retinaldehyde, one or more peptides, one or more skin conditioning agents, one or more calcium containing agents, and, optionally, one or more additional retinoids. In some embodiments, the optional one or more additional retinoids is selected from the group consisting of retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, 2-(nicotinamido)-ethyl retinoate (NEAR-1), and derivatives and combinations thereof. In some embodiments, the one or more skin conditioning agents is selected from the group consisting of cyclopentasiloxane, dimethicone, polysilicone-11, ethylhexyl hydroxystearate, C12-15 alkyl benzoate, bis-ethylhexyl hydroxydimethoxy benzylmalonate, ethoxydiglycol, hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof. In some embodiments, the optional one or more peptides is selected from the group consisting of palmitoyl hexapeptide-14, oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof. In some embodiments, the optional one or more calcium containing agents is selected from the group consisting of hydroxyapatite, calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof.

Embodiments herein are also directed to a method of treating skin comprising: topically applying a composition to skin, wherein the composition comprises retinaldehyde, one or more skin conditioning agents, and optionally, one or more additional retinoids, one or more peptides and one or more calcium containing agents, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. Embodiments herein are also directed to a method of treating skin comprising: (a) exfoliating the skin; and (b) topically applying a composition to skin, wherein the composition comprises retinaldehyde, one or more skin conditioning agents, and optionally, one or more additional retinoids, one or more peptides and one or more calcium containing agents, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. Embodiments herein are also directed to a method of treating skin comprising: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, one or more skin conditioning agents, and optionally, one or more additional retinoids, one or more peptides and one or more calcium containing agents, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. Embodiments herein are also directed to method of treating skin comprising: (a) cleansing the skin with a daily cleansing mask; (b) topically applying a toner to skin; and (c) topically applying a composition to skin, wherein the composition comprises retinaldehyde, one or more skin conditioning agents, and, optionally, one or more additional retinoids, one or more peptides, one or more calcium containing agents, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

Embodiments herein are also directed to a kit comprising: a micro-exfoliation tool; a topical skin composition comprising: retinaldehyde, one or more skin conditioning agents, and optionally, one or more additional retinoids; and instructions for use. Embodiments herein are also directed to a kit comprising: a micro-exfoliation tool; a topical skin composition comprising: retinaldehyde, one or more skin conditioning agents, and one or more calcium containing agents, and optionally, one or more additional retinoids; and instructions for use. Embodiments herein are also directed to a kit comprising: a micro-exfoliation tool; a topical skin composition comprising: retinaldehyde, one or more peptides, one or more skin conditioning agents, and one or more calcium containing agents and optionally, one or more additional retinoids; and instructions for use.

Embodiments herein are also directed to a kit comprising: a daily cleansing mask; a topical toner; a topical skin composition comprising: retinaldehyde, one or more skin conditioning agents, and, optionally, one or more additional retinoids; and instructions for use. Embodiments herein are also directed to a kit comprising: a daily cleansing mask; a topical toner; a topical skin composition comprising: retinaldehyde, one or more skin conditioning agents, one or more calcium containing agents, and, optionally, one or more additional retinoids; and instructions for use. Embodiments herein are also directed to a kit comprising: a daily cleansing mask; a topical toner; a topical skin composition comprising: retinaldehyde, one or more peptides, one or more skin conditioning agents, one or more calcium containing agents, and, optionally, one or more additional retinoids; and instructions for use.

BRIEF DESCRIPTION OF THE DRAWINGS

For a better understanding of the nature and advantages of the present invention, refer to the following detailed description taken in connection with the accompanying drawings, in which.

DETAILED DESCRIPTION

Figure 1:
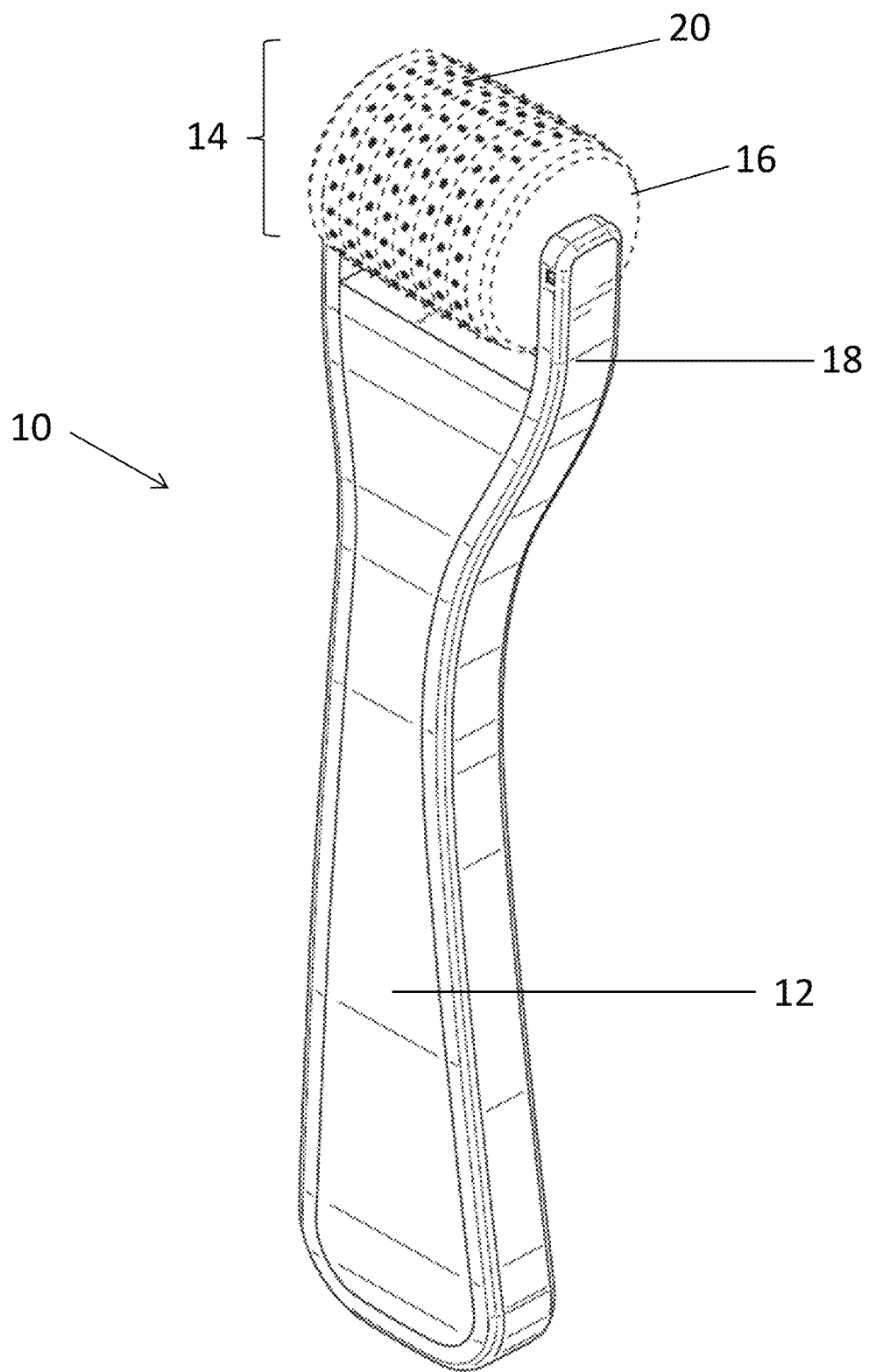
FIG. 1 shows a view of the micro-exfoliation tool.

Proper skin care is important for heath and cosmetic reasons. Skin is a vital organ and a breakdown in the skin can adversely affect the skin's function as a barrier and make it susceptible to infection. A breakdown in the skin can also be very painful, such as the case of excessively dry skin. Visual irregularities and fine lines and wrinkles in the skin can adversely affect a person's confidence and other people's perceptions.

There remains a need for improved methods of treating skin and maintaining or improving its health and cosmetic features. It is against this background that the present disclosure is made.

Surprisingly, it has been found that using a micro-exfoliation tool together with selected skin care agents results in improved skin health and appearance. It was also surprising that skin compositions containing retinaldehyde in place of retinol or adapalene resulted in faster and/or greater improvement in skin characteristics, including, firmness, elasticity, fine lines and wrinkles, skin texture, dullness, dyschromia, and skin tone. Further, skin compositions containing retinaldehyde were much more tolerable when compared with other skin compositions.

It was also surprisingly found that the skin compositions containing retinaldehyde, in place of benzoyl peroxide, was tolerable and effective against mild to moderate acne vulgaris. The skin treated with compositions described herein saw a reduction or elimination of acne.

These and other embodiments will be apparent to those of skill in the art and others in view of the following detailed description. The present disclosure generally relates to skin treatment using a retinaldehyde containing composition and/or a micro-exfoliation tool and/or additional selected skin care agents. While not wanting to be bound by theory, it is believed that the combination of the micro-exfoliation tool and the selected skin care agents increases the uptake of the selected skin care agents by the epidermis (outer layer of skin) than if the skin care agent was just placed on top of the epidermis. This is believed to be in part because the micro-exfoliation tool increases the surface area of the epidermis by creating micro pores or holes in the skin, thereby allowing a greater number of skin cells on the epidermis to contact and benefit from the selected skin care agent. One result of this is that a user can see improved results in a shorter period of time.

Before the present compositions and methods are described, it is to be understood that this invention is not limited to the particular processes, compositions, or methodologies described, as these may vary. Moreover, the processes, compositions, and methodologies described in particular embodiments are interchangeable. Therefore, for example, a composition, dosage regimens, route of administration, and so on described in particular embodiments may be used in any of the methods described in other particular embodiments. It is also to be understood that the terminology used in the description is for the purpose of describing the particular versions or embodiments only, and is not intended to limit the scope of the present invention which will be limited only by the appended claims.

In embodiments directed to methods which include a series of steps, it is to be understood that the steps can occur in any order. Though an embodiment describes steps (a), (b) and (c), unless specifically stated, the method can also occur as steps (b), (a), and (c) or (c), (b), and (a), or any combination of described steps. It is to be understood that any order of steps is described and claimed herein, unless otherwise specified.

Unless defined otherwise, all technical and scientific terms used herein have the same meanings as commonly understood by one of the ordinary skill in the art. Although any methods similar or equivalent to those describe herein can be used in the practice or testing of embodiments of the present invention, the preferred methods are now described. All publications and references mentioned herein are incorporated by reference. Nothing herein is to be construed as an admission that the invention is not entitled to antedate such disclosure by virtue of prior invention.

It must be noted that, as used herein, and in the appended claims, the singular forms "a," "an," and "the" include plural reference unless the context clearly dictates otherwise.

As used herein, the term "about" means plus or minus 10% of the numerical value of the number with which it is being used. Therefore, about 50% means in the range of 45%-55%.

The term "administering" when used in conjunction with a therapeutic means to administer a therapeutic directly or indirectly into or onto a target tissue to administer a therapeutic to a patient whereby the therapeutic positively impacts the tissue to which it is targeted. "Administering"

may include the act of self-administration or administration by another person such as a health care provider.

As used herein, the terms "comprising," "comprise," "comprises," and "comprised" are inclusive or open-ended and do not exclude additional, unrecited elements or method steps.

As used herein, the term "consisting essentially of" or "consists essentially of" means that the composition or method includes the specified components or steps and those that do not materially affect the basic and novel characteristics of the claimed invention.

As used herein, the term "consists of" or "consisting of" means that the composition or method includes only the elements, steps, or ingredients specifically recited in the particular embodiment or claim.

Specific embodiments disclosed herein may be further limited in the claims using "consisting of" or "consisting essentially of" language, rather than "comprising". In other words, though embodiments described herein use the phrase "comprising" or "comprises," any embodiment described herein can be replaced with "consisting of"/"consists of" or "consisting essentially of"/"consists essentially of."

The term "cosmetic" means an agent utilized, and/or intended to be applied to the human body for cleansing, beautifying, promoting attractiveness, altering the appearance of the skin or any combination thereof.

The term "cosmetic composition" shall mean a composition including at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The terms "effective amount" or "effective dose" as used herein are interchangeable and may refer to the amount of an active agent or compound or composition that has the effect of moisturizing, cleansing, beautifying, promoting attractiveness, altering the appearance of the skin, promoting the exfoliation of dry skin, promoting the digestion of desmosomes, normalizing cell maturation, modulating keratinocyte function, normalizing keratinocyte differentiation, normalizing keratinocyte proliferation, modulating phosphatidylglycerol content of keratinocytes, modulating and/or improving the moisture content of the skin, promoting the retention of long lasting hydration in the skin, increasing skin moisture, improving skin water balance, increasing skin hydration, decreasing transepidermal water loss, reducing evaporation of water from the skin, treating and/or preventing dry and/or irritated skin, defending against, and reducing visible signs of aging for noticeably firmer, smoother, and flawless looking skin, erasing the appearance of premature aging, including brown spots, dullness and discoloration, visibly brightening the skin, reducing the appearance of fine lines and wrinkles, creating a radiant complexion, shielding the skin again biological and environmental aggressors associated with dry, irritated and sensitive skin, helping the skin retain moisture and remain comfortable when challenged by climate and other environmental aggressors, rehydrating the skin, to repairing, renewing, enhancing the skin's natural moisture barrier, improving acne, improving mild to moderate acne vulgaris, reducing or eliminating the symptoms of acne including plugged pores, and outbreaks of inflamed lesions or pimples.

The term "inhibit," "suppress," "decrease," "interfere," and/or "reduce" (and like terms) generally refers to the act of reducing, either directly or indirectly, a function, activity, or behavior relative to the natural, expected, or average or relative to current conditions.

The term "improves" is used to convey that the present invention changes either the appearance, form, characteristics, structure, function and/or physical attributes of the skin to which it is being provided, applied or administered. "Improves" may also refer to the overall physical state of an individual to whom an active agent has been administered. For example, an individual may feel that their skin has "improved" by administration of a composition containing an active agent.

The term "increase," "enhance," "stimulate," and/or "induce" (and like terms) generally refers to the act of improving or increasing, either directly or indirectly, the look and feel of the skin.

In each of the embodiments disclosed herein, the compositions and methods may be utilized with or on a subject in need of such treatment, which may also be referred to as "in need thereof." As used herein, the phrase "in need thereof" means that the subject has been identified as having a need for the particular method or treatment and that the treatment has been given to the subject for that particular purpose.

The phrase "micro-exfoliation tool" includes the reference to "derma roller" and "micro-needle."

"Optional" or "optionally" may be taken to mean that the subsequently described component, event or circumstance may or may not occur, and that the described embodiments include instances where the component is included and instances where it does not.

As used herein, the term "patient" and "subject" are interchangeable and may be taken to mean any living organism, which may be treated with compounds of the present invention. As such, the terms "patient" and "subject" may include, but is not limited to, any non-human mammal, primate or human. In some embodiments, the "patient" or "subject" is an adult, child, or infant.

The term "retinaldehyde" is also known as retinal or vitamin A aldehyde and may be used interchangeably throughout this disclosure.

The term "skin" as used herein refers to the organ of the body which protects the subject from environmental irritations, regulates the body's temperature and allows for external sensations. The "skin" is separated into three layers: the outermost layer called the epidermis which contains melanocytes; the dermis which contains connective tissue, hair follicles and sweat glands; and the deepest subcutaneous layer called the hypodermis which is made up of fat and connective tissue.

As used herein, the term "topically" and "topical" refers to application of the compositions of the present invention to the surface of the skin and mucosal cells and tissues. The skin can be anywhere or it can be specifically on the face, neck, hands, or body.

As used herein the terms "topical formulation" and "topical compositions" refer to a formulation or composition that may be applied to skin or a mucosa or applied transdermally. The skin can be anywhere or it can be specifically on the face, neck, hands, or body. Topical formulations or compositions may, for example, be used to confer therapeutic benefit to a patient or cosmetic benefits to a consumer. Topical formulations or compositions are advantageous in that it avoids first-pass metabolism, circumvents gastrointestinal absorption, can allow delivery of an active ingredient with a relatively short biological half-life and/or a narrow therapeutic window, and can allow delivery of an active ingredient to a localized spot on the skin.

The term "topical administration" is used in its conventional sense to mean delivery of a substance, such as an active agent, to the skin.

The term "transdermal administration" is used to mean administration through the skin. Transdermal administration is often applied where systemic delivery of an active is desired, although it may also be useful for delivering an active to tissues underlying the skin with minimal systemic absorption.

The terms "treat," "treated," or "treating" as used herein refers to therapeutic treatment, cosmetic treatment and/or prophylactic or preventative measures, wherein the object is to prevent, reduce, eliminate or slow down (lessen) an undesired physiological condition, disorder or disease, or to obtain beneficial or desired clinical results (e.g. decrease wrinkles, increase firmness or elasticity, improve skin tone, dullness, dyschromia, and texture, as well as a reduction or elimination of acne.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Compositions

Described herein are effective anti-acne compositions, anti-aging compositions, and skin lightening compositions.

Embodiments herein are directed to a skin composition comprising retinaldehyde, one or more skin conditioning agents, and, optionally, one or more additional retinoids.

Embodiments herein are directed to a skin composition comprising retinaldehyde, one or more skin conditioning agents, one or more calcium containing agents, and, optionally, one or more additional retinoids.

Embodiments herein are directed to topical skin compositions comprising retinaldehyde, one or more peptides, one or more skin conditioning agents, one or more calcium containing agents, and, optionally, one or more additional retinoids.

As described herein, skin compositions may be formulated to contain retinaldehyde in Hydroxysomes®. Hydroxysomes are designed to dermally deliver retinaldehyde with a continuous supply of calcium as nanoporous calcium phosphate particles. In some embodiments, the hydroxysomes is supplied by Laboratory Skin Care, Inc.

The skin compositions described herein may be anhydrous, i.e. the composition does not contain water.

As described herein, the topical skin composition comprises optionally, one or more additional retinoids, wherein the optional one or more additional retinoids is selected from the group consisting of retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, 2-(nicotinamido)-ethyl retinoate (NEAR-1), and derivatives and combinations thereof. In all forgoing embodiments, additional embodiments are described wherein the composition does not contain retinol.

As described herein, the topical skin composition comprises one or more skin conditioning agents, wherein the one or more skin conditioning agents is selected from the group consisting of cyclopentasiloxane, dimethicone, polysilicone-11, ethylhexyl hydroxystearate, C12-15 alkyl benzoate, bis-ethylhexyl hydroxydimethoxy benzylmalonate, ethoxydiglycol, hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof.

As described herein, the topical skin composition comprises optionally one or more peptides, wherein the optional one or more peptides is selected from the group consisting of palmitoyl hexapeptide-14, oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof.

As described herein, the topical skin composition comprises optionally one or more calcium containing agents, wherein the optional one or more calcium containing agents is selected from the group consisting of hydroxyapatite, calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof.

In some embodiments, the topical skin composition further comprises niacinamide, nicotinamide, vitamin B3, nicotinic acid, or niacin.

As described herein, the active ingredients of the skin compositions include, but are not limited to, retinaldehyde, the retinoids, the peptides, the calcium containing agents, and the skin conditioning agents. It is also known in the art that the active ingredients may be contained in such compositions with cosmetically and/or pharmaceutically acceptable secondary agents, such as diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

In certain embodiments, the active ingredients range from about 0.1% w/w to about 20% w/w, about 1% w/w to about 15% w/w, about 2% w/w to about 10% w/w, or about 3% w/w to about 5% w/w. In certain embodiments, the secondary ingredients range from about 0.00001% w/w to about 90% w/w, about 0.00001% w/w to about 85% w/w, about 0.00001% w/w to about 75% w/w, about 0.0001% w/w to about 70% w/w, about 0.001% w/w to about 65% w/w, about 0.01% w/w to about 50% w/w, about 0.1% w/w to about 45% w/w, about 1% w/w to about 40% w/w, about 5% w/w to about 35% w/w, about 10% w/w to about 30% w/w, or about 15% w/w to about 25% w/w. In preferred embodiments, the topical skin composition comprises about 0.1% w/w to about 1% w/w retinaldehyde, about 50% w/w to about 75% w/w cyclopentasiloxane, about 15% w/w to about 20% w/w dimethicone, about 10% w/w to about 15% w/w polysilicone-11, about 1% w/w to about 5% w/w ethylhexyl hydroxystearate, about 1% w/w to about 5% w/w C12-15 alkyl benzoate, about 0.00001% w/w to about 0.099% w/w palmitoyl hexapeptide-14, about 0.1% w/w to about 1% w/w retinyl palmitate, about 0.1% w/w to about 1% w/w bis-ethylhexyl hydroxydimethoxy benzylmalonate, about 0.00001% w/w to about 0.099% w/w hydroxyapatite, and about 0.1% w/w to about 1% w/w ethoxydiglycol.

In preferred embodiments, the topical skin composition comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol. In preferred embodiments, the topical skin composition comprises about 0.1% w/w to about 5% w/w retinaldehyde, about 50% w/w to about 90% w/w cyclopentasiloxane, about 5% w/w to about 30% w/w dimethicone, about 5% w/w to about 25% w/w polysilicone-11, about 0.1% w/w to about 10% w/w ethylhexyl hydroxystearate, about 0.1% w/w to about 5% w/w C12-15 alkyl benzoate, about 0.00001% w/w to about 1% w/w palmitoyl hexapeptide-14, about 0.01% w/w to about 5% w/w retinyl palmitate, about 0.01% w/w to about 5% w/w bis-ethylhexyl hydroxydimethoxy benzylmalonate, about 0.001% w/w to about 5% w/w hydroxyapatite, and about 0.01% w/w to about 5% w/w ethoxydiglycol. In preferred embodiments, the topical skin composition comprises about 0.458% w/w retinaldehyde, about 65.720% w/w cyclopentasiloxane, about 16.776% w/w dimethicone, about 11.842% w/w polysilicone-11, about 2.467% w/w ethylhexyl hydroxystearate, about 1.480% w/w C12-15 alkyl benzoate, about 0.0009868% w/w palmitoyl hexapeptide-14, about 0.59% w/w retinyl palmitate, about 0.2% w/w bis-ethylhexyl hydroxydimethoxy benzylmalonate, 0.0716% w/w hydroxyapatite, and about 0.3947% w/w ethoxydiglycol.

In preferred embodiments, the topical skin composition comprises retinaldehyde, dimethicone, isododecane, polysilicone-11, L-ascorbic acid, dimethyl isosorbide, and hydroxypinacolone retinoate. In preferred embodiments, the topical skin composition comprises about 0.1% w/w to about 1% w/w retinaldehyde, about 50% w/w to about 85% w/w Gransil DMID® (combination of dimethicone, isododecane, polysilicone-11), about 5% w/w to about 25% w/w L-ascorbic acid, about 1% w/w to about 10% w/w isododecane, about 0.01% w/w to about 5% w/w Granactive Retinoid® (combination of dimethyl isosorbide, and hydroxypinacolone retinoate).

In preferred embodiments, the topical skin composition comprises retinaldehyde, water, xanthan gum, glycerin, caprylic/Capric triglycerides, cetyl alcohol, stearyl alcohol, glyceryl stearate, PEG-100 stearate, dimethicone, polyacrylate-13, polyisobutene, polysorbate-20, phenoxyethanol, ethylhexylglycerin, and hydroxyapatite. In preferred embodiments, the topical skin composition comprises about 0.1% w/w to about 1% w/w retinaldehyde, about 65% w/w to about 90% w/w water, about 0.01% w/w to about 1% w/w xanthan gum, about 0.01% w/w to about 5% w/w glycerin, about 0.01% w/w to about 5% w/w caprylic/Capric triglycerides, about 0.01% w/w to about 5% w/w cetyl alcohol, about 0.01% w/w to about 5% w/w stearyl alcohol, about 0.01% w/w to about 1% w/w Lipomulse-165® (combination of glyceryl stearate, PEG-100 stearate), about 0.01% w/w to about 5% w/w dimethicone, about 0.01% w/w to about 5% w/w Sepiplus-400® (combination of polyacrylate-13, polyisobutene, polysorbate-20), about 0.01% w/w to about 5% w/w Euxyl PE 9010® (combination of phenoxyethanol, ethylhexylglycerin), and about 0.01% w/w to about 1% w/w hydroxyapatite.

The cosmetic compositions described herein may be prepared, packaged, or sold in bulk as a single unit dose or as multiple unit doses and may be administered in the conventional manner by any route where they are active. For example, the compositions may be administered subcutaneously, topically, and transdermally, such as in the form of patches, toners, cleanser, moisturizers, and creams. Specific modes of administration will depend on the indication. The selection of the specific route of administration and the dose regimen may be adjusted or titrated by the artisan according to known methods in order to obtain the optimal clinical response. All of the methods described herein may be carried out by administering the skin compositions described herein by any such route for administration described herein. Additionally, the skin compositions disclosed herein may be delivered by using any such route of administration for all of the dosage regimens described herein. The compositions and amounts of non-active ingredients in such a composition may depend on the amount of the active ingredient. Such parameters may be readily appreciated and understood by one of skill in the art.

Embodiments of the invention are not limited to any particular agent encompassed by the classes of agents described above, and any agent that falls within any of these categories may be utilized in embodiments of the invention. Non-limiting examples of such agents are provided for clarity. Any of the secondary agents described above may be useful in embodiments of the invention.

Methods of Use

Described herein are methods of treating skin wherein the skin composition is effective as an anti-acne composition, an anti-aging composition, and a skin lightening composition.

Embodiments herein are also directed to a method of treating skin comprising: topically applying a composition, as described herein, to skin, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In some embodiments, the method of treating skin comprises: topically applying a composition to skin, wherein the composition comprises retinaldehyde, one or more skin conditioning agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. In some embodiments, the method of treating skin comprises: topically applying a composition to skin, wherein the composition comprises retinaldehyde, one or more skin conditioning agents, and one or more calcium containing agents and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. In some embodiments, the method of treating skin comprises: topically applying a composition to skin, wherein the composition comprises retinaldehyde, one or more peptides, one or more skin conditioning agents, and one or more calcium containing agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

As described herein, skin compositions may be formulated to contain retinaldehyde in Hydroxysomes®. Hydroxysomes are designed to dermally deliver retinaldehyde with a continuous supply of calcium as nanoporous calcium phosphate particles. In some embodiments, the hydroxysomes is supplied by Laboratory Skin Care, Inc.

The skin compositions described herein may be anhydrous, i.e. the composition does not contain water.

In certain embodiments, the optional one or more additional retinoids is selected from the group consisting of retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, 2-(nicotinamido)-ethyl retinoate (NEAR-1), and derivatives and combinations thereof. In all forgoing embodiments, additional embodiments are described wherein the composition does not contain retinol. In certain embodiments, the one or more skin conditioning agents is selected from the group consisting of cyclopentasiloxane, dimethicone, polysilicone-11, ethylhexyl hydroxystearate, C12-15 alkyl benzoate, bis-ethylhexyl hydroxydimethoxy benzylmalonate, ethoxydiglycol, hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof. In certain embodiments, the optional one or more peptides is selected from the group consisting of palmitoyl hexapeptide-14, oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof. In certain embodiments, the optional one or more calcium containing agents is selected from the group consisting of hydroxyapatite, calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof. In some embodiments, the topical skin composition further comprises niacinamide.

In preferred embodiments, the method of treating skin comprises: topically applying a composition to skin, wherein the composition comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: topically applying a composition to skin, wherein the composition comprises retinaldehyde, dimethicone, isododecane, polysilicone-11, L-ascorbic acid, dimethyl isosorbide, and hydroxypinacolone retinoate, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: topically applying a composition to skin, wherein the composition comprises retinaldehyde, water, xanthan gum, glycerin, caprylic/capric triglycerides, cetyl alcohol, stearyl alcohol, glyceryl stearate, PEG-100 stearate, dimethicone, polyacrylate-13, polyisobutene, polysorbate-20, phenoxyethanol, ethylhexylglycerin, and hydroxyapatite, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In some embodiments, the method of treating skin results in anti-acne, anti-aging, and skin lightening characteristics. In some embodiments, the method of treating skin improves skin firmness, measured by the fullness and plumpness of the skin. In some embodiments, the method of treating skin improves skin elasticity and resiliency, measured by the bounce-back of the skin. In some embodiments, the method of treating skin improves lines and wrinkles, measured by visible evaluation of the skin or replica analysis. In some embodiments, the method of treating skin refines skin texture, measured by smoother, softer and more even skin. In some embodiments, the method of treating skin improves dullness and provides a more even skin tone, measured as more radiant and luminous skin. In some embodiments, the method of treating skin provides in improvement in dyschromia, measured as a lightening of the skin. The improvement in the characteristics of the skin can be measured by ultrasound, measuring improvement in skin density. In some embodiments, the method of treating skin provides an improvement in mild to moderate acne vulgaris. The improvement is measured as reduction or elimination of the symptoms of acne including plugged pores, and outbreaks of inflamed lesions or pimples.

Embodiments herein are also directed to a method of treating skin comprising: (a) exfoliating the skin; and (b) topically applying a composition, as described herein, to skin, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In embodiments described herein, the method of treating skin comprises: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, one or more peptides, one or more skin conditioning agents, and one or more calcium containing agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In embodiments described herein, the method of treating skin comprises: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, one or more skin conditioning agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In embodiments described herein, the method of treating skin comprises: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, one or more skin conditioning agents, and one or more calcium containing agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

The micro-exfoliation tool of the present disclosure is designed to create micro pores, channels, or holes in the epidermis or outer layer of the skin. In some embodiments, the micro-exfoliation tool is a roller attached to a handle or wand, such as that shown in FIG. 1. FIG. 1 generally shows a micro-exfoliation tool 10. The micro-exfoliation tool 10 includes a handle or wand 12 and a head 14 attached to the handle 12. The head 14 includes a roller 16. In some embodiments, the head is configured as a stamp. The roller 16 is held in place by a mechanism of mounting the roller to the handle, such a mechanism is a U-shaped collar 18 that is attached to the handle or wand 12 and engages the roller 16 at either end in such a way that allows the roller 16 to rotate. The roller 16 includes one or more needles 20. FIG. 1 shows the needles 20 in rows, but it is understood that the needles may be arranged in a variety of configurations. The micro-exfoliation tool 10 is preferably easily manufactured. In some embodiments, the handle 12, head 14, including the mechanism of mounting the roller to the handle or collar 18 and the roller 16 are injection molded plastic. The needles 20 are preferably stainless steel, and more preferably surgical grade stainless steel. In some embodiments, the one or more needles are made of other metals, such as bronze, platinum, gold, silver, or copper.

Figure 2:
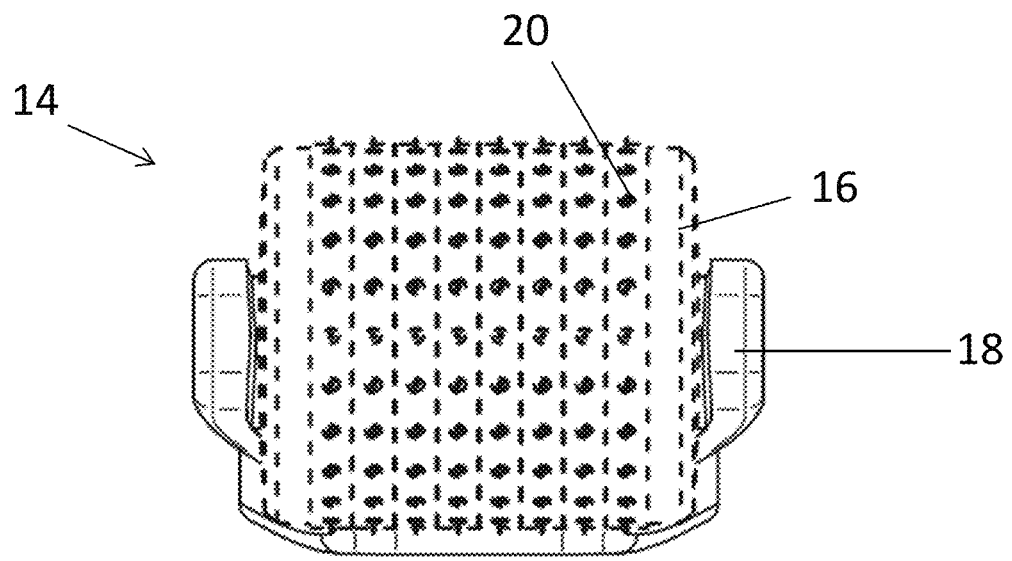
FIG. 2 shows a close up of the micro-exfoliation tool head, including the roller and the needles.

FIG. 2 shows a close up of the head 14, including the collar 18, roller 16, and needles 20. The needles 20 preferably form micro holes, pores, or channels in the epidermis of the skin. It is understood that other structures may be used instead of needles. When using needles, the needles are preferably solid and made of stainless steel, but can be made of other metals, such as bronze, platinum, gold, silver, or copper. The needles are preferably from about 0.1 mm to about 0.5 mm in length so that when the micro-exfoliation tool is placed on skin and rolled using moderate pressure, the needles penetrate only the epidermis, and not the deeper layers of skin. In some embodiments, the needles do not penetrate more than about 100 microns to 500 microns into the epidermis. The needles are from about 0.01 to about 0.5 mm in thickness.

In some embodiments, needles 20 are configured to transmit radio frequency (RF) or electrical stimulation through the needles. Not wishing to be bound by theory, radio frequency skin tightening is an aesthetic technique that uses RF energy to heat tissue and stimulate subdermal collagen production in order to reduce the appearance of fine lines and loose skin. The technique induces tissue remodeling and production of new collagen and elastin. Low-level electrical stimulation has been shown to increase muscle mass and muscle tone, and may be useful to stimulate collagen and elastin production, and improve facial contour. Additionally, electricity is used to physically enhance skin penetration of described compositions through high voltage, short duration pulses applied to the skin. In some embodiments, the needles 20 are configured to transmit heat. In some embodiments, the needles 20 are configured to transmit ultrasound.

In some embodiments, the head is configured as a stamp. The stamp can be pressed against the skin using moderate pressure. In some embodiments, the stamp is capable of vibrating.

In some embodiments, the micro-exfoliation tool can be scaled slightly smaller for use on the face or slightly larger for use on the body or scalp, reflecting the respective differences in surface area of the face versus the rest of the body or scalp. During use on the face, it may be beneficial to divide the face into sections such as the forehead, right side, left side, chin, and neck. A user may then roll or press the head of the micro-exfoliation tool of FIG. 1 over each section using moderate pressure. In some embodiments, it may be beneficial for the user to change the rolling direction with each pass. A similar method can be used when treating other body parts or the scalp (i.e., dividing into sections and rolling the micro-exfoliation tool over the various sections, changing the rolling direction from time to time).

In embodiments described herein, the method of treating skin comprises: (a) exfoliating the skin using a micro-dermabrasion paste, an exfoliating scrub, or other exfoliating tool; and (b) topically applying a composition to skin, wherein the composition comprises retinaldehyde, one or more peptides, one or more skin conditioning agents, and one or more calcium containing agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In embodiments described herein, the method of treating skin comprises: (a) exfoliating the skin using a micro-dermabrasion paste, an exfoliating scrub, or other exfoliating tool; and (b) topically applying a composition to skin, wherein the composition comprises retinaldehyde, one or more skin conditioning agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In embodiments described herein, the method of treating skin comprises: (a) exfoliating the skin using a micro-dermabrasion paste, an exfoliating scrub, or other exfoliating tool; and (b) topically applying a composition to skin, wherein the composition comprises retinaldehyde, one or more skin conditioning agents, and one or more calcium containing agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

The micro-exfoliation tool, micro-dermabrasion paste, exfoliating scrub, or other exfoliating tool and selected skin compositions can be used to treat any skin surface on a human. Exemplary skin surfaces can include the scalp, the face, neck, and decolletage, and the body, such as the back, arms, legs, hands, feet, chest, stomach, and buttocks. The micro-exfoliation tool and skin care agents can be used to treat sensitive skin such as that found on the face, neck, and decolletage as well as tough skin such as that found on knees, elbows, hands, and feet. Further, the micro-exfoliation tool, micro-dermabrasion paste, exfoliating scrub, or other exfoliating tool and selected skin compositions may be used to treat a wide variety of people of all ages, skin colors, and skin types. For example, the micro-exfoliation tool, micro-dermabrasion paste, exfoliating scrub, or other exfoliating tool and selected skin compositions can be used to treat people from infants, to children, to teenagers, to adults, and the elderly. The micro-exfoliation tool, micro-dermabrasion paste, an exfoliating scrub, or other exfoliating tool and selected skin compositions can be used to treat a variety of skin colors including fair, olive, tan, brown, and black, and all of the variations in between. Finally, the micro-exfoliation tool, micro-dermabrasion paste, exfoliating scrub, or other exfoliating tool and selected skin compositions can be used to treat a variety of skin types including dry, normal, oily, sensitive, and acne-prone skin, and combinations of these.

The micro-exfoliation tool, micro-dermabrasion paste, exfoliating scrub, or other exfoliating tool and selected skin compositions can be used to treat, maintain, or improve a variety of skin care features or ailments such as skin health and integrity, skin healing, scalp irregularities or ailments, and visual or cosmetic irregularities or ailments.

The micro-exfoliation tool, micro-dermabrasion paste, exfoliating scrub, or other exfoliating tool and selected skin compositions can be used to maintain skin health by improving the skin integrity and water retention. Healthy skin retains water well compared to dry skin. When the micro-exfoliation tool, micro-dermabrasion paste, exfoliating scrub, or other exfoliating tool and selected skin compositions are used as directed for a period of time, the skin should have an improvement in transepidermal water loss (TEWL).

The micro-exfoliation tool, micro-dermabrasion paste, exfoliating scrub, or other exfoliating tool and selected skin compositions can be used to maintain a healthy scalp, or treat or improve scalp irregularities and ailments such as dandruff, dry scalp, baldness, hair thinning, and alopecia. The micro-exfoliation tool, micro-dermabrasion paste, exfoliating scrub, or other exfoliating tool and selected skin compositions can also be used to improve the health, quality, look or feel of hair by maintaining a healthy scalp, or treating the scalp. For example, the micro-exfoliation tool, micro-dermabrasion paste, exfoliating scrub, or other exfoliating tool and selected skin compositions can be used to improve hair texture, hair breakage, hair volume, and hair shine.

Finally, the micro-exfoliation tool, micro-dermabrasion paste, exfoliating scrub, or other exfoliating tool and selected skin compositions can be used to maintain healthy skin, or treat or improve skin irregularities and ailments such as scarring, sun damage, fine lines, deep lines or wrinkles, acne, blocked pores, blackheads, dry skin, oily skin, birthmarks, irregular skin tone or color, pore size, stretch marks, uneven texture, age spots, lack of firmness or skin tightness, cellulite, spider veins, fungus, rashes, keratosis pilaris, hair growth in the case of areas where hair growth is undesired, irritation or skin sensitivities, redness, puffiness or bloating, eczema, psoriasis, and rosacea.

In some embodiments, the micro-exfoliation tool, micro-dermabrasion paste, exfoliating scrub, or other exfoliating tool and the selected skin compositions can be used as part of a skin care regimen where particular skin compositions, such as, moisturizers, toners, cleanser, and serums, are used together with the micro-exfoliation tool. For example, when treating the scalp, it may be beneficial to use the micro-exfoliation tool with at least one skin composition that is directed to maintaining, treating, or improving scalp health and hair loss such as an antidandruff agent, a cleanser, a moisturizer, or a hair conditioner. Preferred skin care agents for the scalp include minoxidyl, coal tar, salicylic acid, selenium sulfide, sulfur, zinc pyrithione, and their derivatives and combinations. In some embodiments, it may be beneficial to use the micro-exfoliation tool, micro-dermabrasion paste, exfoliating scrub, or other exfoliating tool with an agent that is part of a shampoo, conditioner, hair mask, scalp treatment, pre-treatment, or other treatment or tonic composition.

As described herein, the method of treating skin comprises: topically applying a composition to skin, wherein the composition comprises optionally one or more additional retinoids, wherein the optional one or more additional retinoids is selected from the group consisting of retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, 2-(nicotinamido)-ethyl retinoate (NEAR-1), and derivatives and combinations thereof. In all forgoing embodiments, additional embodiments are described wherein the composition does not contain retinol. As described herein, the one or more skin conditioning agents is selected from the group consisting of cyclopentasiloxane, dimethicone, polysilicone-11, ethylhexyl hydroxystearate, C12-15 alkyl benzoate, bis-ethylhexyl hydroxydimethoxy benzylmalonate, ethoxydiglycol, hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof. As described herein, the optional one or more peptides is selected from the group consisting of palmitoyl hexapeptide-14, oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof. As described herein, the optional one or more calcium containing agents is selected from the group consisting of hydroxyapatite, calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof.

As described herein, skin compositions may be formulated to contain retinaldehyde in Hydroxysomes®. Hydroxysomes are designed to dermally deliver retinaldehyde with a continuous supply of calcium as nanoporous calcium phosphate particles. The skin compositions described herein may be anhydrous, i.e. the composition does not contain water. In some embodiments, the hydroxysomes is supplied by Laboratory Skin Care, Inc.

As described herein, the method of treating skin comprises: topically applying a composition to skin, wherein the composition further comprises niacinamide, nicotinamide, vitamin B3, nicotinic acid, or niacin.

In preferred embodiments, the method of treating skin comprises: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, dimethicone, isododecane, polysilicone-11, L-ascorbic acid, dimethyl isosorbide, and hydroxypinacolone retinoate, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin, wherein the composition comprises retinaldehyde, water, xanthan gum, glycerin, caprylic/Capric triglycerides, cetyl alcohol, stearyl alcohol, glyceryl stearate, PEG-100 stearate, dimethicone, polyacrylate-13, polyisobutene, polysorbate-20, phenoxyethanol, ethylhexylglycerin, and hydroxyapatite, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) exfoliating the skin using a micro-dermabrasion paste, an exfoliating scrub, or other exfoliating tool; and (b) topically applying a composition to skin, wherein the composition comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) exfoliating the skin using a micro-dermabrasion paste, an exfoliating scrub, or other exfoliating tool; and (b) topically applying a composition to skin, wherein the composition comprises retinaldehyde, dimethicone, isododecane, polysilicone-11, L-ascorbic acid, dimethyl isosorbide, and hydroxypinacolone retinoate, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) exfoliating the skin using a micro-dermabrasion paste, an exfoliating scrub, or other exfoliating tool; and (b) topically applying a composition to skin, wherein the composition comprises retinaldehyde, water, xanthan gum, glycerin, caprylic/Capric triglycerides, cetyl alcohol, stearyl alcohol, glyceryl stearate, PEG-100 stearate, dimethicone, polyacrylate-13, polyisobutene, polysorbate-20, phenoxyethanol, ethylhexylglycerin, and hydroxyapatite, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In certain embodiments, the method further comprises a step (c) topically applying a second agent to the skin, wherein the second agent is selected from the group consisting of a cleanser, a toner, a moisturizer, a serum, and any combination thereof.

In some embodiments, the method of treating skin results in anti-acne, anti-aging, and skin lightening characteristics. In some embodiments, the method of treating skin improves skin firmness, measured by the fullness and plumpness of the skin. In some embodiments, the method of treating skin improves skin elasticity and resiliency, measured by the bounce-back of the skin. In some embodiments, the method of treating skin improves lines and wrinkles, measured by visible evaluation of the skin or by replica analysis. In some embodiments, the method of treating skin refines skin texture, measured by smoother, softer and more even skin. In some embodiments, the method of treating skin improves dullness and provides a more even skin tone, measured as more radiant and luminous skin. In some embodiments, the method of treating skin provides in improvement in dyschromia, measured as a lightening of the skin. The improvement in the characteristics of the skin can be measured by ultrasound, measuring improvement in skin density. In some embodiments, the method of treating skin provides an improvement in mild to moderate acne vulgaris. The improvement is measured as reduction or elimination of the symptoms of acne including plugged pores, and outbreaks of inflamed lesions or pimples.

In some embodiments, the method of treating skin comprises: (a) cleansing the skin with a daily cleansing mask; (b) topically applying a toner to skin; and (c) topically applying a composition to skin, wherein the composition comprises retinaldehyde, one or more skin conditioning agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. In some embodiments, the method of treating skin comprises: (a) cleansing the skin with a daily cleansing mask; (b) topically applying a toner to skin; and (c) topically applying a composition to skin, wherein the composition comprises retinaldehyde, one or more skin conditioning agents, and one or more calcium containing agents and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. In some embodiments, the method of treating skin comprises: (a) cleansing the skin with a daily cleansing mask; (b) topically applying a toner to skin; and (c) topically applying a composition to skin, wherein the composition comprises retinaldehyde, one or more peptides, one or more skin conditioning agents, and one or more calcium containing agents, and optionally, one or more additional retinoids, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof. In certain embodiments, the optional one or more additional retinoids is selected from the group consisting of retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, 2-(nicotinamido)-ethyl retinoate (NEAR-1), and derivatives and combinations thereof. In all forgoing embodiments, additional embodiments are described wherein the composition does not contain retinol. In certain embodiments, the one or more skin conditioning agents is selected from the group consisting of cyclopentasiloxane, dimethicone, polysilicone-11, ethylhexyl hydroxystearate, C12-15 alkyl benzoate, bis-ethylhexyl hydroxydimethoxy benzylmalonate, ethoxydiglycol, hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof. In certain embodiments, the optional one or more peptides is selected from the group consisting of palmitoyl hexapeptide-14, oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof. In certain embodiments, the optional one or more calcium containing agents is selected from the group consisting of hydroxyapatite, calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof.

As described herein, the method of treating skin may utilize skin compositions formulated to contain retinaldehyde in Hydroxysomes®. Hydroxysomes are designed to dermally deliver retinaldehyde with a continuous supply of calcium as nanoporous calcium phosphate particles. In some embodiments, the hydroxysomes is supplied by Laboratory Skin Care, Inc.

As described herein, the method of treating skin may utilize skin compositions described herein which are anhydrous, i.e. the composition does not contain water.

In some embodiments, the method of treating skin may utilize the topical skin composition which further comprises niacinamide, nicotinamide, vitamin B3, nicotinic acid, or niacin.

In preferred embodiments, the method of treating skin comprises: (a) cleansing the skin with a daily cleansing mask; (b) topically applying a toner to skin; and (c) topically applying a composition to skin, wherein the composition comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) cleansing the skin with a daily cleansing mask; (b) topically applying a toner to skin; and (c) topically applying a composition to skin, wherein the composition comprises retinaldehyde, dimethicone, isododecane, polysilicone-11, L-ascorbic acid, dimethyl isosorbide, and hydroxypinacolone retinoate, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In preferred embodiments, the method of treating skin comprises: (a) cleansing the skin with a daily cleansing mask; (b) topically applying a toner to skin; and (c) topically applying a composition to skin, wherein the composition comprises retinaldehyde, water, xanthan gum, glycerin, caprylic/Capric triglycerides, cetyl alcohol, stearyl alcohol, glyceryl stearate, PEG-100 stearate, dimethicone, polyacrylate-13, polyisobutene, polysorbate-20, phenoxyethanol, ethylhexylglycerin, and hydroxyapatite, wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof.

In some embodiments, the method of treating skin results in anti-acne, anti-aging, and skin lightening characteristics. In some embodiments, the method of treating skin improves skin firmness, measured by the fullness and plumpness of the skin. In some embodiments, the method of treating skin improves skin elasticity and resiliency, measured by the bounce-back of the skin. In some embodiments, the method of treating skin improves lines and wrinkles, measured by visible evaluation of the skin or replica analysis. In some embodiments, the method of treating skin refines skin texture, measured by smoother, softer and more even skin. In some embodiments, the method of treating skin improves dullness and provides a more even skin tone, measured as more radiant and luminous skin. In some embodiments, the method of treating skin provides in improvement in dyschromia, measured as a lightening of the skin. The improvement in the characteristics of the skin can be measured by ultrasound, measuring improvement in skin density. In some embodiments, the method of treating skin provides an improvement in mild to moderate acne vulgaris. The improvement is measured as reduction or elimination of the symptoms of acne including plugged pores, and outbreaks of inflamed lesions or pimples.

Kits

In embodiments described herein, the kit comprises a micro-exfoliation tool; a topical skin composition comprising: retinaldehyde, one or more skin conditioning agents, and optionally, one or more additional retinoids; and instructions for use. In embodiments described herein, the kit comprises a micro-exfoliation tool; a topical skin composition comprising: retinaldehyde, one or more skin conditioning agents, and one or more calcium containing agents, and optionally, one or more additional retinoids; and instructions for use. In embodiments described herein, the kit comprises a micro-exfoliation tool; a topical skin composition comprising: retinaldehyde, one or more peptides, one or more skin conditioning agents, and one or more calcium containing agents, and optionally, one or more additional retinoids; and instructions for use.

In embodiments described herein, the kit comprises a micro-dermabrasion paste, an exfoliating scrub, or other exfoliating tool; a topical skin composition comprising: retinaldehyde, one or more skin conditioning agents, and optionally, one or more additional retinoids; and instructions for use. In embodiments described herein, the kit comprises a micro-dermabrasion paste, an exfoliating scrub, or other exfoliating tool; a topical skin composition comprising: retinaldehyde, one or more skin conditioning agents, and one or more calcium containing agents, and optionally, one or more additional retinoids; and instructions for use. In embodiments described herein, the kit comprises a micro-dermabrasion paste, an exfoliating scrub, or other exfoliating tool; a topical skin composition comprising: retinaldehyde, one or more peptides, one or more skin conditioning agents, and one or more calcium containing agents, and optionally, one or more additional retinoids; and instructions for use.

In embodiments described herein, the kit comprises a daily cleansing mask; a topical toner; a topical skin composition comprising: retinaldehyde, one or more skin conditioning agents, and, optionally, one or more additional retinoids; and instructions for use. In embodiments described herein, the kit comprises a daily cleansing mask; a topical toner; a topical skin composition comprising: retinaldehyde, one or more skin conditioning agents, one or more calcium containing agents, and, optionally, one or more additional retinoids; and instructions for use. In embodiments described herein, the kit comprises a daily cleansing mask; a topical toner; a topical skin composition comprising: retinaldehyde, one or more peptides, one or more skin conditioning agents, one or more calcium containing agents, and, optionally, one or more additional retinoids; and instructions for use.

The micro-exfoliation tool of the present disclosure is designed to create micro pores, channels, or holes in the epidermis or outer layer of the skin. In some embodiments, the micro-exfoliation tool is a roller attached to a handle or wand, such as that shown in FIG. 1. FIG. 1 generally shows a micro-exfoliation tool 10. The micro-exfoliation tool 10 includes a handle or wand 12 and a head 14 attached to the handle 12. The head 14 includes a roller 16. In some embodiments, the head is configured as a stamp. The roller 16 is held in place by a mechanism of mounting the roller to the handle, such as a U-shaped collar 18 that is attached to the handle or wand 12 and engages the roller 16 at either end in such a way that allows the roller 16 to rotate. The roller 16 includes one or more needles 20. FIG. 1 shows the needles 20 in rows, but it is understood that the needles may be arranged in a variety of configurations. The micro-exfoliation tool 10 is preferably easily manufactured. In some embodiments, the handle 12, head 14, including the mechanism of mounting the roller to the handle or collar 18 and the roller 16 are injection molded plastic. The needles 20 are preferably stainless steel, and more preferably surgical grade stainless steel. In some embodiments, the one or more needles are made of other metals, such as bronze, platinum, gold, silver, or copper.

FIG. 2 shows a close up of the head 14, including the collar 18, roller 16, and needles 20. The needles 20 preferably form micro holes, pores, or channels in the epidermis of the skin. It is understood that other structures may be used instead of needles. When using needles, the needles are preferably solid and made of stainless steel, but can be made of other metals, such as bronze, platinum, gold, silver, or copper. The needles are preferably from about 0.1 mm to about 0.5 mm in length so that when the micro-exfoliation tool is placed on skin and rolled using moderate pressure, the needles penetrate only the epidermis, and not the deeper layers of skin. In some embodiments, the needles do not penetrate more than about 100 microns to 500 microns into the epidermis. The needles are from about 0.01 to about 0.5 mm in thickness.

In some embodiments, needles 20 are configured to transmit radio frequency (RF) or electrical stimulation through the needles. Not wishing to be bound by theory, radio frequency skin tightening is an aesthetic technique that uses RF energy to heat tissue and stimulate subdermal collagen production in order to reduce the appearance of fine lines and loose skin. The technique induces tissue remodeling and production of new collagen and elastin. Low-level electrical stimulation has been shown to increase muscle mass and muscle tone, and may be useful to stimulate collagen and elastin production, and improve facial contour. Additionally, electricity is used to physically enhance skin penetration of described compositions through high voltage, short duration pulses applied to the skin. In some embodiments, acupuncture needles 20 are configured to transmit heat. In some embodiments, acupuncture needles 20 are configured to transmit ultrasound.

In some embodiments, the head is configured as a stamp. The stamp can be pressed against the skin using moderate pressure. In some embodiments, the stamp is capable of vibrating.

As described herein, the topical skin composition of the kit comprises optionally one or more additional retinoids, wherein the optional one or more additional retinoids is selected from the group consisting of retinyl palmitate, alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, 2-(nicotinamido)-ethyl retinoate (NEAR-1), and derivatives and combinations thereof. In all forgoing embodiments, additional embodiments are described wherein the composition does not contain retinol. As described herein, the one or more skin conditioning agents is selected from the group consisting of cyclopentasiloxane, dimethicone, polysilicone-11, ethylhexyl hydroxystearate, C12-15 alkyl benzoate, bis-ethylhexyl hydroxydimethoxy benzylmalonate, ethoxydiglycol, hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof. As described herein, the optional one or more peptides is selected from the group consisting of palmitoyl hexapeptide-14, oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof. As described herein, the optional one or more calcium containing agents is selected from the group consisting of hydroxyapatite, calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof.

As described herein, the topical skin composition of the kit may utilize skin compositions formulated to contain retinaldehyde in Hydroxysomes®. Hydroxysomes are designed to dermally deliver retinaldehyde with a continuous supply of calcium as nanoporous calcium phosphate particles. In some embodiments, the hydroxysomes is supplied by Laboratory Skin Care, Inc.

As described herein, the topical skin composition of the kit may utilize skin compositions described herein which are anhydrous, i.e. the composition does not contain water.

In some embodiments, the topical skin composition of the kit may further comprise niacinamide, nicotinamide, vitamin B3, nicotinic acid, or niacin.

In preferred embodiments, the topical skin composition of the kit comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol.

In preferred embodiments, the topical skin composition of the kit comprises retinaldehyde, dimethicone, isododecane, polysilicone-11, L-ascorbic acid, dimethyl isosorbide, and hydroxypinacolone retinoate.

In preferred embodiments, the topical skin composition of the kit comprises retinaldehyde, water, xanthan gum, glycerin, caprylic/Capric triglycerides, cetyl alcohol, stearyl alcohol, glyceryl stearate, PEG-100 stearate, dimethicone, polyacrylate-13, polyisobutene, polysorbate-20, phenoxyethanol, ethylhexylglycerin, and hydroxyapatite.

As described herein, the active ingredients of the skin compositions include, but are not limited to, retinaldehyde, the retinoids, the peptides, the calcium containing agents, and the skin conditioning agents. It is also known in the art that the active ingredients may be contained in such compositions with cosmetically and/or pharmaceutically acceptable secondary agents, such as diluents, fillers, disintegrants, binders, lubricants, surfactants, hydrophobic vehicles, water-soluble vehicles, emulsifiers, buffers, humectants, moisturizers, solubilizers, preservatives and the like. The means and methods for administration are known in the art and an artisan can refer to various pharmacologic references for guidance. For example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980) can be consulted.

The skin compositions described herein may be prepared, packaged, or sold in bulk as a single unit dose or as multiple unit doses and may be administered in the conventional manner by any route where they are active. In preferred embodiments, the topical skin composition is provided in a capsule. Additionally, the skin compositions disclosed herein may be delivered by using any such route of administration for all of the dosage regimens described herein. The compositions and amounts of non-active ingredients in such a composition may depend on the amount of the active ingredient. Such parameters may be readily appreciated and understood by one of skill in the art.

In certain embodiments, the kit further contains one or more skin agents, wherein the one or more skin agents are selected from the group consisting of a cleanser, a toner, a moisturizer and any combination thereof.

In some embodiments, the instructions for use of the kit comprises language similar to the following: (a) Roll: Divide face into sections (forehead, right side, left side, chin and neck). With moderate and comfortable pressure, roll or press the micro-exfoliating tool over each section 4-10 time, changing directions with each pass as illustrated below. Be sure to lift and re-apply roller when changing directions; do not pivot when roller is in contact with skin. (b) Apply composition: Pinch and twist off tail end of one skin composition capsule and apply contents to face and neck area. In some embodiments, the instructions for use of the kit further comprises (c) Apply an additional composition to the skin of the face and neck area.

In some embodiments, the instructions for use of the kit comprises language similar to the following: (a) Cleanse face using daily cleansing mask. (b) Apply topical toner to skin, do not rinse off. (c) Apply topical skin composition to skin.

In some embodiments, the method for treating skin comprises (a) rolling the skin with a micro-exfoliation tool, wherein the micro-exfoliating tool comprises a handle and a head, the head comprising a roller, a mechanism of mounting the roller to the handle, and one or more needles fixed to the roller; and (b) topically applying a composition to skin. In some embodiments, the composition comprises skin lightening agents such as hydroquinone. In some embodiments, the composition comprises anti-inflammatory compounds such as corticosteroids. In some embodiments, the composition comprises antifungals or anti-bacterial agents. In some embodiments, the composition comprises agents to control rosacea such as metronidazole. In some embodiments, the composition comprises small proteins, peptides and neuropeptides >500 Daltons such as Botox or onabotullinumtoxin A. In some embodiments, the composition comprises pain agents such as aspirin or ibuprofen.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

EXAMPLES

Example 1: Intensive Renewing Serum Formulation

The concentration of each component of an exemplary topical skin composition, referred to as Intensive Renewing Serum (IRS), can be found in Table 1.

TABLE 1

Intensive Renewing Serum (IRS)

| INCI | Concentration Range | Concentration |
|---|---|---|
| Cyclopentasiloxane | 50%-75.0% | 65.720% w/w |
| Dimethicone | 15%-20.0% | 16.776% w/w |
| Polysilicone-11 | 10%-15.0% | 11.842% w/w |
| Ethylhexyl Hydroxystearate | 1%-5.0% | 2.467% w/w |
| C12-15 Alkyl Benzoate | 1%-5.0% | 1.480% w/w |
| Retinal/Retinaldehyde | 0.1%-1.0% | 0.458% w/w |
| Palmitoyl Hexapeptide-14 | 0.00001%-0.099% | 0.0009868% w/w |
| Retinyl Palmitate | 0.1%-1.0% | 0.59% w/w |
| Bis-Ethylhexyl Hydroxydimethoxy Benzylmalonate | 0.1%-1.0% | 0.2% w/w |
| Hydroxyapatite | 0.00001%-0.099% | 0.0716% w/w |
| Ethoxydiglycol | 0.1%-1.0% | 0.3947% w/w |

Example 2: Clinical Study of Efficacy and Tolerance of IRS Regimen on Wrinkles and Skin Texture A 12 week double-blind clinical trial was performed to assess the efficacy and tolerance of Intensive Renewing Serum (IRS)+REDEFINE Regimen+micro-exfoliation tool when used by women with moderate crow's feet lines and wrinkles, and moderate rough texture. The subjects of the study included: n=23 females, ages 35-65, FP I-III, with moderate (score of 4-6 on modified Griffiths' scale) crow's feet lines and wrinkles and rough texture.

The REDEFINE Regimen includes: A) REDEFINE DAILY CLEANSING MASK (Water/Aqua/Eau, Kaolin, Butylene Glycol, Isododecane, Titanium Dioxide (CI 77891), Lauryl Methacrylate/Glycol Dimethacrylate Crosspolymer, Stearic Acid, Cetyl Alcohol, Bentonite, Dimethicone, Glyceryl Stearate, Hydrogenated Lecithin, Magnesium Aluminum Silicate, Oleth-10 Phosphate, PEG-100 Stearate, Sodium Lactate, Sorbitan Stearate, Tocopheryl Acetate, Xanthan Gum, Fragrance/Parfum, Potassium Hydroxide, Disodium EDTA, Hexylene Glycol, Ethylhexylglycerin, Caprylyl Glycol, Phenoxyethanol.) B) REDEFINE PORE MINIMIZING TONER (Water/Aqua/Eau, Butylene Glycol, Gluconolactone, Lactobionic Acid, Dimethyl MEA, *Lens esculenta* (Lentil) Seed Extract, Sodium Hyaluronate, *Glycyrrhiza glabra* (Licorice) Root Extract, *Panax ginseng* Root Extract, Carrageenan, PEG-40 Hydrogenated Castor Oil, Polysorbate 20, Octoxynol-12, Fragrance/Parfum, Citric Acid, Ammonium Hydroxide, Caprylyl Glycol, Ethylhexylglycerin, Potassium Sorbate, Chlorphenesin, Phenoxyethanol.) C) REDEFINE TRIPLE DEFENSE TREATMENT SPF 30 (ACTIVE INGREDIENTS: Avobenzone 3% Homosalate 2.5% Octisalate 5% Octocrylene 2.7%; INACTIVE INGREDIENTS: Water/Aqua/Eau, Isododecane, Ethylhexyl Palmitate, Polymethylsilsesquioxane, Glycerin, Dimethicone, Cetyl Alcohol, Glyceryl Stearate, PEG-1000 Stearate, Silica, Tetrapeptide-21, *Dunaliella salina* Extract, Hydrolyzed Silk, Resveratrol, Sodium Hyaluronate, Humic Acids, *Olea europaea* (Olive) Fruit Extract, *Camellia oleifera* Leaf Extract, Talc, Sucrose Stearate, Polyurethane-40, Polysorbate 20, Polyisobutene, Polyacrylate-13, PEG-12 Dimethicone, Hydrogenated Polydecene, Fragrance/Parfum, Sorbitan Isostearate, Butylene Glycol, Caprylyl Glycol, Chlorphenesin, Phenoxyethanol, Methylparaben, Butylparaben, Ethylparaben, Propylparaben, Isobutylparaben, Iron Oxides.) D) REDEFINE OVERNIGHT RESTORATIVE CREAM (Water/Aqua/Eau, Isododecane, Butylene Glycol, Glycerin, Caprylic/Capric/Myristic/Stearic Triglyceride, Niacinamide, Beeswax/Cera Alba/Cire d'abeille, Cetearyl Alcohol, Gluconolactone, Dimethicone, Glyceryl Stearate, PEG-100 Stearate, Squalane, Tetrapeptide-21, Ascorbic Acid, Hydrolyzed Sericin, Hydrolyzed Silk, *Olea europaea* (Olive) Fruit Extract, Retinyl Palmitate, Sodium Hyaluronate, Soy Isoflavones, Tocopheryl Acetate, Humic Acids, Ammonium Acryloyldimethyltaurate/VP Copolymer, Caprylic/Capric Triglyceride, Cholesterol, Fragrance/Parfum, Phospholipids, Polyacrylate-13, Polyisobutene, Polymethyl Methacrylate, Polysilicone-11, Polysorbate 20, Sucrose Stearate, Sorbitan Isostearate, Hexylene Glycol, Caprylyl Glycol, Potassium Sorbate, Chlorphenesin, Phenoxyethanol, Titanium Dioxide.)

Table 2 provides the subject rating of particular skin attributes at weeks 4 and 8 after treatment with the REDFINE Regimen, rolling with the micro-exfoliation tool, and treatment with IRS.

TABLE 2

Percentage of subjects noticing improvement.

| Skin Attributes | Week 4 | Week 8 |
|---|---|---|
| Skin Firmness | 91% | 91% |
| Appearance of fine lines/wrinkles | 78% | 91% |
| Skin tone evenness | 87% | 91% |
| Skin radiance/luminosity/glow | 96% | 91% |
| Skin plumpness | 83% | 91% |
| Skin Softness | 87% | 87% |
| Skin Texture | 83% | 78% |

Surprisingly, when the topical skin composition containing retinol (Night Renewing Serum, NRS) was compared with the topical skin composition of the present application (IRS, containing retinaldehyde) it was noticed that subjects experienced results faster with the IRS composition. Table 3 provides the comparison data, which presents the results at week 4 for the subjects treated with the REDFINE Regimen, rolling with the micro-exfoliation tool, and treatment with IRS versus week 8 for the subjects treated with the REDFINE Regimen, rolling with the micro-exfoliation tool, and treatment with NRS.

TABLE 3

Percentage of subjects noticing improvement.

| Skin Attributes | Week 4, IRS treatment | Week 8, NRS treatment |
|---|---|---|
| Skin radiance/luminosity/glow | 96% | 57% |
| Appearance of fine lines/wrinkles | 78% | 40% |
| Skin Softness | 87% | 50% |
| Skin tone evenness | 87% | 53% |
| Skin Texture | 78% | 57% |

The clinical grading results of the clinical trial are provided in Table 4 at weeks 4 and 8 after treatment with the REDFINE Regimen, rolling with the micro-exfoliation tool, and treatment with IRS.

TABLE 4

Percentage of subjects showing improvement.

| Skin Attributes | Week 4 | Week 8 |
|---|---|---|
| Plumpness | 65% | 96% |
| Skin smoothness/roughness (tactile) | 83% | 91% |
| Softness (tactile) | 78% | 87% |
| Skin elasticity/resiliency/bounce back ('pinch recoil') | 78% | 83% |

TABLE 4-continued

Percentage of subjects showing improvement.

| Skin Attributes | Week 4 | Week 8 |
|---|---|---|
| Skin Texture (visual) | 39% | 83% |
| Fine lines (crow's feet) | 70% | 83% |
| Skin radiance/luminosity/brightness | 35% | 78% |
| Fine lines (global face) | 57% | 78% |
| Firmness (tactile) | 30% | 74% |
| Wrinkles (crow's feet) | 26% | 61% |
| Wrinkles (global face) | 13% | 57% |
| Skin tone evenness | 22% | 52% |

The clinical grading results of the clinical trial showing the comparison with the topical skin composition containing retinol (NRS) and the topical skin composition of the present application (IRS, containing retinaldehyde) are provided in Table 5 at week 4 for the subjects treated with the REDFINE Regimen, rolling with the micro-exfoliation tool, and treatment with IRS versus week 8 for the subjects treated with the REDFINE Regimen, rolling with the micro-exfoliation tool, and treatment with NRS.

TABLE 5

Percentage of subjects showing improvement.

| Skin Attributes | Week 4, IRS treatment | Week 8, IRS treatment | Week 8, NRS treatment |
|---|---|---|---|
| Fine lines (global face) | 57% | 78% | 37% |
| Wrinkles (global face) | 13% | 57% | 10% |
| Skin tone evenness | 22% | 52% | 37% |

Figure 3A:
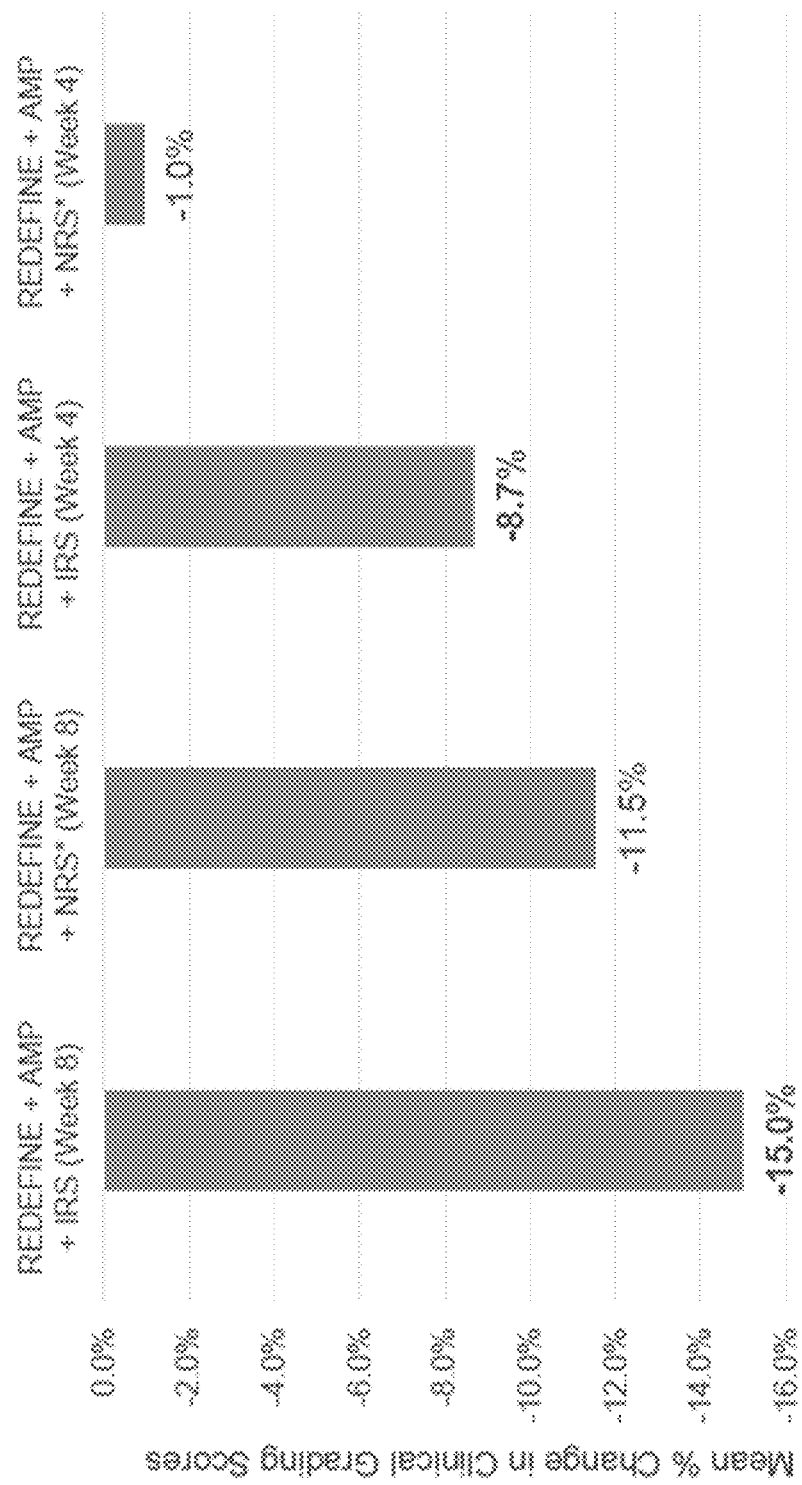
FIG. 3A depicts the mean change in clinical grading score for fine lines (global face).
Figure 3B:
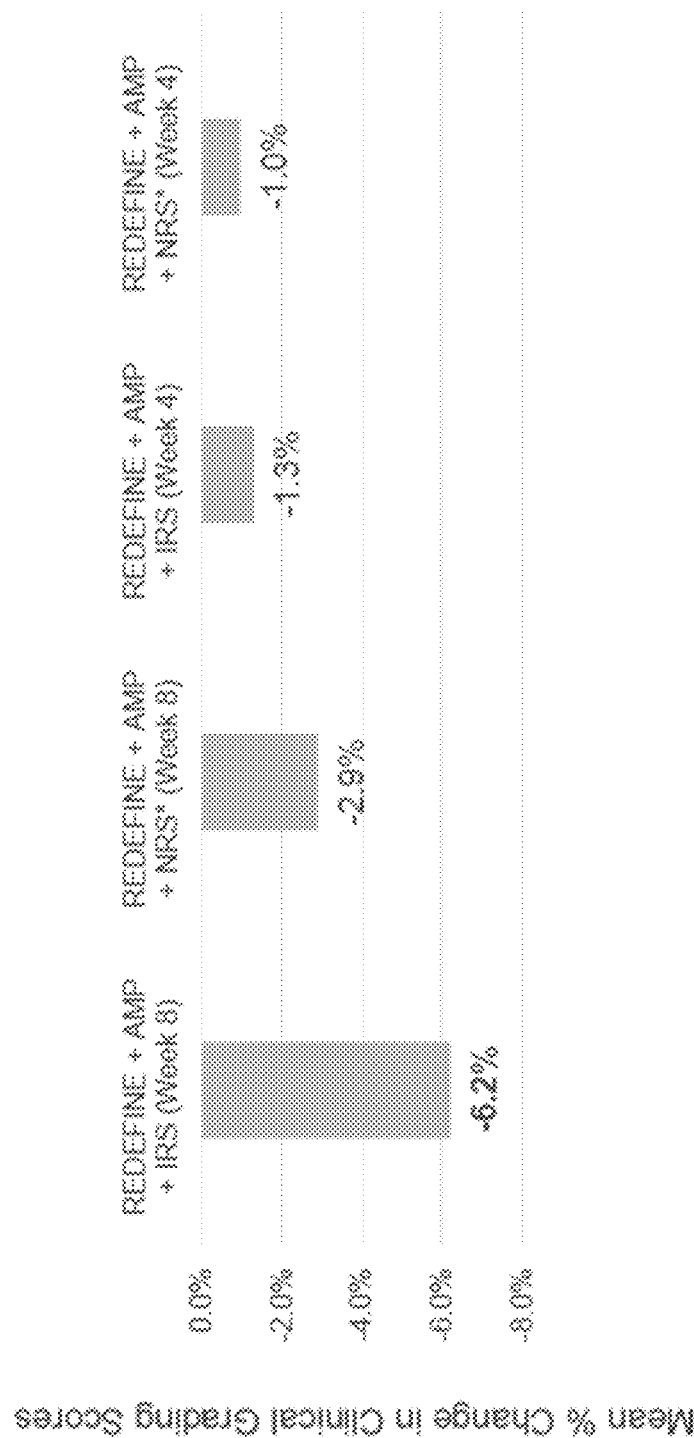
FIG. 3B depicts the mean change in clinical grading score for wrinkles (global face).

The mean change in clinical grading score for fine lines (global face) is provided in FIG. 3A, and wrinkles (global face) is provided in FIG. 3B.

Subjects showed a 74% improvement in skin density measured by ultrasound after 8 weeks of treatment with the REDFINE Regimen, rolling with the micro-exfoliation tool, and treatment with IRS. Table 6 provides the mean ultrasound measurement and change from baseline at weeks 4 and 8.

TABLE 6

Mean Ultrasound Measurement and Change From Baseline.

| Baseline: | Week 4 | Week 8 |
|---|---|---|
| 29.31 | 32.40 | 33.84 |
| Change from BL | Increase 11% | Increase 16% |

Table 7 provides the objective (clinical) assessment of tolerability, all results at weeks 1, 4, and 8 fall into the very mild or mild category and is considered tolerable.

TABLE 7

Percentage of Subjects with Skin Ailment Compared to Baseline.

| Skin Ailment | Week 1 | Week 4 | Week 8 |
|---|---|---|---|
| Erythema | 4% | 13% | 4% |
| Burning | 0% | 0% | 0% |
| Edema | 0% | 0% | 0% |
| Stinging | 4% | 0% | 0% |
| Dryness | 9% | 0% | 4% |
| Tightness | 4% | 0% | 4% |
| Itching | 0% | 0% | 0% |

Example 3: Clinical Study of Efficacy and Tolerance of IRS Regimen on Dyschromia, Dullness and Wrinkles A 12 week double-blind clinical trial was performed to assess the efficacy and tolerance of Intensive Renewing Serum (IRS)+REVERSE Regimen+micro-exfoliation tool when used by women with moderate dyschromia on the face, mild to moderate dullness and global face lines and wrinkles. The subjects included: n=19 females, ages 35-65, FP I-IV (at least 60% FP I-III), with moderate (score of 4-6 on modified Griffiths' scale) dyschromia, 40-60% with moderate discrete HP (age spots), 10-20% with melisma (as confirmed by Woods lamp), and with mild to moderate (3-6 on modified Griffiths' scale) dullness and global face lines/wrinkles.

The REVERSE Regimen includes: A) REVERSE DEEP EXFOLIATING WASH (Water/Aqua/Eau, C12-15 Alkyl Benzoate, Diethylhexyl Sebacate, Polylactic Acid, Cetearyl Alcohol, Jojoba Esters, PEG-40 Stearate, Glyceryl Stearate, Ammonium Laureth Sulfate, Magnesium Aluminum Silicate, Pentylene Glycol, Potassium Cetyl Phosphate, Ceteareth-20, Hydroxyacetophenone, Lactic Acid, *Mentha piperita* (Peppermint) Oil, Fragrance/Parfum, Xanthan Gum, Glycolic Acid, Sodium Magnesium Silicate, Propylene Glycol, Citric Acid, Phenoxyethanol, Potassium Sorbate, Hydroxyisohexyl 3-Cyclohexene Carboxaldehyde, Limonene, Linalool, Yellow 5 (CI 19140), Yellow 6.) B) REVERSE INTENSIVE BRIGHTENING TONER (Water/Aqua/Eau, *Hamamelis virginiana* (Witch Hazel) Water, Butylene Glycol, Polysorbate 20, Ethoxydiglycol, Alcohol, Kojic Acid, Dipotassium Glycyrrhizate, *Glycyrrhiza glabra* (Licorice) Root Extract, Salicylic Acid, Phenylethyl Resorcinol, Tocopherol, Alanine, Glycine, Isoleucine, Leucine, Fragrance/Parfum, Sodium Sulfite, PEG-12 Dimethicone, Sodium Metabisulfite, Sodium Hydroxide, Citric Acid, Disodium EDTA, Caprylyl Glycol, Chlorphenesin, Phenoxyethanol, Citral, Hydroxyisohexyl 3-Cyclohexene Carboxaldehyde, Limonene, Linalool.) C) REVERSE DUAL ACTIVE BRIGHTENING COMPLEX (Vitamin C Formula: Isododecane, Cyclopentasiloxane, Cyclohexasiloxane, Dimethicone/Bis-Isobutyl PPG-20 Crosspolymer, Ethoxydiglycol, Ascorbic Acid, Caprylic/Capric Triglyceride, Kojic Acid, Ethylhexyl Hydroxystearate, Polysilicone-11, *Syringa vulgaris* (Lilac) Leaf Cell Culture Extract, Maltodextrin. Retinol Formula: Water/Aqua/Eau, Caprylic/Capric Triglyceride, *Butyrospermum parkii* (Shea) Butter, Glycerin, Glyceryl Stearate, Ethoxydiglycol, Butylene Glycol, *Carthamus tinctorius* (Safflower) Seed Oil, Stearic Acid, Polysorbate 60, Stearyl Alcohol, Cyclopentasiloxane, Cyclohexasiloxane, Retinol, Dipotassium Glycyrrhizate, *Glycyrrhiza glabra* (Licorice) Root Extract, Sodium Hyaluronate, Sorbitol, Tocopheryl Acetate, Fragrance/Parfum, Polysorbate 20, Carbomer, Triethanolamine, Glyceryl Acrylate/Acrylic Acid Copolymer, Caprylyl Glycol, Hexylene Glycol, Ethylhexylglycerin, BHT, Citric Acid, Disodium EDTA, Phenoxyethanol, Methylparaben, Propylparaben, Citral, Hydroxyisohexyl 3-Cyclohexene Carboxaldehyde, Limonene, Linalool, Yellow 5.)

Table 8 provides the subject rating of particular skin attributes at weeks 4 and 8 after treatment with the REVERSE Regimen, rolling with the micro-exfoliation tool, and treatment with IRS.

TABLE 8

Percentage of subjects noticing improvement.

| Skin Attributes | Week 4 | Week 8 |
| --- | --- | --- |
| Appearance of fine lines/wrinkles | 90% | 95% |
| Skin radiance/luminosity/glow | 84% | 84% |
| Skin tone evenness | 84% | 84% |
| Skin Softness | 84% | 84% |
| Skin plumpness | 79% | 84% |
| Skin Firmness | 79% | 79% |
| Skin Texture | 84% | 79% |

The clinical grading results of the clinical trial are provided in Table 9 at weeks 4 and 8 after treatment with the REVERSE Regimen, rolling with the micro-exfoliation tool, and treatment with IRS.

TABLE 9

Percentage of subjects showing improvement.

| Skin Attributes | Week 4 | Week 8 |
| --- | --- | --- |
| Skin elasticity/resiliency/bounce back ('pinch recoil') | 95% | 95% |
| Fine lines (crow's feet) | 84% | 95% |
| Skin smoothness/roughness (tactile) | 90% | 90% |
| Fine lines (global face) | 53% | 84% |
| Softness (tactile) | 79% | 84% |
| Firmness (tactile) | 26% | 79% |
| Plumpness | 63% | 79% |
| Skin Texture (visual) | 53% | 74% |
| Skin radiance/luminosity/brightness | 53% | 68% |
| Wrinkles (crow's feet) | 37% | 63% |
| Skin tone evenness | 26% | 58% |
| Wrinkles (global face) | 5% | 26% |

Subjects showed a 78% improvement in skin firmness measured by $R_0$ (extensibility) after 8 weeks of treatment with the REVERSE Regimen, rolling with the micro-exfoliation tool, and treatment with IRS. A decrease in $R_0$ (extensibility) correlates to improvement in skin firmness. Table 10 provides the percentage of subjects showing improvement in $R_0$ and change from baseline at weeks 4 and 8.

TABLE 10

Percent Improvement in $R_0$ and Change From Baseline.

| | Week 4 | Week 8 |
| --- | --- | --- |
| Change from BL | 37%<br>Increase 7% | 78%<br>Decrease 21% |

Table 11 provides the objective (clinical) assessment of tolerability, all results at weeks 1, 4, and 8 fall into the very mild or mild category and is considered tolerable.

TABLE 11

Percentage of Subjects with Skin Ailment Compared to Baseline.

| Skin Ailment | Week 1 | Week 4 | Week 8 |
| --- | --- | --- | --- |
| Dryness | 11% | 16% | 5% |
| Erythema | 5% | 11% | 0% |
| Burning | 0% | 11% | 5% |
| Tightness | 0% | 11% | 5% |
| Stinging | 0% | 5% | 5% |
| Itching | 0% | 5% | 0% |
| Edema | 0% | 0% | 0% |

Example 4: Clinical Study of Efficacy and Tolerance of IRS Regimen on Dyschromia, Dullness and Wrinkles A 12 week double-blind clinical trial was performed to assess the efficacy and tolerance of Intensive Renewing Serum (IRS)+REVERSE Lightening (HQ) Regimen when used by women with moderate dyschromia on the face, mild to moderate dullness and global face lines and wrinkles. The subjects included: n=20 females, ages 35-65, FP I-IV (at least 60% FP I-III), with moderate (score of 4-6 on modified Griffiths' scale) dyschromia, 40-60% with moderate discrete HP (age spots), 10-20% with melisma (as confirmed by Woods lamp), and with mild to moderate (3-6 on modified Griffiths' scale) dullness and global face lines/wrinkles.

The REVERSE Lightening (HQ) Regimen includes: A) REVERSE SKIN LIGHTENING TONER (ACTIVE INGREDIENT: Hydroquinone 2%; INACTIVE INGREDIENTS: Water/Aqua/Eau, Ethoxydiglycol, *Hamamelis virginiana* (Witch Hazel) Water, Methylpropanediol, Alcohol, Polysorbate 20, Kojic Acid, Salicylic Acid, Magnesium Ascorbyl Phosphate, *Arctostaphylos uva ursi* Leaf Extract, *Arnica montana* Flower Extract, *Citrus limon* (Lemon) Peel Extract, *Foeniculum vulgare* (Fennel) Fruit Extract, Sodium Sulfite, Fragrance/Parfum, PEG-12 Dimethicone, Zinc Phenolsulfonate, Citric Acid, Sodium Metabisulfite, Sodium Hydroxide, Propylene Glycol, Phenoxyethanol, Chlorphenesin, DMDM Hydantoin, Benzoic Acid, Sorbic Acid, Hydroxyisohexyl 3-Cyclohexene Carboxaldehyde, Limonene, Linalool, Yellow 5, Yellow 6.) B) REVERSE SKIN LIGHTENING TREATMENT (ACTIVE INGREDIENT: Hydroquinone 2%; INACTIVE INGREDIENTS: Water/Aqua/Eau, Ethoxydiglycol, Cetearyl Alcohol, PPG-12/SMDI Copolymer, Diethylhexyl Sebacate, Polyacrylamide, Ceteareth-20, Glycerin, C13-14 Isoparaffin, Dimethicone, Fragrance/Parfum, Retinol, Ascorbyl Palmitate, Magnesium Ascorbyl Phosphate, Lactic Acid, *Arctostaphylos uva ursi* Leaf Extract, Sodium C14-16 Olefin Sulfonate, Sodium Metabisulfite, Laureth-7, Glyceryl Stearate, PEG-100 Stearate, Tocopheryl Acetate, Citric Acid, *Glycine soja* (Soybean) Oil, Propylene Glycol, Disodium EDTA, BHT, Methylparaben, Propylparaben, Benzoic Acid, Sorbic Acid, Chlorphenesin, Imidazolidinyl Urea, Phenoxyethanol, Hydroxyisohexyl 3-Cyclohexene Carboxaldehyde, Limonene, Linalool, Yellow 5, Yellow 6.)

Table 12 provides the subject rating of particular skin attributes at weeks 4 and 8 after treatment with the HQ Regimen and treatment with IRS.

TABLE 12

Percentage of subjects noticing improvement.

| Skin Attributes | Week 4 | Week 8 |
| --- | --- | --- |
| Skin radiance/luminosity/glow | 75% | 95% |
| Skin tone evenness | 80% | 90% |
| Skin Firmness | 75% | 90% |
| Skin Texture | 75% | 90% |
| Skin plumpness | 75% | 90% |

TABLE 12-continued

Percentage of subjects noticing improvement.

| Skin Attributes | Week 4 | Week 8 |
|---|---|---|
| Skin Softness | 80% | 85% |
| Appearance of fine lines/wrinkles | 60% | 80% |

The clinical grading results of the clinical trial are provided in Table 13 at weeks 4 and 8 after treatment with the HQ Regimen and treatment with IRS.

TABLE 13

Percentage of subjects showing improvement.

| Skin Attributes | Week 4 | Week 8 |
|---|---|---|
| Skin smoothness/roughness (tactile) | 95% | 95% |
| Softness (tactile) | 85% | 95% |
| Fine lines (global face) | 65% | 95% |
| Fine lines (crow's feet) | 65% | 90% |
| Skin elasticity/resiliency/bounce back ('pinch recoil') | 70% | 85% |
| Plumpness | 60% | 85% |
| Skin Texture (visual) | 40% | 85% |
| Skin radiance/luminosity/brightness | 40% | 75% |
| Firmness (tactile) | 35% | 70% |
| Skin tone evenness | 25% | 70% |
| Wrinkles (global face) | 30% | 50% |
| Wrinkles (crow's feet) | 15% | 35% |

Subjects showed a 74% improvement in skin firmness measured by $R_0$ (extensibility) after 8 weeks of treatment with the HQ Regimen and treatment with IRS. A decrease in $R_0$ (extensibility) correlates to improvement in skin firmness. Table 14 provides the percentage of subjects showing improvement in $R_0$ and change from baseline at weeks 4 and 8.

TABLE 14

Percent Improvement in $R_0$ and Change From Baseline.

| | Week 4 | Week 8 |
|---|---|---|
| Change from BL | 30% Increase 17% | 74% Decrease 14% |

Table 15 provides the objective (clinical) assessment of tolerability, all results at weeks 1, 4, and 8 fall into the very mild or mild category and is considered tolerable.

TABLE 15

Percentage of Subjects with Skin Ailment Compared to Baseline.

| Skin Ailment | Week 1 | Week 4 | Week 8 |
|---|---|---|---|
| Erythema | 5% | 25% | 10% |
| Dryness | 20% | 20% | 10% |
| Burning | 5% | 10% | 5% |
| Tightness | 15% | 10% | 5% |
| Stinging | 0% | 5% | 5% |
| Itching | 5% | 5% | 0% |
| Edema | 5% | 0% | 0% |

Example 5: Clinical Study of Efficacy and Tolerance of IRS Regimen on Wrinkles

A 14 week double-blind clinical trial was performed to assess the efficacy and tolerance of Intensive Renewing Serum (IRS)+SOOTHE Regimen when used by women with moderate lines and wrinkles at crow's feet and under eye areas, some having mild to moderate redness and some having self-perceived reactive and sensitive skin. The subjects included: n=24 females, ages 35-65, FP I-IV, with mild to moderate (score of 3-6 on modified Griffiths' scale) lines and wrinkles in the crow's feet area and under eye area, approximately 60% with mild to moderate (score of 3-6 on modified Griffiths' scale) redness on the global face, approximately. 40% with reactive and sensitive skin as determined by 4 Cosmetic Intolerance Screener questions. Subjects used the SOOTHE Regimen only for weeks 1 and 2, starting in week 3 the subjects also treated skin with IRS.

The SOOTHE Regimen includes: A) SOOTHE GENTLE CREAM WASH (Water/Aqua/Eau, Caprylic/Capric Triglyceride, Glycerin, Cyclopentasiloxane, Propanediol, Isostearyl Alcohol, *Aloe barbadensis* Leaf Juice, Ceramide NP, Ceramide EOP, Ceramide AP, Caffeine, Tocopheryl Acetate, Bisabolol, Butylene Glycol Cocoate, Acrylates/C10-30 Alkyl Acrylate Crosspolymer, Xanthan Gum, Ethylcellulose, Aminomethyl Propanol, Sodium Lauroyl Lactylate, Tropolone, Phytosphingosine, Cholesterol, Carbomer, 1,2-Hexanediol, Caprylyl Glycol, Potassium Sorbate, Sodium Benzoate, Ethylhexylglycerin, Phenoxyethanol.) B) SOOTHE SENSITIVE SKIN TREATMENT (ACTIVE INGREDIENTS: Allantoin 0.5%, Dimethicone 2.9%; INACTIVE INGREDIENTS: Water/Aqua/Eau, Glycerin, Isododecane, Sodium Acrylates Copolymer, *Oryza sativa* (Rice) Bran Extract, *Chamomilla recutita* (*Matricaria*) Flower Extract, *Pelargonium graveolens* Flower Oil, *Lavandula angustifolia* (Lavender) Oil, *Boswellia serrata* Extract, Oligopeptide-10, Tetrapeptide-16, Tocopherol, Tropolone, Tranexamic Acid, Honey Extract, *Glycine soja* (Soybean) Germ Extract, *Perilla ocymoides* Seed Oil, *Helianthus annuus* (Sunflower) Seed Oil, Bisabolol, *Angelica polymorpha sinensis* Root Extract, Linoleic Acid, Linolenic Acid, Butylene Glycol, Coco-Caprylate/Caprate, Decyl Glucoside, Dimethylacrylamide/Acrylic Acid/Polystyrene Ethyl Methacrylate Copolymer, Hydrogenated Polyisobutene, Lysolecithin, PEG-40 Stearate, Phospholipids, Polyglyceryl-10 Stearate, Polysilicone-11, Xanthan Gum, Hexylene Glycol, Tin Oxide, 1,2-Hexanediol, Caprylyl Glycol, Chlorhexidine Digluconate, Chlorphenesin, Phenoxyethanol, Potassium Sorbate, Sodium Benzoate, Citronellol, Geraniol, Linalool, Mica, Titanium Dioxide.) C) SOOTHE MOISTURE REPLENISHING CREAM (Water/Aqua/Eau, Dimethicone, Glycerin, Pentylene Glycol, Ammonium Acryloyldimethyltaurate/VP Copolymer, *Echium plantagineum* Seed Oil, *Chamomilla recutita* (*Matricaria*) Flower Extract, *Olea europaea* (Olive) Fruit Oil, *Vitis vinifera* (Grape) Seed Oil, *Pichia anomala* Extract, Ascorbyl Palmitate, Tocopherol, Triacetin, Hydrogenated Lecithin, Carnitine, Canola Oil/ Huile de colza, Urea, Lecithin, Carbomer, Dimethicone/ Vinyl Dimethicone Crosspolymer, Glyceryl Oleate, Glyceryl Stearate, Polysilicone-1, Sodium Hydroxide, Xanthan Gum, Citric Acid, BHT, Ethylhexylglycerin, Potassium Sorbate, Sodium Benzoate, Benzyl Alcohol, Phenoxyethanol.)

Table 16 provides the subject rating of particular skin attributes at weeks 6 and 10 after treatment with the SOOTHE Regimen and treatment with IRS.

TABLE 16

Percentage of subjects noticing improvement from week 2.

| Skin Attributes | Week 6 | Week 10 |
|---|---|---|
| Appearance of fine lines/wrinkles | 67% | 88% |
| Skin plumpness | 63% | 88% |
| Skin Firmness | 71% | 75% |

TABLE 16-continued

Percentage of subjects noticing improvement from week 2.

| Skin Attributes | Week 6 | Week 10 |
| --- | --- | --- |
| Skin tone evenness | 67% | 75% |
| Skin Softness | 63% | 75% |
| Skin radiance/luminosity/glow | 67% | 71% |
| Skin Texture | 63% | 63% |

The clinical grading results of the clinical trial are provided in Table 17 at weeks 6 and 10 after treatment with the SOOTHE Regimen and treatment with IRS.

TABLE 17

Percentage of subjects showing improvement.

| Skin Attributes | Week 6 | Week 10 |
| --- | --- | --- |
| Fine lines (under eye) | 79% | 100% |
| Softness (tactile) | 83% | 100% |
| Skin elasticity/resiliency/bounce back ('pinch recoil') | 92% | 92% |
| Fine lines (global face) | 67% | 92% |
| Wrinkles (crow's feet) | 42% | 92% |
| Fine lines (crow's feet) | 63% | 92% |
| Skin smoothness/roughness (tactile) | 83% | 92% |
| Plumpness | 63% | 92% |
| Skin radiance/luminosity/brightness | 75% | 88% |
| Evenness of skin tone (redness) | 58% | 83% |
| Skin Texture (visual) | 50% | 75% |
| Wrinkles (under eye) | 42% | 71% |
| Firmness (tactile) | 46% | 67% |
| Wrinkles (global face) | 21% | 67% |

Subjects showed a 73% improvement in skin firmness measured by $R_0$ (extensibility) after 10 weeks of treatment with the SOOTHE Regimen and treatment with IRS. A decrease in $R_0$ (extensibility) correlates to improvement in skin firmness. Table 18 provides the percentage of subjects showing improvement in $R_0$ and change from baseline at weeks 6 and 10.

TABLE 18

Percent Improvement in $R_0$ and Change From Baseline.

| | Week 6 | Week 10 |
| --- | --- | --- |
| Change from BL | 46%<br>Decrease 1% | 73%<br>Decrease 30% |

Table 19 provides the objective (clinical) assessment of tolerability, nearly all results at weeks 2, 4, and 6 fall into the very mild or mild category and is considered tolerable, the only exception was for erythema at week 6 which falls into the moderate category but is still considered tolerable. No irritation was observed at week 10.

TABLE 19

Percentage of Subjects with Skin Ailment Compared to Baseline.

| Skin Ailment | Week 2 | Week 4 | Week 6 |
| --- | --- | --- | --- |
| Scaling/peeling | 4% | 8% | 8% |
| Erythema | 0% | 0% | 4% |
| Irritant folliculitis | 0% | 0% | 0% |
| Burning | 0% | 0% | 0% |
| Edema | 0% | 0% | 5% |
| Stinging | 0% | 0% | 0% |
| Itching | 0% | 0% | 0% |

Example 6: Clinical Study of Efficacy and Tolerance of IRS Regimen on Acne Vulgaris A 12 week double-blind clinical trial was performed to assess the efficacy and tolerance of Intensive Renewing Serum (IRS)+UNBLEMISH Regimen when used by women with mild to moderate acne vulgaris. The subjects included: n=23 females, ages 22-45, FP I-VI, with mild to moderate (score of 2-3 on IGA scale) acne vulgaris, having a minimum of 5 inflammatory lesions on the face, having mild to moderate (score of 1-6 on 0-9) crow's feet wrinkles (a minimum 50% of panel (approx. 15 subjects) had a crow's feet wrinkle score of 2-6 (on a 0-9) and underwent skin replicas and ultrasound), having mild to moderate (score of 3-6 on 0-9) skin clarity.

The UNBLEMISH Regimen includes the following: A) UNBLEMISH ACNE TREATMENT SULFUR WASH (ACTIVE INGREDIENT: Sulfur 3%; INACTIVE INGREDIENTS: Water/Aqua/Eau, Sodium Laureth Sulfate, Propylene Glycol, Distearyl Phthalic Acid Amide, Lauryl Glucoside, *Aloe barbadensis* Leaf Juice, Diisodecyl Adipate, Glycerin, Hydrogenated Polyisobutene, Polyacrylamide, Cetearyl Alcohol, Titanium Dioxide (CI 77891), *Arnica montana* Flower Extract, *Camellia sinensis* Leaf Extract, Cetyl Alcohol, Magnesium Aluminum Silicate, Ceteareth-20, Laureth-7, PEG-100 Stearate, C13-14 Isoparaffin, Bisabolol, Glyceryl Stearate, Xanthan Gum, Fragrance/Parfum, Methylparaben, Glutaral, Chlorphenesin, Diazolidinyl Urea, Phenoxyethanol, Propylparaben, Citronellol, Geraniol, Limonene, Linalool, Violet 2, Red 33.) B) UNBLEMISH CLARIFYING TONER (Water/Aqua/Eau, *Hamamelis virginiana* (Witch Hazel) Water, Ethoxydiglycol, *Aloe barbadensis* Leaf Juice, Glycolic Acid, Polysorbate 20, Alcohol, Sodium Hydroxide, Panthenol, *Camellia sinensis* Leaf Extract, *Rosmarinus officinalis* (Rosemary) Leaf Extract, Sodium Hyaluronate, Leuconostoc/Radish Root Ferment Filtrate, Arginine, Niacinamide, Azelaic Acid, Menthyl Lactate, Atelocollagen, Zinc Phenosulfonate, Lecithin, PEG-12 Dimethicone, Benzophenone-9, Xanthan Gum, Sodium Chondrotin Sulfate, Fragrance/Parfum, Butylene Glycol, Propylene Glycol, Disodium EDTA, DMDM Hydantoin, Chlorphenesin, Phenoxyethanol, Citronellol, Geraniol, Limonene, Linalool, Blue 1, Red 33.) C) UNBLEMISH DUAL INTENSIVE ACNE TREATMENT (ACTIVE INGREDIENT: Benzoyl Peroxide 5%; INACTIVE INGREDIENTS: Lotion: Water/Aqua/Eau, Glycerin, Polyacrylamide, Benzyl Alcohol, C13-14 Isoparaffin, Allantoin, Niacinamide, Panthenol, Ceramide AP, Ceramide NP, Ceramide EOP, *Aloe barbadensis* Leaf Juice, *Chamomilla recutita* (*Matricaria*) Flower Extract, *Punica granatum* Extract, *Yucca glauca* Root Extract, Biosaccharide Gum-1, Phytosphingosine, Cholesterol, Xanthan Gum, Carbomer, Disodium Oleamido MEA-Sulfosuccinate, Laureth-7, Sodium Lauroyl Lactylate, Sodium Sulfite, Disodium EDTA, Propylene Glycol, Phenoxyethanol. Enhancement Gel: Water/Aqua/Eau, Ethoxydiglycol, Corn Starch Modified, PEG-7 Glyceryl Cocoate, Phenoxyethanol, Carbomer, Triethanolamine, Fragrance/Parfum, BHT, Disodium EDTA, Ethylhexylglycerin, Citronellol, Geraniol, Limonene, Linalool.)

D) UNBLEMISH OIL CONTROL LOTION SPF 20 (ACTIVE INGREDIENTS; Zinc Oxide 4.75%, Titanium Dioxide 0.7%; INACTIVE INGREDIENTS: Water/Aqua/Eau, Cyclopentasiloxane, Isododecane, Pentylene Glycol, Cetearyl Alcohol, Polysilicone-11, Butylene Glycol, PEG-10 Dimethicone, Dimethicone, Azelaic Acid, Tetrahexyldecyl Ascorbate, Tocopherol, *Boerhavia diffusa* Root Extract, Atelocollagen, Nordihydroguaiaretic Acid, Oleanolic Acid, Lecithin, Tropolone, PEG-60 Almond Glycerides, Glycerin, Cholesterol, Squalane, Glyceryl Stearate, PEG-100 Stearate, Stearic Acid, Xanthan Gum, Polysorbate 60, Dimethiconol, Ceteth-10 Phosphate, Dicetyl Phosphate, Hexyl Laurate, Polyglyceryl-4 Isostearate, Sorbitan Isostearate, Alumina, Hydroxyethyl.)

Table 20 provides the subject rating of particular skin attributes at weeks 4 and 8 after treatment with the UNBLEMISH Regimen and treatment with IRS.

TABLE 20

Percentage of subjects noticing improvement.

| Skin Attributes | Week 4 | Week 8 |
| --- | --- | --- |
| Skin smoothness | 74% | 87% |
| Skin Softness | 65% | 83% |
| Evenness of skin texture | 74% | 78% |
| Skin Firmness | 57% | 78% |
| Evenness of skin tone | 52% | 78% |
| Skin fullness/plumpness | 52% | 74% |
| Skin radiance | 48% | 70% |
| Lines/wrinkles | 43% | 70% |

The clinical grading results of the clinical trial are provided in Table 21 at weeks 4 and 8 after treatment with the UNBLEMISH Regimen and treatment with IRS.

TABLE 21

Percentage of subjects showing improvement.

| Skin Attributes | Week 4 | Week 8 |
| --- | --- | --- |
| Skin smoothness/roughness (tactile) | 100% | 100% |
| Skin Texture (visual) | 100% | 100% |
| Skin radiance/luminosity/brightness | 65% | 91% |
| Skin tone evenness | 57% | 70% |
| Plumpness | 35% | 70% |
| Fine lines (crow's feet) | 30% | 35% |
| Wrinkles (global face) | 22% | 30% |
| Fine lines (global face) | 17% | 26% |
| Wrinkles (crow's feet) | 22% | 22% |
| Firmness (tactile) | 9% | 22% |
| Skin elasticity/resiliency/bounce back ('pinch recoil') | 13% | 13% |

Subjects showed a mean reduction in crow's feet when measured by replica analysis.

Table 22 provides the results of a global acne assessment and lesion count at weeks 4 and 8 after treatment with the UNBLEMISH Regimen and treatment with IRS.

TABLE 22

Percentage of subjects showing improvement.

| Skin Attributes | Week 4 | Week 8 |
| --- | --- | --- |
| Global acne assessment | 87% | 91% |
| Papules | 87% | 100% |
| Pustules (based on subjects that had pustules at baseline) | 86% | 100% |

TABLE 22-continued

Percentage of subjects showing improvement.

| Skin Attributes | Week 4 | Week 8 |
| --- | --- | --- |
| Open comedomes (based on subjects that had open comedones at baseline) | 100% | 100% |
| Closed comedones | 83% | 83% |
| Macules | 51% | 48% |

A comparison of treatment with the UNBLEMISH Regimen and the UNBLEMISH Regimen plus the IRS demonstrated a clear improvement in acne grade when the combination treatment was used. Table 23 shows the mean percent change in acne grade.

TABLE 23

Mean Percent Change in Acne Grade.

| | Week 2 | Week 4 | Week 6/8 |
| --- | --- | --- | --- |
| UNBLEMISH Regimen | 16% | 42% | 63% |
| UNBLEMISH Regimen + IRS | 37% | 59% | 65% |

Table 24 provides the objective (clinical) assessment of tolerability, all results at weeks 2, 4, and 8 fall into the very mild or mild category and is considered tolerable.

TABLE 24

Percentage of Subjects with Skin Ailment Compared to Baseline.

| Skin Ailment | Week 2 | Week 4 | Week 8 |
| --- | --- | --- | --- |
| Dryness | 17% | 4% | 0% |
| Peeling | 13% | 4% | 0% |
| Erythema | 9% | 0% | 0% |
| Stinging | 9% | 9% | 0% |
| Itching | 9% | 9% | 4% |
| Burning | 4% | 9% | 4% |
| Scaling | 4% | 0% | 0% |
| Edema | 0% | 0% | 0% |

Example 7: Silicone Gel with Retinal Formulation

The concentration of each component of an exemplary topical skin composition, referred to as silicone gel with retinal, can be found in Table 25.

TABLE 25

Silicone Gel with Retinal

| INCI | Concentration |
| --- | --- |
| Retinal/Retinaldehyde | 0.125% |
| Dimethicone, Isododecane, Polysilicone-11 | 79.000% |
| L-ascorbic acid | 15.000% |
| Isododecane | 4.875% |
| Dimethyl Isosorbide and Hydroxypinacolone Retinoate | 1.00% |

Example 8: Emulsion with Retinal Formulation

The concentration of each component of an exemplary topical skin composition, referred to as emulsion with retinal, can be found in Table 26. The following steps are taken to prepare the emulsion: 1) Prepare PHASE A under propeller at medium speed. 2) Premix PHASE A1 and add PHASE A, mix and heat to 75° C. until uniform. 3) In separate vessel, prepare PHASE B and heat to 75° C. 4)

When PHASE A and PHASE B reach 75° C., add PHASE B to PHASE A under homogenization. 5) Cool to 50° C. and add PHASE C, homogenize until uniform. 6) Cool to 40° C. and add PHASE D, homogenize until uniform. 7) In a separate container, take 10% of cream to well disperse Hydroxysomes Retinaldehyde by mixing and homogenizing. Hydroxysomes Retinaldehyde does not solubilize in the formula, and the particles must be well evenly dispersed. Transfer to main container and continue to homogenize and well disperse.

TABLE 26

Emulsion with Retinal

| PHASE | INCI | Concentration |
|---|---|---|
| A | Water | 85.345% |
| A1 | Xanthan gum | 0.300% |
|  | Glycerin | 1.000% |
| B | Caprylic/Capric triglycerides | 3.000% |
|  | Cetyl alcohol | 2.000% |
|  | Stearyl alcohol | 2.000% |
|  | Glyceryl stearate and PEG-100 stearate | 1.000% |
|  | Dimethicone | 3.000% |
| C | Polyacrylate-13, polyisobutene, polysorbate-20 | 1.000% |
| D | Phenoxyethanol and ethylhexylglycerin | 1.000% |
| E | Retinal/Retinaldehyde and hydroxyapatite | 0.355% |

Example 9: Clinical Study Evaluating Efficacy and Tolerance of IRS Compared with Adapalene Gel The objective of the study is to evaluate and compare the anti-aging efficacy and tolerability of 0.1% Adapalene compared to Intensive Renewing Serum over a 12-week period when used by women with mild to moderate lines and wrinkles, dullness and moderate dyschromia.

Subjects reported to the facility at Baseline for Expert Grader assessments of various facial photoaging and irritation parameters, subjective assessments of facial irritation, digital imaging of the face, replica sampling of the crow's foot area, capacitance and firmness/elasticity measurements of the face and completed a self-assessment questionnaire. Subjects were randomized to receive 1 of 2 investigational products for treatment to the entire face for 12 weeks. Subjects returned to the lab at Week 2 and Week 4 to have Expert Grader assessments, digital imaging and self-assessments repeated. At Weeks 8 and 12, subjects returned for Expert Grader assessments, digital imaging, replica sampling, capacitance and firmness/elasticity measurements and self-assessments.

Treatments & Procedures:

Expert Grader Assessments: In addition to screening and selecting the final panel, an Expert Grader assessed the face of each subject for various irritation and efficacy parameters at Baseline and after 2, 4, 8 and 12 weeks of treatment. The scale that was used for each assessment parameter (unless otherwise indicated) is: 0=none, 1-3=mild, 4-5=moderate, 7-9=severe.

Irritation parameters: The Expert Grader assessed the face of each subject at each time point for the following irritation parameters using a 0-9 scale: Erythema, Dryness, Scaling, and Edema. Using a 0-9 scale, subjects were asked to rate their amount of: Burning, Stinging, Itching, Tightness, and Dryness.

Efficacy parameters: The assessments of efficacy were made using methods that would provide the Sponsor the most information on changes in the subject's skin over time.

The methods that the Expert Grader used to assess efficacy are as follows: 1. Live Grading: Absolute scores from viewing the subject's face were assigned using a 0-9 scale. Live grades were conducted at each time point. 2. Baseline Aided Grading: Absolute scores from viewing the subject's face were assigned using a 0-9 scale at the Baseline visit and the Expert Grader used the subject's Baseline photo for reference at follow-up visits. Baseline aided grading was conducted at each time point other than at Baseline. 3. Comparison Grading from Photos: Comparison grading was performed after the conclusion of the study. The Expert Grader compared the photos from each time point to Baseline for improvement/worsening using the below scale: −4=Marked worsening, −3=Moderate worsening, −2=Mild worsening, −1=Barely perceptible worsening, −0.1=Forced choice worsening, 0=No change, 0.1=Forced choice improvement, 1=Barely perceptible improvement, 2=Mild improvement, 3=Moderate improvement, and 4=Marked improvement.

The following efficacy parameters were assessed by the Expert Grader along with the assessment method(s) are listed: 1. Skin Texture (softness/smoothness) [tactile]: Live grading, 2. Skin Texture [visual]: Live grading/Baseline aided, 3. Fine Lines (eye area including crow's feet): Live grading/Baseline aided/Comparison scores from photos, 4. Wrinkles (eye area, including crows feet): Live grading, Baseline aided, Comparison scores from photos, 5. Pore appearance: Comparison scores from photos, 6. Firmness: Live grading, 7. Sagging (nasolabial fold area): Comparison scores from photos, 8. Discrete hyperpigmentation: Comparison scores from photos, 9. Mottled hyperpigmentation: Comparison scores from photos, 10. Skin tone evenness: Comparison scores from photos, 11. Radiance/luminosity/glow (defined as Dull to luminous/shiny): Live grading, 12. Sallowness (sallow to rosy): Live grading/Baseline aided, 13. Overall healthy skin appearance: Comparison scores from photos, 14. Overall photodamage: Live grading/Baseline aided, 15. Pinch recoil (under the eye): Live grading (For this assessment, a 0-9 score will not be assigned. Per the Sponsor, the evaluator will pinch the subject's skin at the designated site using the thumb and forefinger and hold the skin in place for approximately 2 seconds. A stopwatch will be started upon release and the time required for the subject's skin to return to its original conformation will be measured to the nearest tenth of a second. A decrease in pinch recoil times over time indicates an improvement in skin "bounce-back" or elasticity/resiliency.). For the above efficacy parameters, parameters that indicate live grades were completed at Baseline and after 2, 4, 8 and 12 weeks of treatment. For the parameters that indicate grading of photos, the grading was completed after the conclusion of the study.

Digital Photography: Digital images using visible, cross-polarized, parallel, and UV lighting were taken of each subject's face using a custom photography system. Images were taken of each subject's face (Left, Right and Center views) at Baseline and again after 2, 4, 8 and 12 weeks of treatment.

Skin Surface Impressions: Silflo impressions of the left crow's foot area were made by a trained cyberDERM technician at Baseline (prior to treatment) and again after 8 and 12 weeks of treatment. The sampled site on each individual subject was delineated by affixing an adhesive ring using extreme care not to alter the surface tension across the skin. Skin impressions were obtained with silicon dental impression material. A thin layer of freshly prepared material was gently spread over the bounded area of the ring using a stainless steel spatula. Within 2 to 3 minutes, the material should polymerize after which time the ring together with the impression was lifted from the skin. Each specimen was immediately coded as to subject, time point and test site. A Digital Image Analysis System consisting of Visioline VL 650 hardware (Courage+Khazaka, Cologne, Germany) with a specialized image analysis software package (Image-Pro Premiere) was used. The resulting images consisted of a series of shadows that directly corresponded to the pattern of wrinkles. During analysis, one can measure changes in skin surface topography by selecting a gray level threshold that allows one to directly determine the projected area of the shadowed region associated with the wrinkles. Changes in skin surface topography can be quantified by measuring the dimensions of the individual shadows as well as the overall area of shadowing.

Corneometer® CM 825: All measurements were taken following a minimum 25-minute acclimation period in a controlled environment with the relative humidity maintained at less than 50% and temperature maintained at 19-22° C. The measuring principle of the Courage+Khazaka Corneometer® CM 825 is based on capacitance measurement of a dielectric medium. Any change in the dielectric constant due to skin surface hydration variation alters the capacitance of a precision measuring capacitor. The measurement can detect even slight changes in the hydration level. The reproducibility of the measurement is very high and the measurement time is very short (1 s). The instrument technician took five measurements from the left and right sides of the face at the nexus where a line drawn lateral from the nostril meets a line drawn vertical from the corner of the eye at Baseline (prior to treatment) and again after 8 and 12 weeks of treatment. The average value was computed for each site after each measurement session.

DermaLab® Suction Cup: All measurements were taken following a minimum 25-minute acclimation period in a controlled environment with the relative humidity maintained at less than 50% and temperature maintained at 19-22° C. A DermaLab® USB with a Suction Cup was used to evaluate skin elasticity. The suction probe which was placed on the test site is capable of producing a vacuum up to 650 mbar. Within the suction chamber there is a height detection system to measure how much the skin has moved as a result of the applied vacuum. The measuring aperture is 10 mm in diameter and the probe itself has an ultra low weight of approximately 7 g for minimum skin bias. The probe was secured to the panelist's site using an adhesive ring. When the suction pump is activated it creates a vacuum that draws the skin into the chamber and the height to which the skin is drawn in is recorded in the software and used to calculate elasticity parameters. The skin is then allowed to relax for 1 second before the vacuum resumes for a total of 5 cycles. Parameters related to elasticity and firmness were reported. The instrument technician took one measurement from the left and right sides of the face at the nexus where a line drawn lateral from the nostril meets a line drawn vertical from the corner of the eye at Baseline (prior to treatment) and again after 8 and 12 weeks of treatment.

Self-Assessment Questionnaires: Subjects completed Sponsor-supplied self-assessment questionnaires (Appendix D) at Baseline and after 2, 4, 8 and 12 weeks of treatment.

Baseline Questionnaire included questions about skin type, the frequency of acne pimples or breakouts, types and names of products used in their regular skincare routine, effects of other products on skin.

Week 2 Questionnaire included questions about what the subject liked and disliked about the test product, if the subject experienced any irritation (burning, stinging, itching, tightness, dryness, redness, etc.) while using the test product for the past 2 weeks.

Week 4 Questionnaire included questions about what the subject liked and disliked about the test product, if the subject experienced any irritation (burning, stinging, itching, tightness, dryness, redness, etc.) while using the test product for the past 2 weeks, and was asked to rate the level of agreement with the following statements compared to starting the study (baseline): a. Skin looks healthier, b. Skin feels healthier, c. My skin looks clearer, d. Pores appear smaller, e. I experienced fewer pimples/breakouts, f Skin feels firmer, g. Skin's texture looks smoother, h. Age spots/darks spots are less visible, i. Skin's texture is visibly more even, j. Skin feels smoother, k. Skin is visibly more radiant, l. Skin looks visibly younger, m. Skin feels younger, n. Skin tone/color is visibly more even, o. I see fewer lines/wrinkles, p. The product reduced the appearance of nose to mouth lines (nasolabial folds), q. Skin is visibly less red, r. Oily and dry patches feel more balanced, s. Makeup stays fresh all day after using the product, t. Makeup goes on much better after using the test product, u. I like the overall appearance of my skin, v. The test product did not leave my skin feeling tight or uncomfortable, w. I liked using the test product nightly, and x. I liked using the test product.

Weeks 8 and 12 Questionnaires included questions similar to the week 4 questionnaire, as well as whether the subject was satisfied with their results and would they continue to use the product and recommend product to a friend.

Investigational Products: The following investigational products (test product and benchmark) were supplied by the Sponsor and were labeled as follows:

Product C: REDEFINE Intensive Renewing Serum,
Product N: Differin 0.10% Adapalene Treatment Procedures: approximately 20-25 subjects assigned to each product per randomization. After the Baseline assessments and measurements had been completed, the subjects reported to the Treatment Technician, who dispensed a new container of their assigned product to the subject and instructed the subject to apply the product according to the Sponsor's instructions below:

Product C: Morning instructions: Follow your regular morning skincare routine. Evening instructions: Product C should be used once daily in the evening, after your regular cleanser. Open a capsule by twisting off the tail end of one capsule. Apply the serum over your entire face, including under the eyes and crow's feet. Do not apply on eyelids. Avoid getting into eyes, In case of inadvertent eye contact, rinse eyes with plenty of water to remove product from eyes. Do not wash off from skin. Use one capsule per night. Follow with the rest of your evening skin care Regimen. Note: make sure that no water gets into the jar and that your hands are dry before use. Please ensure the jar is tightly closed after each use.

Product N: Morning instructions: Follow your regular morning skincare routine. Evening instructions: Product N should be used once daily in the evening, after your regular cleanser. Clean the skin gently with your regular cleanser and pat dry before applying Product N. Cover the entire face, including under the eyes and crow's feet, with a thin layer. Do not apply on eyelids. Avoid product contact with eyes, lips and mouth. If contact occurs, immediately flush the area with water. Do not wash off. Wash hands after use. Do not use more than one time a day. Follow with the rest of your evening skin care Regimen.

The results of the tolerability assessments demonstrates Intensive Renewing Serum was well tolerated and more tolerated than Adapalene. These assessments were measured subjectively and objectively as described above.

Subjective Results—Burning: somewhat greater degree of perceived burning with Adapalene, Stinging: somewhat greater degree of perceived stinging with Adapalene, Itching: little to no difference in perceived itching between products, Dryness/Tightness: slightly greater perception of dryness/tightness with Adapalene, most notably at Week 4.

Objective (Clinical) Results—Erythema: somewhat greater degree of erythema with Adapalene, Dryness: greater degree of tactile dryness with Adapalene, Scaling: greater degree of visual scaling with Adapalene, Edema: little or no edema with both products.

Figure 4A:
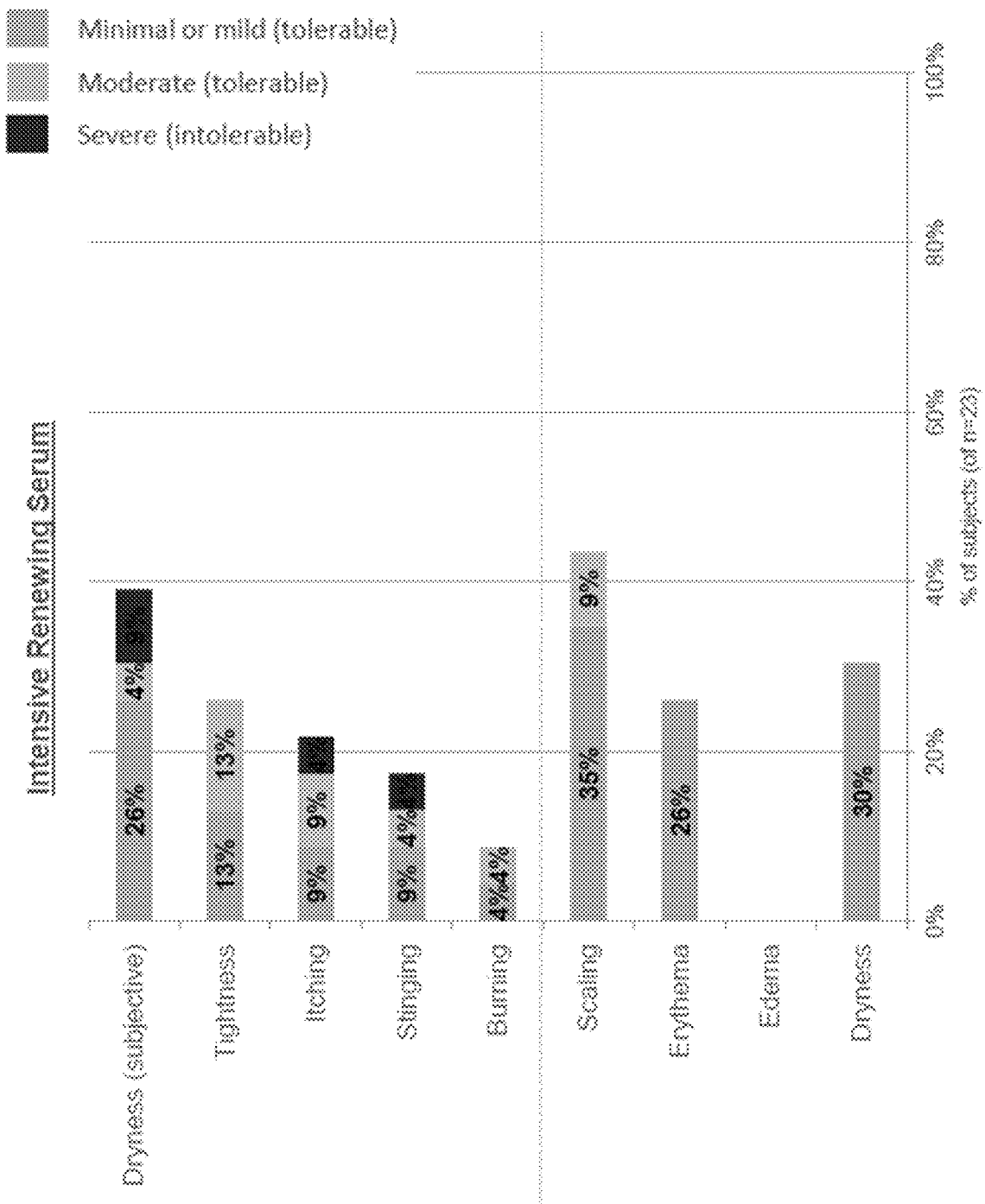
FIG. 4A (IRS) and FIG. 4B (adapalene) graphically depict tolerability results at week 2.
Figure 4B:
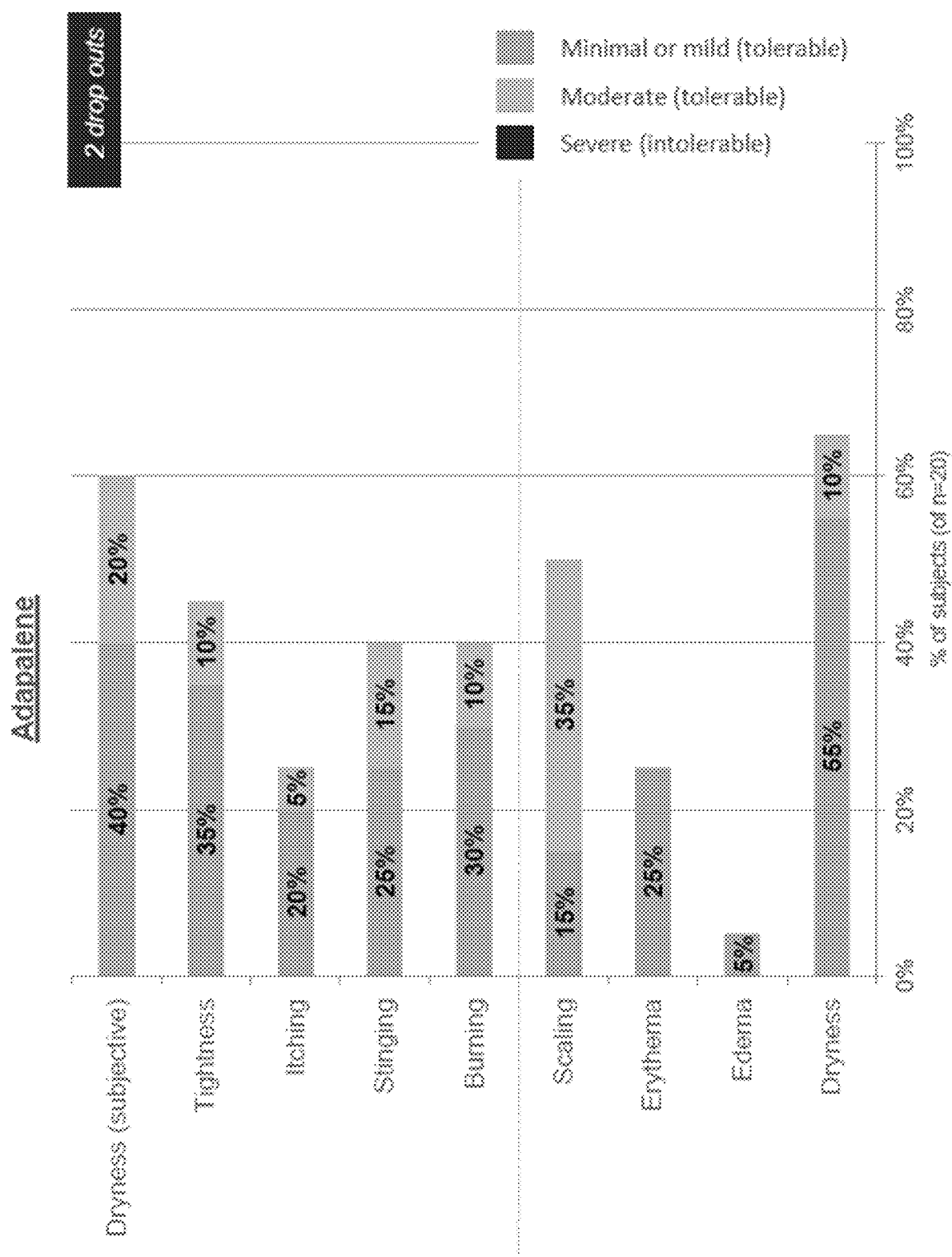
Figure 5A:
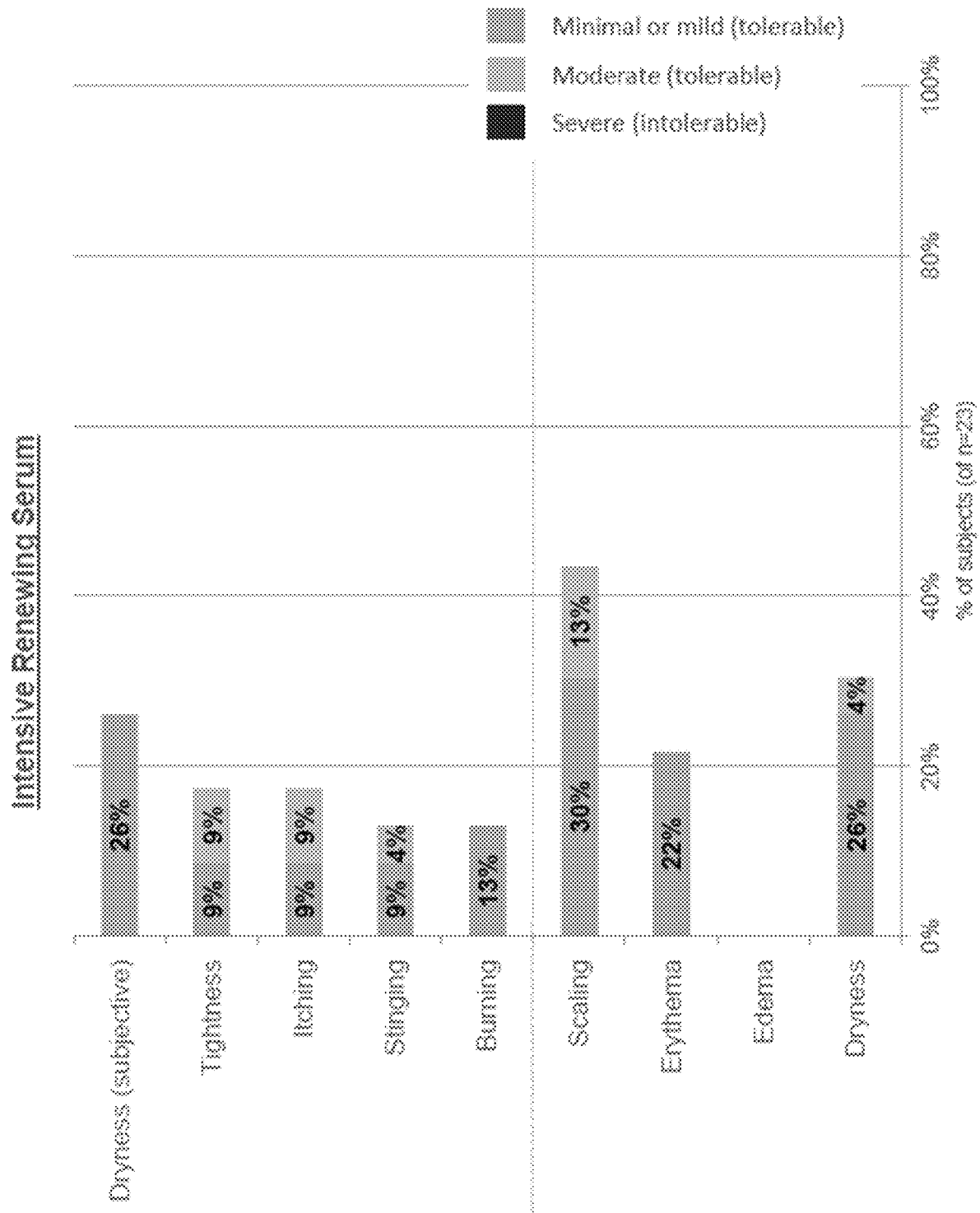
FIG. 5A (IRS) and FIG. 5B (adapalene) graphically depict tolerability results at week 4.
Figure 5B:
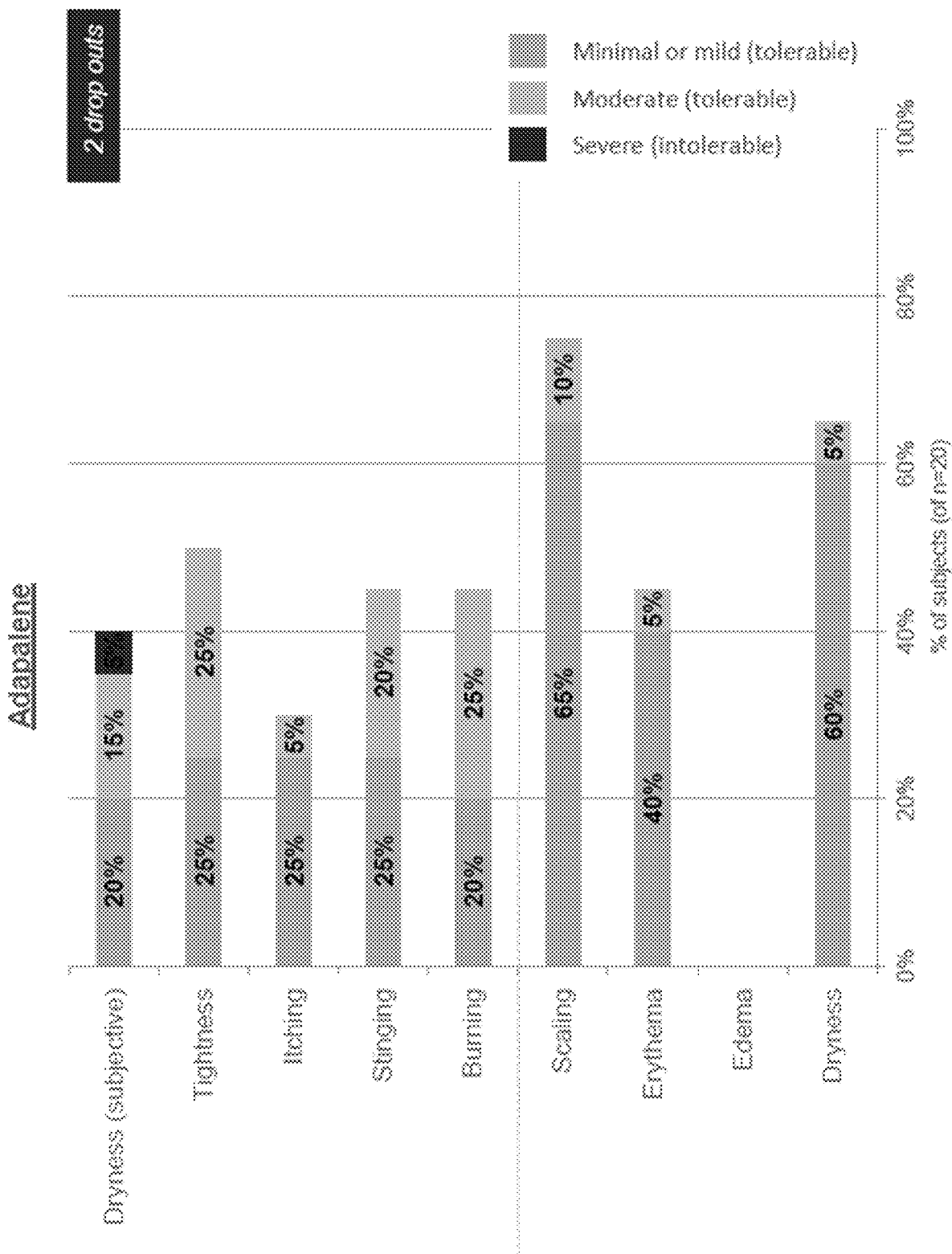
Figure 6A:
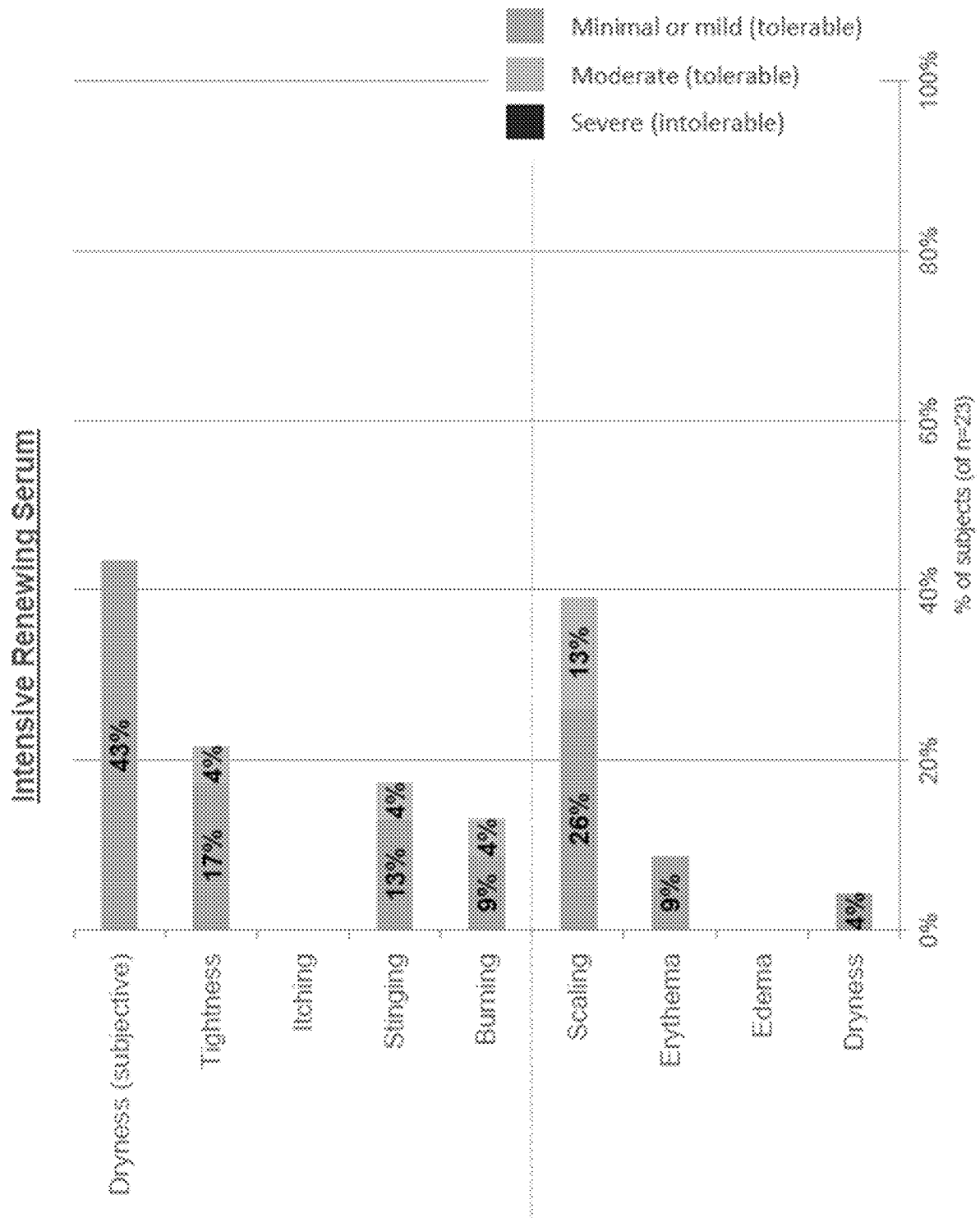
FIG. 6A (IRS) and FIG. 6B (adapalene) graphically depict tolerability results at week 8.
Figure 6B:
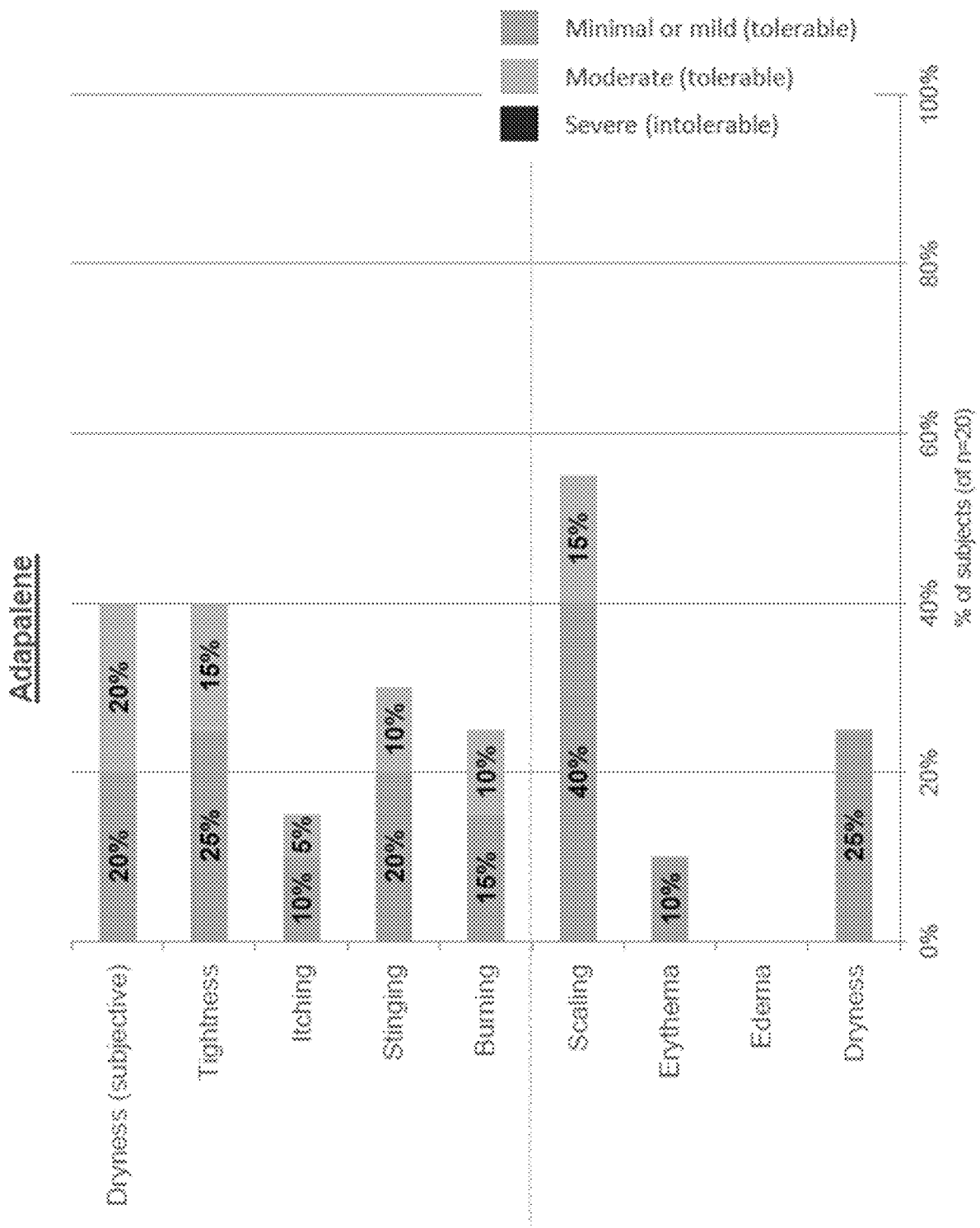
Figure 7A:
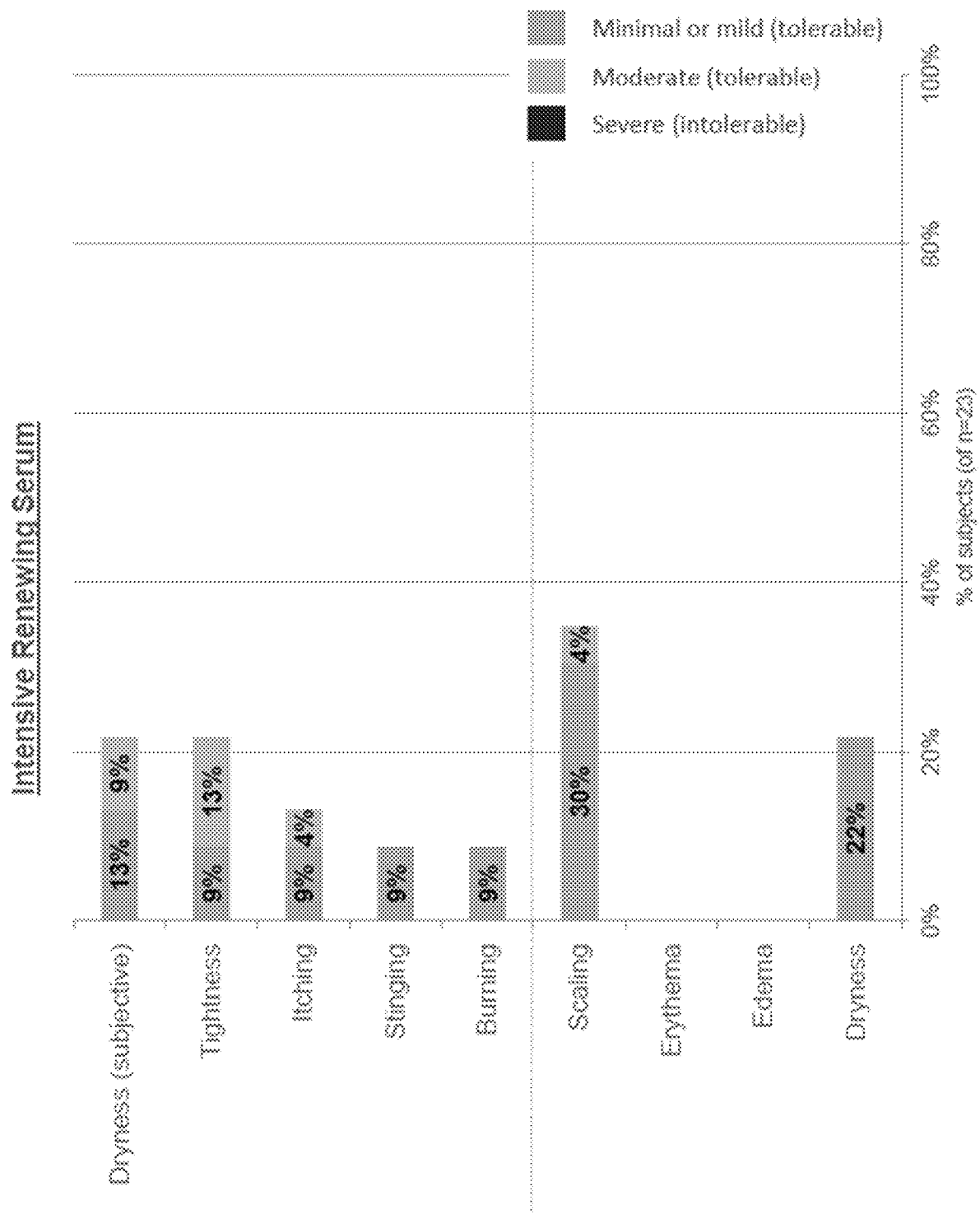
FIG. 7A (IRS) and FIG. 7B (adapalene) graphically depict tolerability results at week 12.
Figure 7B:
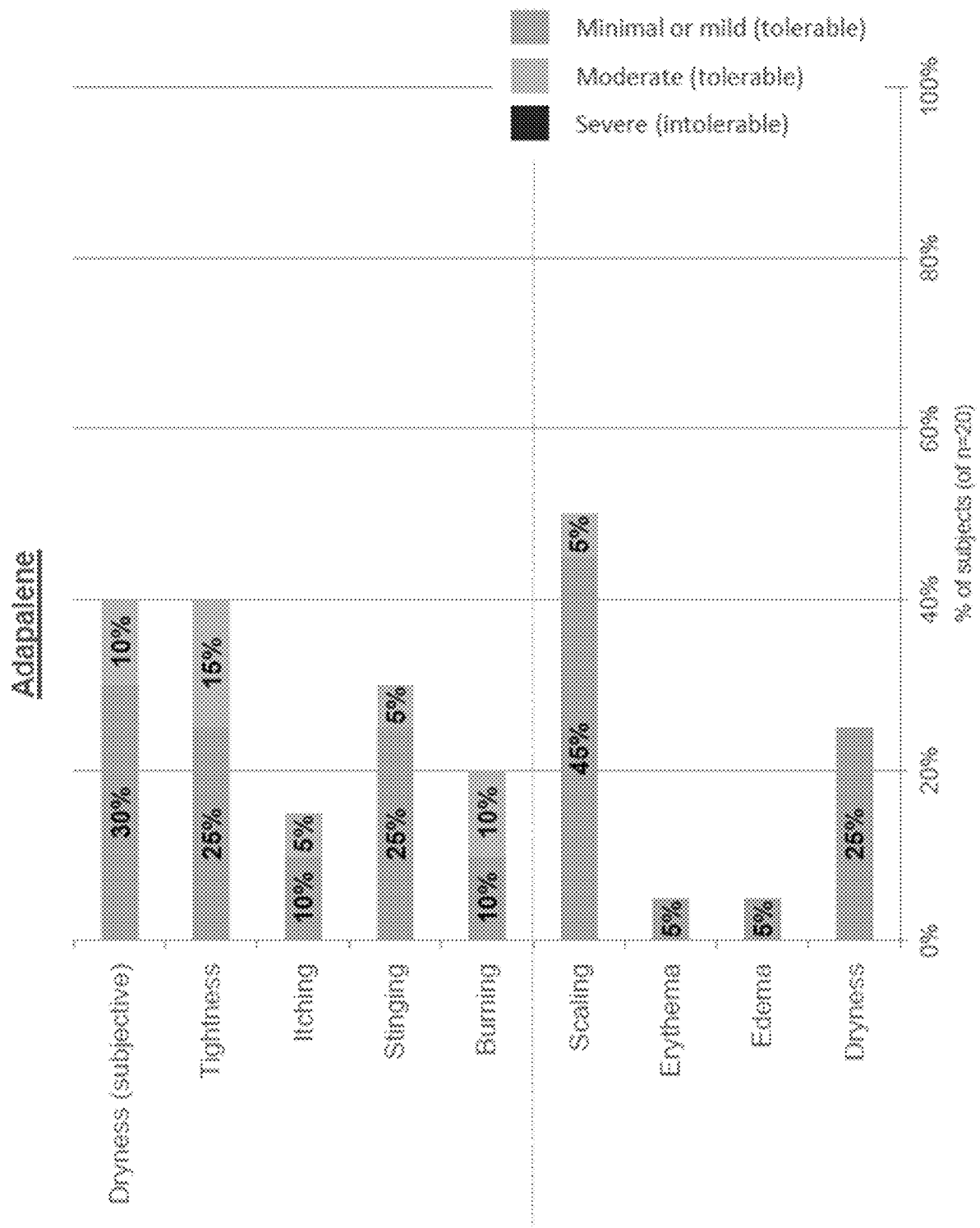

FIG. 4A (IRS) and FIG. 4B (adapalene) graphically depict tolerability results at week 2. FIG. 5A (IRS) and FIG. 5B (adapalene) graphically depict tolerability results at week 4. FIG. 6A (IRS) and FIG. 6B (adapalene) graphically depict tolerability results at week 8. FIG. 7A (IRS) and FIG. 7B (adapalene) graphically depict tolerability results at week 12. Parameters listed above dotted line=subjective assessment, below dotted line=clinical (objective) assessment.

Figure 8:
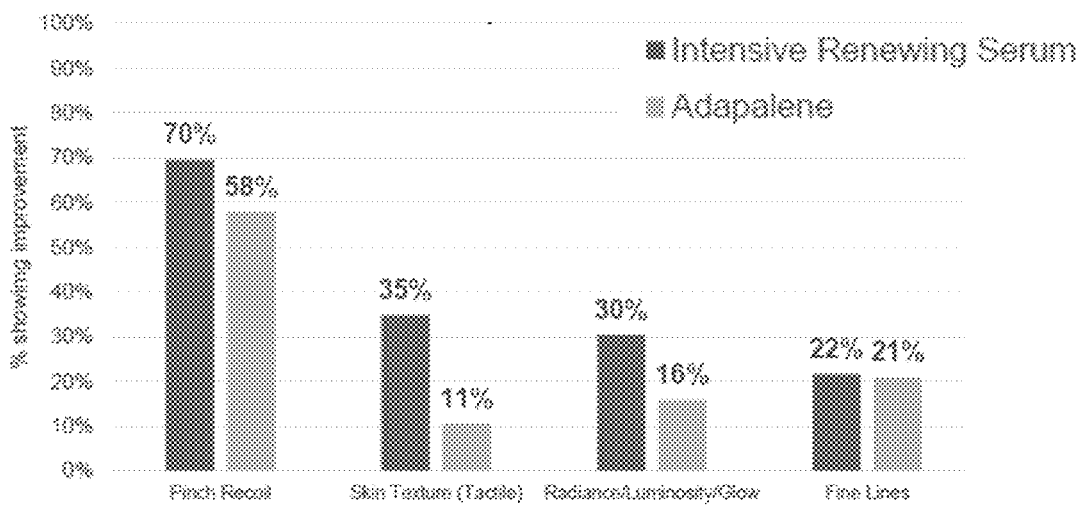
FIG. 8 graphically depicts the clinical grading assessment results for Intensive Renewing Serum and Adapalene at week 2.
Figure 8:
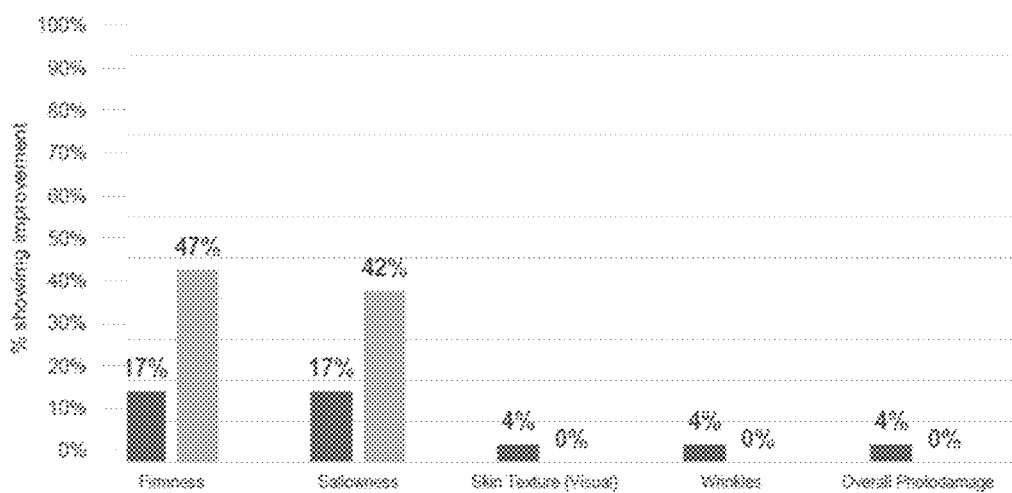
Figure 9:
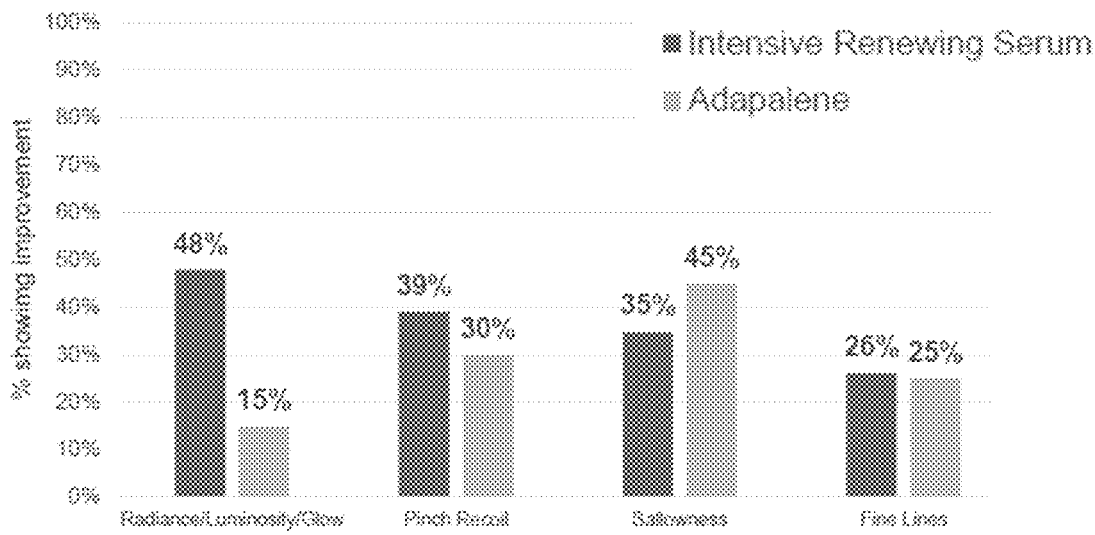
FIG. 9 graphically depicts the clinical grading assessment results for Intensive Renewing Serum and Adapalene at week 4.
Figure 9:
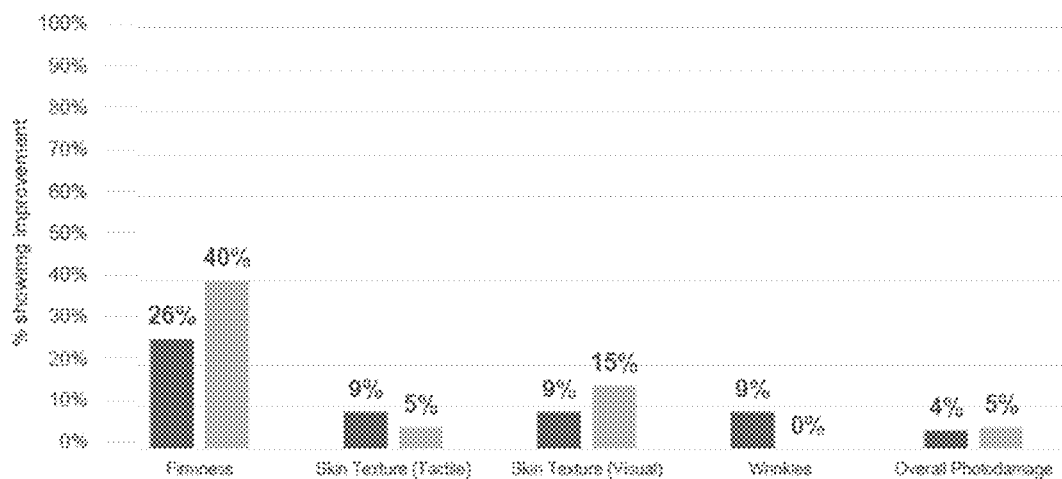
Figure 10:
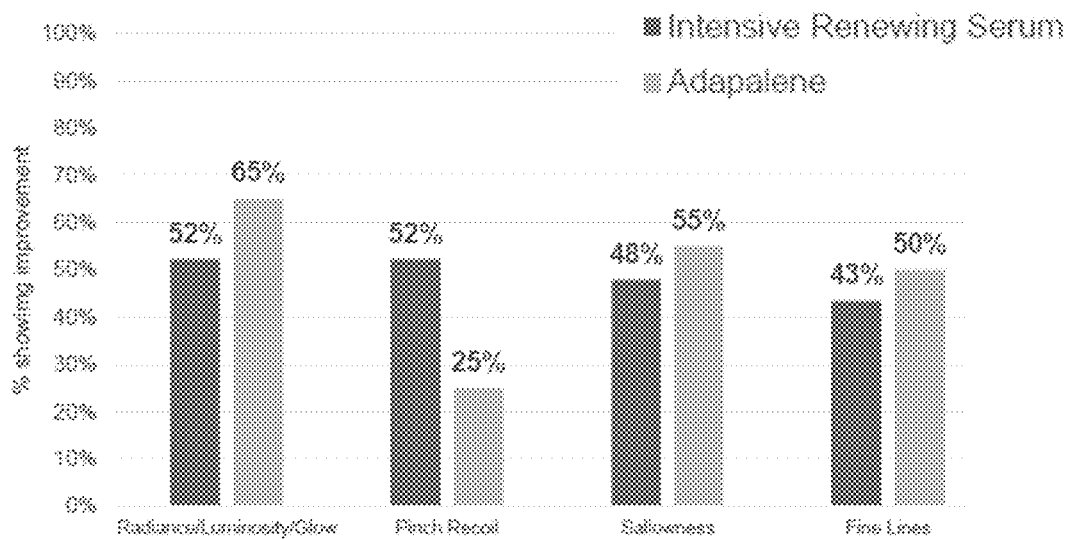
FIG. 10 graphically depicts the clinical grading assessment results for Intensive Renewing Serum and Adapalene at week 8.
Figure 10:
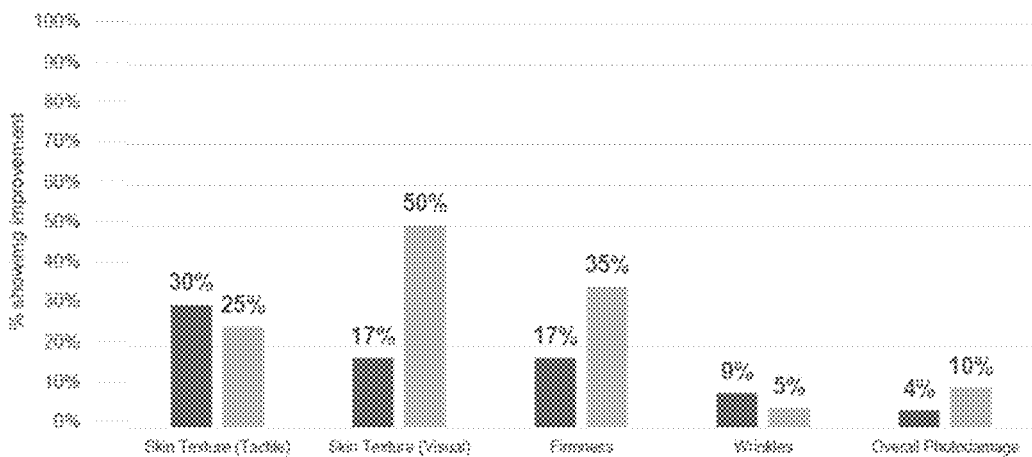
Figure 11:
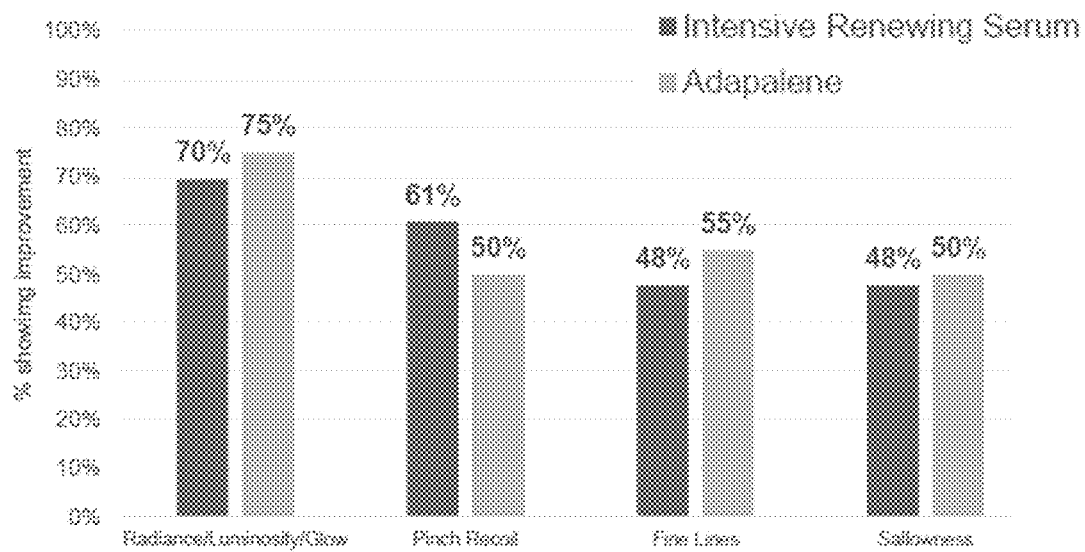
FIG. 11 graphically depicts the clinical grading assessment results for Intensive Renewing Serum and Adapalene at week 12.
Figure 11:
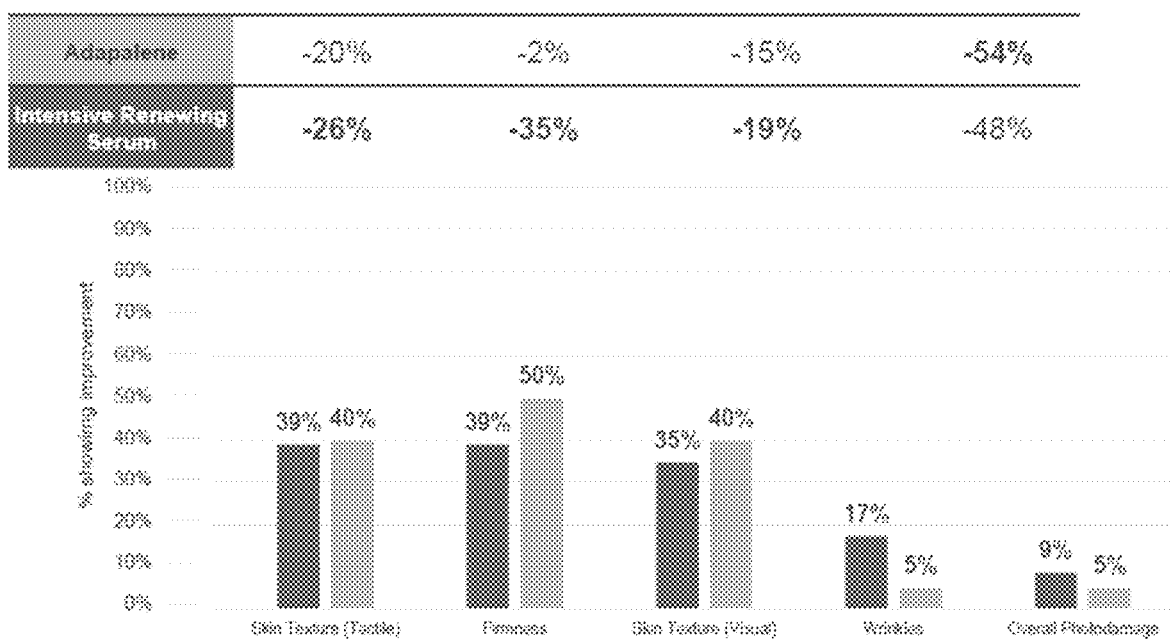

The results of the clinical grading assessment of efficacy demonstrate that, in terms of mean % change from baseline, Intensive Renewing Serum performed slightly better than Adapalene. FIGS. 8 (week 2), 9 (week 4), 10 (week 8), and 11 (week 12) graphically depict incidence of improvement results.

Skin Texture (Tactile): slight improvement with IRS by week 8 thru week 12. By week 12, no improvement with Adapalene; Skin Texture (Visual): slight improvement with IRS and Adapalene by weeks 8 & 12; Fine Lines: both were comparable first 4 weeks with mild improvements by week 8, IRS continues to improve through week 12, while Adapalene remains constant; Wrinkles: little or no change in mean scores for both products; Firmness (Tactile): mild increase in firmness for both by week 12; Radiance/Luminosity/Glow: mild progressive improvement throughout 12 weeks with IRS, Mild improvement persists through week 8 with Adapalene; Sallowness: mild improvement for both products; Overall Photodamage: no change in mean scores for both products; and Elasticity/Resiliency: slight improvement with IRS by weeks 8 & 12, No improvement with Adapalene.

Figure 12:
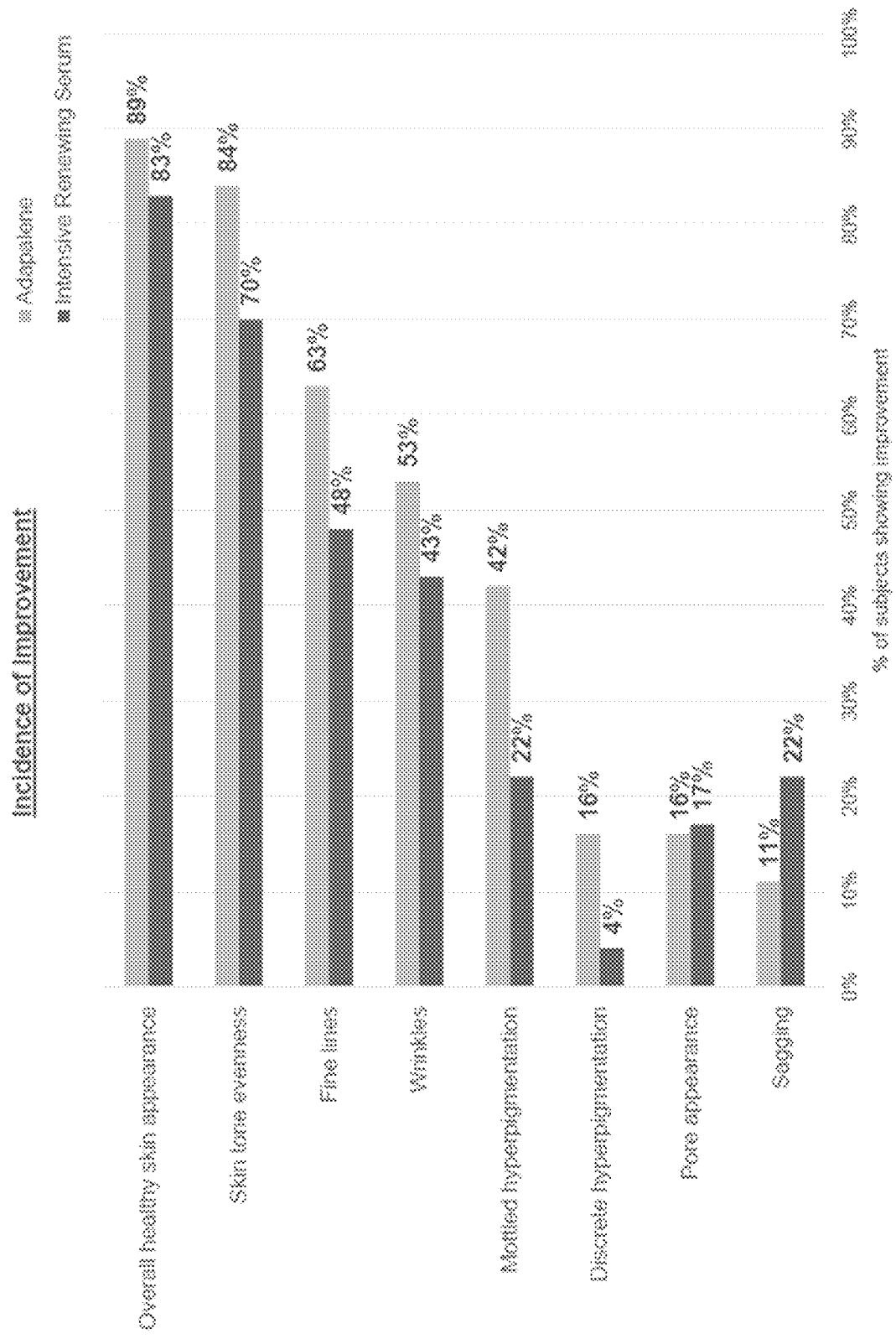
FIG. 12 graphically depicts the photo comparison clinical grading assessment results for Intensive Renewing Serum and Adapalene at week 2.
Figure 13:
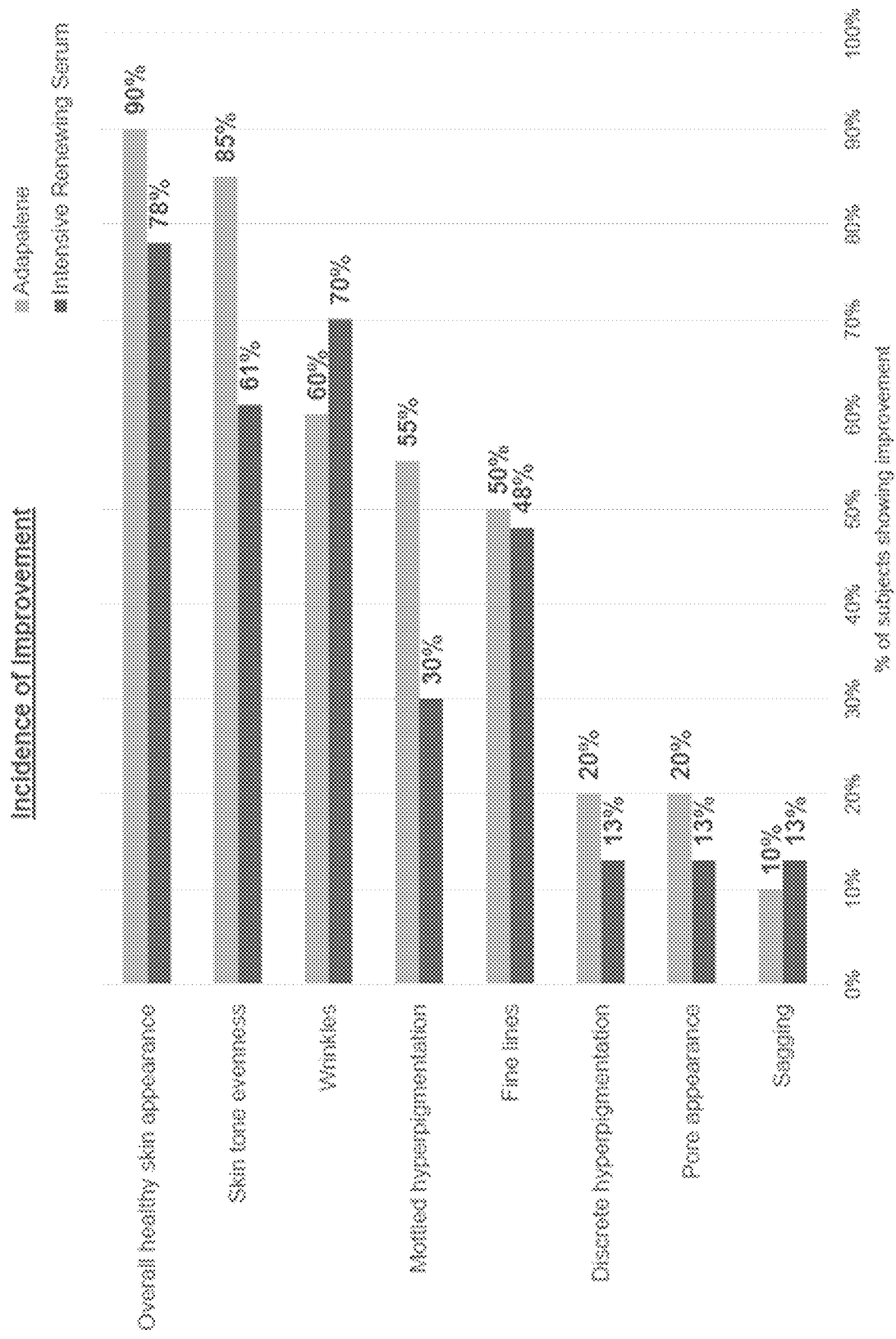
FIG. 13 graphically depicts the photo comparison clinical grading assessment results for Intensive Renewing Serum and Adapalene at week 4.
Figure 14:
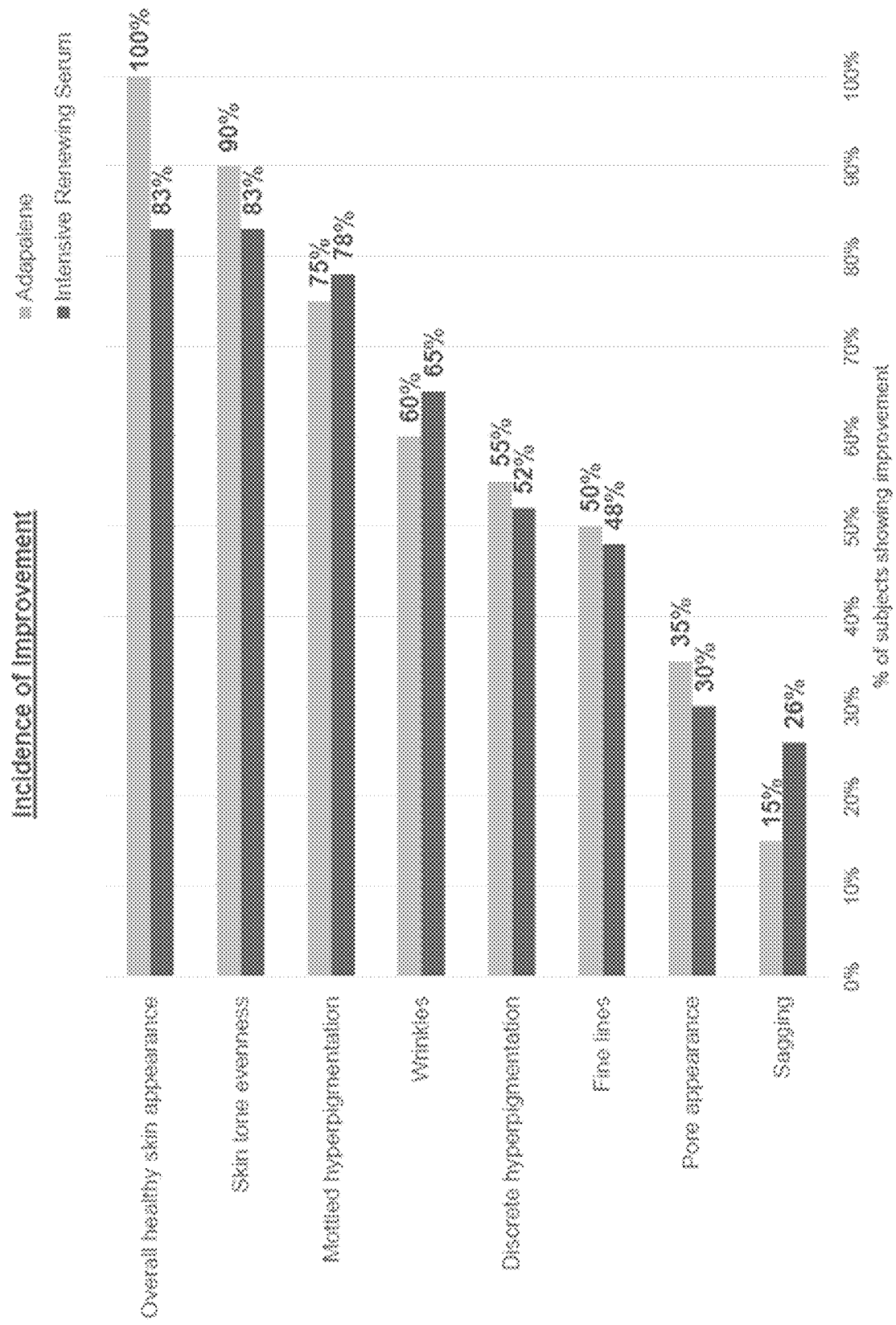
FIG. 14 graphically depicts the photo comparison clinical grading assessment results for Intensive Renewing Serum and Adapalene at week 8.
Figure 15:
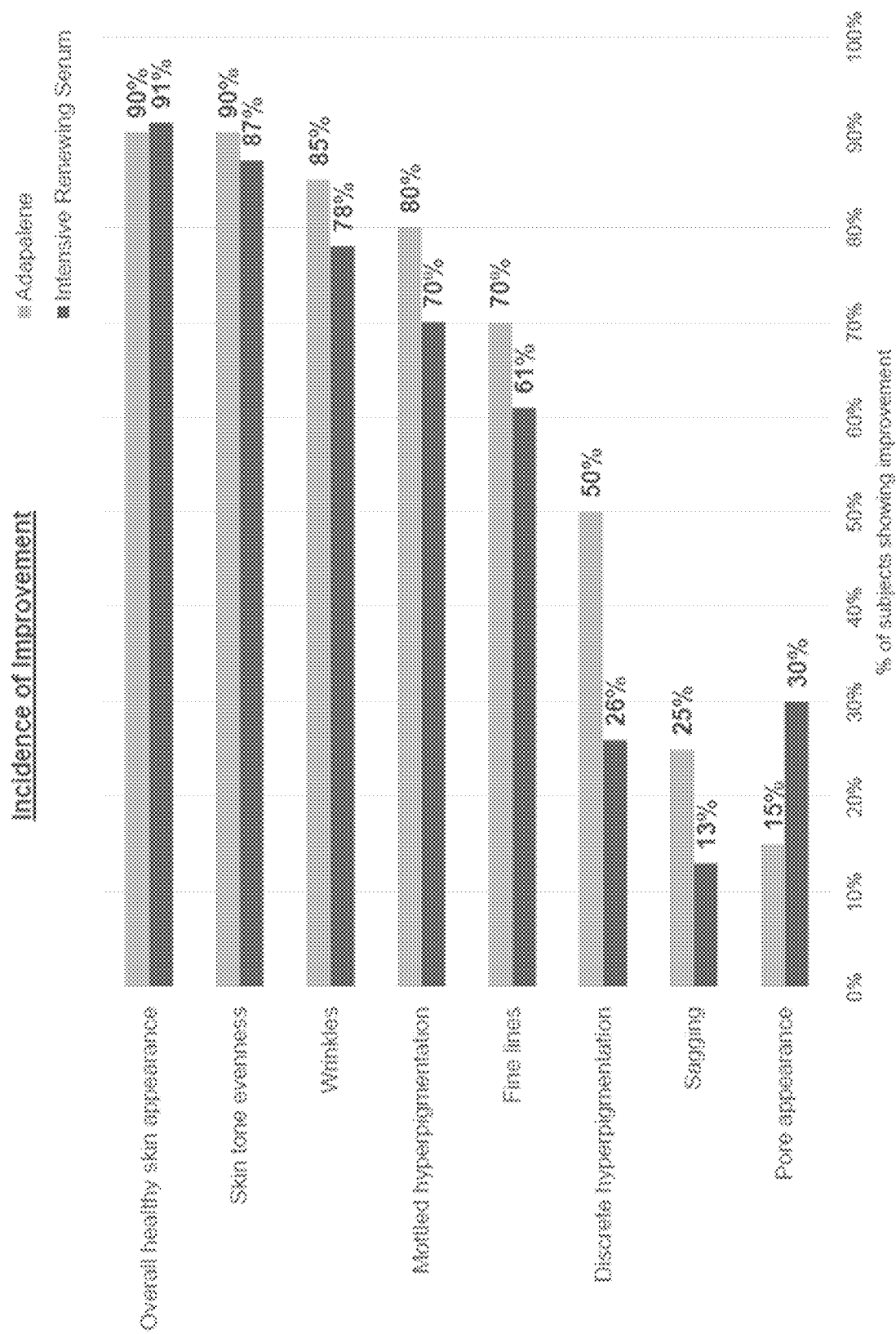
FIG. 15 graphically depicts the photo comparison clinical grading assessment results for Intensive Renewing Serum and Adapalene at week 12.

The results of the photo comparison demonstrates the mean scores slightly favored Adapalene over Intensive Renewing Serum. FIGS. 12 (week 2), 13 (week 4), 14 (week 8), and 15 (week 12) graphically depict incidence of improvement results.

Fine Lines: slight improvement by week 12 for both products; Wrinkles: slight, progressive improvement through week 12 for both products; Discrete Hyperpigmentation: slightly better results with Adapalene. Little or no improvement by week 12 with IRS; Mottled Hyperpigmentation: slight improvement by week 8 with IRS. A progressive & slightly better result with Adapalene; Skin Tone Evenness: slight, progressive improvement by week 4 through week 12 with both products; Overall Healthy Skin Appearance: slight, progressive improvement by week 4 through week 12 with both products; Pore Appearance: no change for either product; and Sagging: no change for either product.

Table 27 provides the results of the self-assessment questionnaires, which provided information regarding the subject's overall experience with the products. Subjects using the Intensive Renewing Serum were much more satisfied with their results after 12 weeks.

TABLE 27

| | Summary of User Experience | | | | | |
|---|---|---|---|---|---|---|
| | Week 4 | | Week 8 | | Week 12 | |
| Statement | % agreement for IRS | % agreement for adapalene | % agreement for IRS | % agreement for adapalene | % agreement for IRS | % agreement for adapalene |
| I liked using the test product | 91 | 57 | 96 | 65 | 87 | 45 |
| I liked using the test product nightly | 87 | 61 | 91 | 65 | 96 | 50 |
| The test product did not leave my skin feeling tight or uncomfortable | 61 | 35 | 70 | 50 | 83 | 45 |
| Makeup stays fresh all day after using the product | 61 | 26 | 57 | 40 | 61 | 35 |
| Makeup goes on much better after using the test product | 52 | 26 | 61 | 25 | 70 | 30 |

TABLE 27-continued

Summary of User Experience

| | Week 4 | | Week 8 | | Week 12 | |
| --- | --- | --- | --- | --- | --- | --- |
| Statement | % agreement for IRS | % agreement for adapalene | % agreement for IRS | % agreement for adapalene | % agreement for IRS | % agreement for adapalene |
| I want to continue using this product | — | — | 87 | 70 | 87 | 50 |
| I would recommend this product to a friend | — | — | 87 | 70 | 87 | 55 |

Example 10: Clinical Study of the Safety and Efficacy of IRS for Acne

The objective of this study was to evaluate the efficacy and tolerance of the Intensive Renewing Serum with a skin care regimen when used by women with mild to moderate acne vulgaris over a twelve week time period.

This was a single center, single cell (target completion n=25), non-randomized 12 week clinical study of female subjects ages 22-45 years of age with a Fitzpatrick Skin Type of I-VI with mild to moderate acne vulgaris (defined by an IGA score of 2-3) on the face with a minimum of 5 inflammatory lesions (jawline to hairline), mild to moderate skin clarity (defined by a score of 3-6 on a 0-9 scale) and mild to moderate crow's feet wrinkles (defined by a score of 1-6 on a 0-9 scale). A minimum of 50% of subjects had a moderate degree of crow's feet wrinkles (defined by a score of 4-6 on a 0-9 scale) and this group of subjects underwent analysis skin surface impressions and ultrasound measurements.

Clinical Evaluations: At the Baseline, Week 2, Week 4, Week 8, and Week 12 visits the Principal Investigator assessed the following clinical grading parameters:

1. Investigator Global Acne Assessment Score: 0=Clear, residual hyperpigmentation and erythema may be present; 1=Almost clear, a few scattered comedones and a few (less than five) small papules; 2=Mild, easily recognizable; less than half the face is involved, many comedones and many papules and pustules; 3=Moderate, more than half of the face is involved, numerous comedones, papules, and pustules; 4=Severe, entire face is involved, covered with comedones, numerous papules and pustules, and few nodules and cysts; 5 Very severe, highly inflammatory acne covering the face; with nodules and cysts present.

2. Global Lesion Count: At the Baseline, Week 2, Week 4 and Week 8 visits each subject had their inflammatory lesions (papules and pustules) and non-inflammatory lesions (open and closed comedones) and macules (PIH/PIE) separately counted and recorded for their forehead, left cheek, chin (including the area above the upper lip), and right cheek. The counts in each section were added up to give a total lesion count number.

3. Clinical Grading Parameters: At the Baseline, Week 2, Week 4, Week 8 and Week 12 visits clinical grading parameters (Overall Healthy Appearance of Skin Condition, Even Skin Tone, Skin Texture*, Global Fine Lines, Pore Appearance, Global Wrinkles, Skin Clarity, Fine Lines—Crow's Feet and Under Eye, Radiance, Coarse Wrinkles—Crow's Feet and Under Eye, Oiliness, Overall Photodamage, Plumpness/Fullness, Skin Firmness* [*assessed by touch]) were assessed using a 0-9 modified Griffiths scale where 0=none, 1-3=mild, 4-6=moderate and 7-9=severe. In addition, sub-orbital skin elasticity was assessed via pinch-recoil measurement. The Principal Investigator gently pinched the skin of the subject's lower eyelid using the thumb and forefinger. The Principal Investigator held the skin in place for approximately 3 seconds. A decrease in pinch-recoil times indicated an improvement in skin elasticity/resiliency. The pinch-recoil response was graded on a 0-9 scale where 0=none, 1-3=mild skin laxity, 4-6=moderate skin laxity, and 7-9=severe skin laxity.

4. Clinical Tolerance Scores and Safety Endpoints: At the Baseline, Week 2, Week 4, Week 8 and Week 12 visits the following parameters were assessed by the Principal Investigator or by the subject (via interview by the Principal Investigator) using a 0-3 scale where 0=None, 1-1.5=Mild, 2-2.5=Moderate and 3-3.5=Severe). Principal Investigator: erythema, edema, dryness, scaling, and peeling. Subject: burning/itching, itching, and tightness.

Sebumeter Measurements: At the Baseline, and Week 8 visits a Sebumeter was used to assess sebum quantities on the skin surface (skin oiliness). The Sebumeter used grease spot photometry for the qualification of sebum. A single reading was taken from all subjects at the center of the forehead and on the center of the left cheek (to measure outside the T-zone area). The same placement was used for all readings for each subject by placing a small probe (similar size to the eraser on a pencil) on the skin. No pain, discomfort, or known documented ill effects were associated with this procedure. The Week 8 measurements was taken at about the same time (+/−3 hours) as the Baseline visit to assure the same level of sebaceous gland activity.

Ultrasound Measurements: At the Baseline visit 15 subjects were chosen by the Principal Investigator who had moderate crow's feet wrinkles (score of 4-6 on a 0-9 scale) to have Ultrasound measurements performed of both left and right crow's feet areas at the Baseline and Week 8 visits. The Ultrasound Echography was used to measure the skin thickness. This was done with a DermaScan C (Cortex Technology, Hadsund, Denmark). This consisted of a hand held probe that contained an ultrasonic transducer which was interfaced to a specially configured computer. The probe had a built-in closed water path and was capable of scanning an area of the skin surface 12.1 mm in length. To ensure good transmission of the ultrasound signals, a water compatible ultrasound gel (Dane Gel, cyberDerm, Inc. Broomall, Pa.) was used as a skin contact medium. The scanner processed four frames per second and displayed the results as a live-B-mode image. A standard medium focus 20 MHz transducer with maximum focal distance of 13 mm was employed. With this transducer, the axial system resolution was 60 µm and the lateral system resolution was 150 µm. Gain settings were selected that produced the best visualization of the test site, this gain setting was recorded for each person and was used for subsequent visits so changes in echo strength could accurately be evaluated.

Cutometer Measurements: At the Baseline, Week 4 and Week 8 visits all subjects had a single cutometer measurement conducted on the right ocular bone directly beneath the center of the eye. The cutometer measured elasticity (skin firmness) of the upper skin layers using a negative pressure that was created in the device and applied perpendicularly to the skin surface; in the time strain mode, skin was drawn in to the aperture of the probe by a constant vacuum that was applied to the skin surface fir a defined time and then the vacuum was reduced to 0 mbar so the skin could return to its original shape. The penetration depth of the skin in the probe was measured by a non-contact optical measuring system. Extensibility (R0), resiliency (R2), pure elasticity (R5), and biological elasticity (R7) parameters were all recorded for each subject.

Corneometer Measurements: At the Baseline, Week 2, Week 4 and Week 8 visits all subjects had corneometer measurements of the left cheek. The corneometer was used to measure the moisture content of the skin. This measurement was performed by having a small open probe placed on the skin surface. Three single readings were taken per subject on the center of the left cheek (at the intersection of lines extending up from the corner of the mouth and horizontally across the bottom of the nose) at each visit.

Skin Surface Impressions: At the Baseline, Week 8 and Week 12 visits skin surface impressions (replicas) were performed on both left and right crow's feet areas on up to 15 subjects chosen by the Principal Investigator at Baseline. Silflo impressions performed at each visit. The skin impressions were obtained with silicone dental impression material. A thin layer of freshly prepared material was gently spread over the bounded area of a ring using a stainless steel spatula. The material polymerized after about 2-3 minutes after which the ring together with the impression was lifted from the skin. Each specimen was immediately coded with the subject's number, time point and test site, then stored for analysis. A Digital Image Analysis System consisting of Visioline VL 650 hardware (Courage+Khazaka, Cologne, Germany) with a specialized image analysis software package (Image-Pro Premiere) was used for impression analysis. This system consisted of a high resolution black and white video camera interfaced with a computer. An LED illuminator was used to cross illuminate the specimen perpendicular to the major lines which accentuated the surface details. Images were made with the illuminator at a fixed angle and distance while the specimen was positioned on a turntable. The resulting images consisted of a series of shadows that directly corresponded to the pattern of wrinkles. During the analysis the changes in the skin surface topography were measured by selecting a gray level threshold that allowed the projected area of the shadowed region associated with the wrinkles to be directly determined. Changes in the skin surface topography were quantified by measuring the dimensions of the individual shadows as well as the overall area of shadowing.

Subject Questionnaires: At Baseline, Week 2, Week 4, Week 8 and Week 12 visits, subjects completed a self-assessment questionnaire while seated in front of a mirror.

Study Products: 1. Wash (UNBLEMISH Acne Treatment Sulfur Wash), 2. Toner (UNBLEMISH Clarifying Toner), 3. Treatment (UNBLEMISH Dual Intensive Acne Treatment), 4. SPF (UNBLEMISH oil Control Lotion SPF 20), 5. Hydration Serum (ENHANCEMENTS Active Hydration Serum), 6. Night serum (REDEFINE Intensive Renewing Serum).

Product Application: Each subject received a skin regimen (Wash, Toner, Treatment, and SPF) and a Night Serum at the Baseline visit for daily morning and evening applications for 12 weeks. Subjects received a Hydration Serum for evening applications Weeks 9-12. Subjects applied the skin regimen to their full face following the instructions. Both written and verbal instructions were provided to each subject prior to their first application.

Results are provided in Tables 28-31.

TABLE 28

Summary of Results- Change from Baseline

| Assessment | Week 2 | Week 4 | Week 8 | Week 12 |
| --- | --- | --- | --- | --- |
| Overall healthy appearance of skin condition | 43% improve 57% same | 83% improve 17% same | 87% improve 17% same | 91% improve 9% same |
| Skin Texture (tactile) | 91% improve 9% same | 100% improve | 100% improve | 100% improve |
| Pore appearance | 39% improve 61% same | 48% improve 52% same | 57% improve 43% same | 57% improve 43% same |
| Skin clarity | 74% improve 26% same | 91% improve 9% same | 100% improve | 100% improve |
| Radiance | 35% improve 65% same | 65% improve 35% same | 91% improve 9% same | 91% improve 4% same 4% worse |
| Oiliness | 91% improve 9% same | 96% improve 4% same | 96% improve 4% same | 100% improve |
| Plumpness/ Fullness (Visual) | 4% improve 96% same | 35% improve 65% same | 70% improve 30% same | 78% improve 22% same |
| Even skin tone | 22% improve 78% same | 57% improve 43% same | 70% improve 30% same | 74% improve 26% same |
| Global fine lines | 4% improve 96% same | 17% improve 83% same | 26% improve 74% same | 30% improve 70% same |
| Global wrinkles | 4% improve 96% same | 22% improve 78% same | 30% improve 70% same | 35% improve 65% same |
| Fine lines- Crow's feet and under eye | 17% improve 83% same | 30% improve 70% same | 35% improve 65% same | 52% improve 48 same |

TABLE 28-continued

Summary of Results- Change from Baseline

| Assessment | Week 2 | Week 4 | Week 8 | Week 12 |
| --- | --- | --- | --- | --- |
| Coarse lines-Crow's feet and under eye | 9% improve<br>87% same<br>4% worse | 22% improve<br>74% same<br>4% worse | 22% improve<br>74% same<br>4% worse | 30% improve<br>65% same<br>4% worse |
| Overall photodamage | 4% improve<br>96% same | 17% improve<br>83% same | 30% improve<br>70% same | 43% improve<br>57% same |
| Skin firmness (tactile) | 9% improve<br>91% same | 9% improve<br>91% same | 22% improve<br>78% same | 26% improve<br>74% same |
| Pinch Recoil (Elasticity/ Resiliency) | 13% improve<br>87% same | 13% improve<br>87% same | 13% improve<br>87% same | 13% improve<br>87% same |
| Erythema | 91% same<br>9% worse | 100% same | 100% same | 100% same |
| Dryness | 83% same<br>17% worse | 96% same<br>4% worse | 100% same | 100% same |
| Scaling | 96% same<br>4% worse | 100% same | 100% same | 100% same |
| Peeling | 87% same | 96% same<br>4% worse | 100% same | 100% same |
| Burning | — | 96% same<br>4% worse | 100% same | 4% improve<br>96% same |
| Stinging | — | 9% improve<br>83% same<br>9% worse | 9% improve<br>91% same | 9% improve<br>91% same |
| Itching | — | 96% same<br>4% worse | 100% same | 4% improve<br>96% same |

TABLE 29

IGA and Lesion Count % Change from Baseline

| Assessment | Week 2 | Week 4 | Week 8 |
| --- | --- | --- | --- |
| Investigator Global Acne (IGA) | −37% | −59% | −65% |
| Inflammatory Lesions | −45% | −65% | −82% |
| Non-inflammatory lesions | −12% | −30% | −27% |
| Macules | −22% | −16% | 13% |

TABLE 30

Instrument Data Summary- % Change from baseline

| Assessment | Week 2 | Week 4 | Week 8 |
| --- | --- | --- | --- |
| Corneometer-Left Cheek Average | 1% | 7% | 22% |
| Cutometer-Extensibility Right | −16% | −9% | — |
| Cutometer-Resiliency Right | −4% | 3% | — |
| Cutometer-Pure elasticity | 7% | 8% | — |
| Cutometer-Biological Elasticity | 2% | 5% | — |
| Sebumeter-Center of Forehead | — | — | −18% |
| Sebumeter-Center of Left cheek | — | — | −2% |

TABLE 31

Self-Assessment Questionnaire Data Summary- % Change form Baseline

| Question | Week 2 | Week 4 | Week 8 | Week 12 |
| --- | --- | --- | --- | --- |
| Appearance of hyperpigmentation/ pigmentation/ discoloration | 21% | 25% | 29% | 42% |
| Skin firmness | −4% | 4% | 16% | 6% |
| Skin texture | 7% | 14% | 25% | 32% |
| Skin radiance/ luminosity/ glow | 26% | 27% | 45% | 60% |
| Appearance of lines/ wrinkles | 3% | 1% | 15% | 21% |
| Skin softness | −4% | 4% | 15% | 19% |
| Skin Plumpness | 2% | 10% | 21% | 21% |
| Skin suppleness | 7% | 10% | 20% | 28% |
| Skin Tone evenness | 23% | 28% | 53% | 69% |
| Acne breakouts | 92% | 95% | 111% | 135% |
| Appearance of Pimples/Breakouts | 90% | 105% | 132% | 147% |
| Number of Pimples/Breakouts | 77% | 76% | 99% | 113% |
| Size of Pimples/Breakouts | 52% | 53% | 69% | 76% |
| Severity of Pimples/Breakouts | 52% | 56% | 71% | 83% |
| Oiliness of skin | 38% | 60% | 75% | 59% |
| Skin Moisturization | 8% | 16% | 41% | 32% |
| Appearance of Redness Associated with Pimples/Breakouts | 28% | 44% | 69% | 77% |
| Skin Clarity/ Translucency | 36% | 46% | 78% | 79% |
| Appearance of pores | 35% | 35% | 51% | 55% |
| Overall skin appearance | 47% | 54% | 79% | 88% |
| Overall Skin condition | 56% | 58% | 80% | 90% |
| Skin looks healthy | 45% | 51% | 74% | 72% |
| Skin feels healthy | 38% | 37% | 58% | 67% |

Conclusion: Twenty three (23) subjects aged 22 to 45 years completed this twelve (12) week study (target accrual was twenty five). All received a skin care regimen (Wash, Toner, Acne Treatment, and SPF) plus serums (Night and Hydration). Statistically significant improvement and tolerability was demonstrated over the twelve (12) week study period.

Acne improved significantly with reduction of IGA and Inflammatory & Non-Inflammatory Lesion Counts. Statistically significant improvement of IGA was seen as early as Week 2. Inflammatory Lesion Counts and Non-inflammatory Lesion Counts demonstrated statistically significant reduction by Week 2 and Week 4, respectively.

All clinical grading parameters demonstrated statistically significant improvement except Pinch Recoil. Eight (8) of fifteen (15) parameters demonstrated statistically significant reduction (improvement) as early as Week 2 and four (4) of fifteen (15) by Week 4. Statistically significant improvement was seen in Skin Firmness and Crow's Feet & Under-eye Course Lines by Week 8 and Week 12, respectively.

Corneometer measurements from the central and left cheek demonstrated statistically significant improvement in moisture content (hydration) at Week 8. Cutometer measurements from the right suborbital face demonstrated improvement in elasticity (skin firmness) measurements. While Pure and Biological Elasticity demonstrated improvement, Extensibility achieved statistically significant improvement as both Week 2 and Week 4. Minimal changes were seen for Resiliency. Sebumeter measurements from the central forehead and left cheek demonstrated 18% and 2% sebum reduction at Week 8, respectively. These changes were not statistically significant. Image analysis of Skin Surface Impressions (replicas) of the crow's feet areas demonstrated statistically significant reduction in Shadow Area (lines) at Week 8 (24% reduction) and Week 12 (33% reduction). Ultrasound measurements of the crow's feet areas showed no statistically significant changes in Thickness and Intensity at Week 8 and Week 12 compared to baseline.

Product-related skin irritation was reported by one subject who did not complete the study and statistically significant Dryness and near statistically significant Peeling was noted at Week 2. For the remainder of the 12 week study, clinical tolerance scores demonstrated no statistically significant changes.

Subject Questionnaire responses revealed statistically significant favorable responses in the majority of questions.

In summary, the treatment regimen plus serums significantly improved acne and appearance and was well tolerated.

Example 11: Effect of 6 Test Materials on the Activation of Retinoic Acid Response Element (RARE) Transcription Factor Pathway Objective: Retinoic Acid Receptor (RAR) controls gene transcription by binding to Retinoid Acid Response Elements (RAREs) in DNA. This process is modulated by all trans retinoic acid (ATRA)—a compound with well-established anti-aging skin benefits. Despite these benefits ATRA also exhibits undesirable side effects, and the discovery of ATRA functional analogues with improved therapeutic and/or cosmetic activity profile is highly desirable. Cignal RARE Reporter Assay® is designed to screen for such compounds using cell cultures. The objective of this project was to test 6 compounds (retinoic acid (ATRA), retinol, vitamin A palmitate, retinal, 10% w/w Near-1 in dimethylisosorbide, and 10% w/w retinoid ester in dimethylisosorbide) for the ability to activate RARE in this Cignal RARE Reporter Assay model.

Materials & Methods: The experiments were performed using HEK293 cells (Sigma, St. Louis, Mo.; cat. #85120602) seeded at 50,000 per well in a 96 well black-wall tissue culture plate. Cells were transfected by mixing Cignal Reporter Assay firefly/renilla luciferase constructs (cat. #CCS-016L; Qiagen) with Attractene Transfection Reagent (Qiagen) in Opti-MEM supplemented with 1% MEM Non-essential amino acid solution without L-glutamine. After medium change test materials were added and their effect on RARE induction was quantified 24 h later with the Dual-Luciferase Reporter Assay System (cat. #E1960; Promega).

Results and Discussion: RARE-mediated luciferase expression for each experimental condition measured in chemoluminescence units and as fold change vs. water control showed statistically-significant increase for all ATRA concentrations, which provided technical validation of the experiment. All test materials except Vit-A-Pal were active with Retinal being the best performer, followed by Near-1. As determined by the Renilla readings, none of the compounds were toxic at the tested concentrations. Overall, retinal is 1.7 times less effective than retinoic acid in modulating the RARE pathway at 1 uM, equivalent to retinoic acid at 5 uM. Table 32 presents the effect of test materials on RARE-mediated gene expression as % for all experimental conditions.

TABLE 32

Effect of test materials on the RARE-mediated firefly luciferase expression expressed as % water control and fold change vs. water. P value was calculated using two-tailed Student test.

| Test Material | % control | P value | Fold increase |
|---|---|---|---|
| Water | 100 | 1.000 | 1.000 |
| 0.4% DMSO | 97 | 0.815 | 0.97 |
| 5 µM ATRA | 973 | 0.000 | 9.7 |
| 1 µM ATRA | 1054 | 0.000 | 10.5 |
| 0.2 µM ATRA | 775 | 0.000 | 7.8 |
| 10 µM Retinol | 278 | 0.000 | 2.8 |
| 5 µM Retinol | 268 | 0.000 | 2.7 |
| 1 µM Retinol | 138 | 0.001 | 1.4 |
| 10 µM Vit A Palmitate | 86 | 0.086 | 0.9 |
| 5 µM Vit A Palmitate | 77 | 0.043 | 0.8 |
| 1 µM Vit A Palmitate | 75 | 0.007 | 0.7 |
| 10 µM Retinal | 946 | 0.000 | 9.5 |
| 5 µM Retinal | 1005 | 0.000 | 10.0 |
| 1 µM Retinal | 613 | 0.000 | 6.1 |
| 10 µM NEAR-1 | 586 | 0.000 | 5.8 |
| 5 µM NEAR-1 | 652 | 0.000 | 6.5 |
| 1 µM NEAR-1 | 461 | 0.000 | 4.6 |
| 10 µM Retinoid Ester | 281 | 0.000 | 2.8 |
| 5 µM Retinoid Ester | 230 | 0.000 | 2.3 |
| 1 µM Retinoid Ester | 147 | 0.001 | 1.5 |
| 1 µM ATRA | 1284 | 0.000 | 12.8 |
| 0.2 µM ATRA | 1099 | 0.000 | 11.0 |
| 10 µM Retinol | 294 | 0.000 | 2.9 |
| 5 µM Retinol | 253 | 0.000 | 2.5 |
| 1 µM Retinol | 150 | 0.001 | 1.5 |
| 10 µM Vit A Palmitate | 67 | 0.006 | 0.7 |
| 5 µM Vit A Palmitate | 73 | 0.004 | 0.7 |
| 1 µM Vit A Palmitate | 76 | 0.012 | 0.8 |

Example 12: Effect of 4 Test Materials on the Activation of Retinoic X Receptor Transcription Factor Pathway Objective: Retinoid X receptors (RXRs) are one class of nuclear receptors through which retinoids mediate their biological effects. These receptors function as transcription factors by binding as heterodimers to specific sequences in the promoters of target genes. The protein encoded by this gene is a member of the steroid and thyroid hormone receptor superfamily of transcriptional regulators. One of its ligands is all trans retinoic acid (ATRA)—a compound with well-established anti-aging skin benefits. Despite these benefits ATRA also exhibits undesirable side effects, and the discovery of ATRA functional analogues with improved therapeutic and/or cosmetic activity profile is highly desirable. Cignal RXR Reporter Assay® is designed to screen for such compounds (retinoic acid (ATRA), retinal, 10% w/w Near-1 in dimethylisosorbide, and 10% w/w retinoid ester in dimethylisosorbide) using cell cultures. The objective of this project was to test four compounds for the ability to activate RXR in this Cignal RXR Reporter Assay model.

The experiments were performed using HEK293 cells (Sigma, St. Louis, Mo.; cat. #85120602) seeded at 50,000 per well in a 96 well black-wall tissue culture plate. Cells were transfected by mixing Cignal RXR Reporter Assay firefly/renilla luciferase constructs (cat. #CCS9044L; Qiagen) with Attractene Transfection Reagent (Qiagen) in Opti-MEM supplemented with 1% MEM Non-essential amino acid solution without Lglutamine. After medium change test materials were added and their effect on RXR induction was quantified 24 h later with the Dual-Luciferase Reporter Assay System (cat. #E1960; Promega).

RXR is a mixture of an inducible retinoid X receptor—responsive firefly luciferase construct and a constitutively expressing Renilla construct, which acts as an internal control for normalizing transfection efficiencies and monitoring cell viability. Signal quantification was obtained with ThermoFisher Scientific Luminoskan Ascent Microplate Luminometer.

Results and Discussion: Results of RXR-mediated luciferase expression for each experimental condition measured in chemoluminescence units, as fold change vs. water control and as % of water control (Table 33) show statistically-significant increase for all ATRA concentrations, which provided technical validation of the experiment. All test materials except retinoid ester were active, with ATRA and Retinal being the best performers, followed by Near-1. As determined by the Renilla readings, none of the compounds were toxic at the tested concentrations.

Conclusion: NEAR-1 showed concentration dependent impact on RXR-mediated gene expression and at its highest tested concentration of 10 uM it demonstrated statistically-significant modulatory effect (1.3 fold). Additionally, retinal is 2.4 times less effective in modulating RXR pathway in comparison to retinoic acid at 5 uM.

TABLE 33

Effect of test materials on the RXR-mediated gene expression showed as % water control.

| Test Material | RXR activation (% control) | P value |
| --- | --- | --- |
| Water | 100 | 1.000 |
| 0.2% DMSO | 106 | 0.48 |
| 5 µM ATRA | 437 | 0.000 |
| 1 µM ATRA | 340 | 0.000 |
| 0.2 µM ATRA | 201 | 0.000 |
| 10 µM Retinal | 279 | 0.000 |
| 5µM Retinal | 181 | 0.000 |
| 1 µM Retinal | 131 | 0.001 |
| 10 µM NEAR-1 | 127 | 0.000 |
| 5 µM NEAR-1 | 112 | 0.000 |
| 1 µM NEAR-1 | 103 | 0.000 |

TABLE 33-continued

Effect of test materials on the RXR-mediated gene expression showed as % water control.

| Test Material | RXR activation (% control) | P value |
| --- | --- | --- |
| 10 µM Retinoid Ester | 110 | 0.000 |
| 5 µM Retinoid Ester | 99 | 0.000 |
| 1 µM Retinoid Ester | 124 | 0.001 |

P values were calculated using two-tailed Student test. Bolded tests are experimental conditions having statistically-significant modulatory effect (≥20% difference from water control and p ≤ 0.05).

Example 13: Assessment of the Melanin-Modulatory Effect of Four Test Materials and of their Skin Irritation Potential in MelanoDerm™ Skin Substitutes Objective: The objective of this assay was to determine the ability of the test materials (dimethylisosorbide [DMI], retinoic acid [ATRA], 10% w/w NEAR-1 in dimethylisosorbide [NEAR-1], Niacinamide PC [NAD], and Kojic Acid [KA]) and combinations thereof to inhibit melanin production in MelanoDerm™ skin substitute model. The effect of these experimental conditions on the secretion of the proinflammatory cytokine IL-8 was also assessed, as a surrogate for skin irritation potential.

Tissues were equilibrated at 37° C. for 60 min. and undiluted samples (25 µl) of test materials were applied on top of tissues in duplicates. DMI and kojic acid were applied at 2.5% and 2% (w:v) respectively (dissolved in double distilled water). Tissue culture was pursued in the pigmentation-inducing medium EPI-100-NMM-113 for 14 days, with reapplication of test materials and changes of tissue culture media every 2-3 days.

At the end of the experiment, tissue pigmentation was quantified non-invasively with NS800 portable spectrophotometer (3NH Technology Co., Ltd., China). This instrument is a reflectance spectrophotometer that measures reflected light in the visible spectrum (range: 400-700 nm) recording colors in a three-dimensional space known as CIEL*a*b* color space. In this project, the L* value representing the lightness of the color was used for color assessment. For the purpose of this experiment, the range of the L* parameter spanned from 17.8 (black background) to 87.8 (white background).

Tissue culture-conditioned media were assayed for the presence of IL-8 by indirect ELISA (using Invitrogen IL-8 Human CytoSet, cat. #CHC 1303).

For melanin quantification, the MelanoDerms were frozen, solubilized in Solvable™ (Perkin Elmer) and melanin was extracted at 95° C. overnight. The colorimetric signals proportional to the concentration of extracted melanin, as well as those proportional to the IL-8 in the tissue-conditioned medium in the ELISA test were quantified with Molecular Devices microplate spectrophotometer MAX190 at 490 nm and 405 nm.

Results and Discussion: From the macroscopic documentation of all the MelanoDerm tissues at the end of the experiment, differences of color are clearly visible between the solvent controls and some test materials. Table 34 informs whether cytotoxicity may have played a role in these differences. Table 34 also reports the non-invasive MelanoDerm color measurement performed with portable spectrophotometer.

TABLE 34

Cytotoxicity, spectrophotometric color measurements and pigmentation of MelanoDerm tissues exposed to different experimental conditions for 2 weeks.

| Test Material | Cytotoxicity | Color measurement (whitening units) | Raw *L values | Melanin Content (μg/ml) | Melanin Content (% control) | p-value |
|---|---|---|---|---|---|---|
| Water | No | 0 | 42.8 | 84 | 100 | 1.000 |
| DMI:water | No | 0 | 45.5 | N/A | N/A | N/A |
| KA 2% | Yes | 9.8 | 55.3 | 38 | 38 | 0.000 |
| Retinaldehyde 1.7 mM + NAD 1.7 mM | Yes | 27.6 | 70.4 | 38 | 38 | 0.002 |
| Retinaldehyde 833 μM + NAD 833 μM | No | 26.7 | 69.5 | N/A | N/A | N/A |
| ATRA 832 μM + NAD 835 μM | Yes | 28.2 | 71.0 | 7 | 8 | 0.000 |
| NEAR-1 2.2 mM | Yes | 27.4 | 70.2 | 22 | 26 | 0.000 |
| NEAR-1 833 μM | No (possible cytotoxicity) | 30.0 | 72.8 | N/A | N/A | N/A |

Cytotoxicity of test materials was determined by microscopic observation of MelanoDerm tissues.
Non-invasive quantification of MelanoDerm pigmentation difference between test materials and solvent control was performed with portable spectrophotometer.
Numbers represent the raw *L (brightness) values (higher the value – lighter the color).
Pigmentation is expressed in μg/ml (melanin) and as % water control.
N/A: not applicable.

At the end of the experiment, melanin extraction was initiated for selected tissues and completed two days later. Data analysis revealed decreased tissue pigmentation by the tested compounds, at least in part due to cytotoxicity (Table 34).

Figure 16:
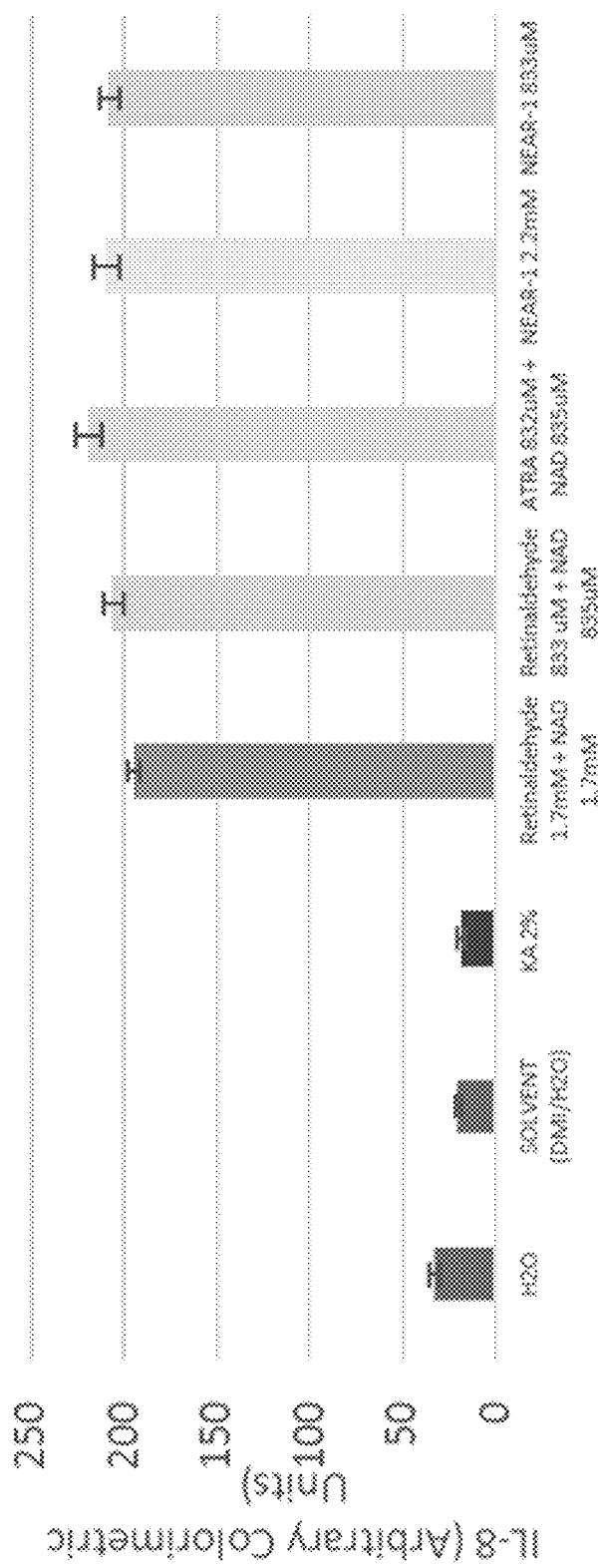
FIG. 16 graphically depicts the effect of different experimental conditions on IL-8 levels in tissue culture-conditioned medium, at the end of the experiment (day 14).

The quantification of interleukin 8 is reported in FIG. 16 and Table 35 shows a strong upregulation of this proinflammatory cytokine by all tested retinoid combinations.

TABLE 35

Actual numerical values corresponding to the IL-8 levels presented in FIG. 3.

| Test Material | IL-8 (col. Units) | p-value |
|---|---|---|
| Water | 33 | 1.000 |
| Solvent (DMI/water) | 21 | 1.000 |
| KA 2% | 19 | 0.188 |
| Retinaldehyde 1.7 mM + NAD 1.7 mM | 195 | 0.001 |
| Retinaldehyde 833 μM + NAD 833 μM | 206 | 0.000 |
| ATRA 832 μM + NAD 835 μM | 219 | 0.000 |
| NEAR-1 2.2 mM | 209 | 0.001 |
| NEAR-1 833 μM | 208 | 0.000 |

Corresponding p values reflecting statistical significance of variance vs. water control col. units (colormetric units).

Conclusion: In the retinoid category, NEAR-1 at 833 μM and [Retinaldehyde 833 μM+NAD 835 μM] combination appeared to provide the best whitening effect at non-cytotoxic concentration. Additionally, retinoic acid+niacinamide (both at 832 uM) lightened melanoderma 78% more than untreated control. In contrast, retinal+niacinamide (both at 832 uM) lightened the melanoderma 75% more versus untreated control, and was not cytotoxic. Note that niacinamide in this test was tested at 832 uM, is roughly 0.01%, which is 3 orders of magnitude (about 500 times) lower than its effective concentration for skin brightening effect, used topically in cosmetic formulation. Therefore, we consider its contribution to activity in this assay to be negligible.

What is claimed is:

1. A method of treating skin comprising:
   topically applying a composition to skin of a subject, wherein the composition comprises: retinaldehyde, palmitoyl hexapeptide-14, one or more skin conditioning agents selected from cyclopentasiloxane, dimethicone, polysilicone-11, ethylhexyl hydroxystearate, C12-15 alykl benzoate, bis-ethylhexyl hydroxydimethoxy, benzylmalonate, ethoxydiglycol, or combinations thereof, hydroxyapatite, and, retinyl palmitate,
   wherein treating the skin is an improvement in a characteristic of the skin selected from the group consisting of firmness, elasticity, fine lines and wrinkles, skin texture, dullness, dyschromia, skin tone, reduction or elimination of acne, and any combination thereof, and
   wherein the improvement in a characteristic of the skin of the subject is achieved after 4 weeks of treatment with the composition.

2. The method of claim 1, wherein the composition further comprises one or more additional retinoids selected from the group consisting of alitretinoin (9-cis-retinoic acid), tretinoin (all-trans-retinoic acid), isotretinoin (13-cis-retinoic acid), etretinate, acitretin, adapalene, bexarotene, tazarotene, hydroxypinacolone retinoate (HPR), retinoid ester, retinoate, and derivatives and combinations thereof.

3. The method of claim 1, wherein the composition further comprises one or more skin conditioning agents selected from the group consisting of hyaluronic acid, alpha hydroxyl acids, glycolic acid, lactic acid, ascorbic acid, polyhydroxy acids, gluconolactone, lactobionic acid, beta hydroxyl acid, peat extract, glycine, cetyl alcohol, stearyl alcohol, and derivatives and combinations thereof.

4. The method of claim 1, wherein the composition further comprises one or more peptides selected from the group consisting of oligopeptide-10, myristoyl pentapeptide-8, myristoyl tetrapeptide-8, sericin, silk protein, collagen, keratin, amino acids, hexapeptide-21, palmitoyl oligopeptide, palmitoyl tetrapeptide-7, tetrapeptide-16, polyacrylate-13, polyisobutene, polysorbate-20, betaine, milk solids, rice peptides, and derivatives and combinations thereof.

5. The method of claim 1, wherein the composition further comprises one or more calcium containing agents selected from the group consisting of calcium lactate, calcium chloride, calcium carbonate, calcium phosphate, calcium pyrophosphate, calcium sulfate, dicalcium phosphate, dicalcium phosphate dehydrate, tricalcium phosphate, calcium undecylenate, and derivatives and combinations thereof.

6. The method of claim 1, wherein the composition comprises retinaldehyde, cyclopentasiloxane, dimethicone, polysilicone-11, ethylhexyl hydroxystearate, C12-15 alkyl benzoate, palmitoyl hexapeptide-14, retinyl palmitate, bis-ethylhexyl hydroxydimethoxy benzylmalonate, hydroxyapatite, and ethoxydiglycol.

7. The method of claim 1, wherein the method further comprises cleansing the skin with a daily cleansing mask.

8. The method of claim 1, wherein the method further comprises topically applying a toner to the skin.

9. The method of claim 1, wherein the method further comprises exfoliating the skin.

10. The method of claim 9, wherein the exfoliating the skin occurs using a micro-dermabrasion paste, an exfoliating scrub, or an exfoliating tool.

11. The method of claim 1, wherein the method further comprises rolling the skin with a micro-exfoliation tool.

12. The method of claim 1, wherein the skin is any skin surface selected from the group consisting of scalp, face, neck, décolletage, back, arms, legs, hands, feet, chest, stomach, and buttocks.

13. The method of claim 1, wherein a subject shows the improvement in a characteristic of the skin after 8 weeks of treatment.

14. The method of claim 1, wherein a subject shows the reduction or elimination of acne after 2 weeks of treatment.

* * * * *